(12) United States Patent
Guo

(10) Patent No.: US 9,297,013 B2
(45) Date of Patent: Mar. 29, 2016

(54) PRNA MULTIVALENT JUNCTION DOMAIN FOR USE IN STABLE MULTIVALENT RNA NANOPARTICLES

(75) Inventor: Peixuan Guo, Lexington, KY (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 13/992,714

(22) PCT Filed: Jun. 5, 2012

(86) PCT No.: PCT/US2012/040823
§ 371 (c)(1),
(2), (4) Date: Jun. 7, 2013

(87) PCT Pub. No.: WO2012/170372
PCT Pub. Date: Dec. 13, 2012

(65) Prior Publication Data
US 2014/0179758 A1    Jun. 26, 2014

Related U.S. Application Data

(63) Continuation-in-part of application No. PCT/US2012/020469, filed on Jan. 6, 2012.

(60) Provisional application No. 61/494,706, filed on Jun. 8, 2011.

(51) Int. Cl.
*C07H 21/04* (2006.01)
*C12N 15/115* (2010.01)
*C12N 15/11* (2006.01)
*C12N 15/113* (2010.01)

(52) U.S. Cl.
CPC ............ *C12N 15/115* (2013.01); *C12N 15/111* (2013.01); *C12N 15/113* (2013.01); *C12N 15/1137* (2013.01); *C12N 2310/12* (2013.01); *C12N 2310/14* (2013.01); *C12N 2310/16* (2013.01); *C12N 2310/51* (2013.01); *C12N 2320/31* (2013.01); *C12N 2330/31* (2013.01)

(58) Field of Classification Search
None
See application file for complete search history.

(56) References Cited

U.S. PATENT DOCUMENTS

2010/0003753 A1    1/2010    Guo

FOREIGN PATENT DOCUMENTS

WO    WO2007016507 A3    2/2007

OTHER PUBLICATIONS

Hoeprich et al. (Gene Therapy 2003: 1258-1267).*
Assembly of multifunctional phi29 pRNA nanoparticles for specific delivery of siRNA and other therapeutics to targeted cells, Yi Shu etc. Methods, vol. 54, 204-214, 2011.

* cited by examiner

*Primary Examiner* — Kimberly Chong
(74) *Attorney, Agent, or Firm* — Yonghao Hou; Faegre Baker & Daniels LLP

(57) ABSTRACT

Trifurcate RNA junction domains derived from phi29 pRNA are described that assemble with high affinity and that are stable in vitro and in vivo. Further expansion of trifurcated RNA domains to multiple way junction scaffolds via creative designs enable an array of toolkit to construct nanoparticle architectures with diverse shapes and angles. The scaffolds can be used to form RNA nanoparticles having a wide variety of uses, including promotion of RNA crystallization, creation of RNA aptamer with high affinity to mimic antibody, delivery of therapeutic and/or diagnostic agents such as biologically active RNA-based moieties, including siRNA, ribozymes, aptamers, and others.

35 Claims, 56 Drawing Sheets

Figure 6
A. Three-way junction core
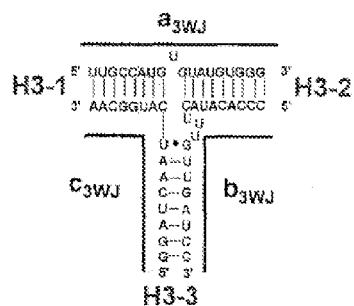
B. X-shaped core
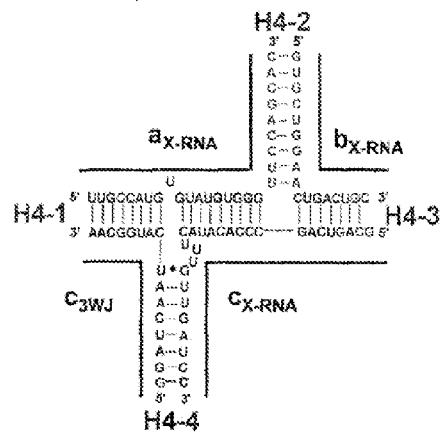
C.
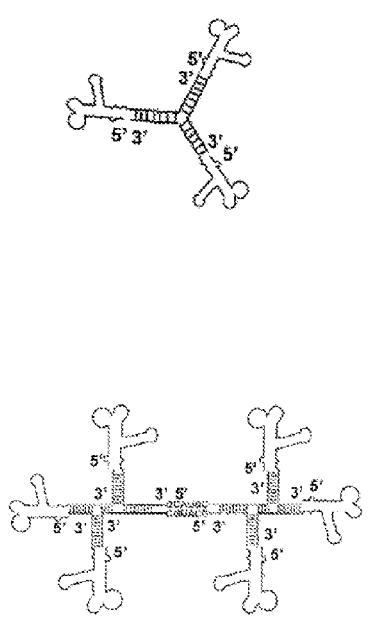
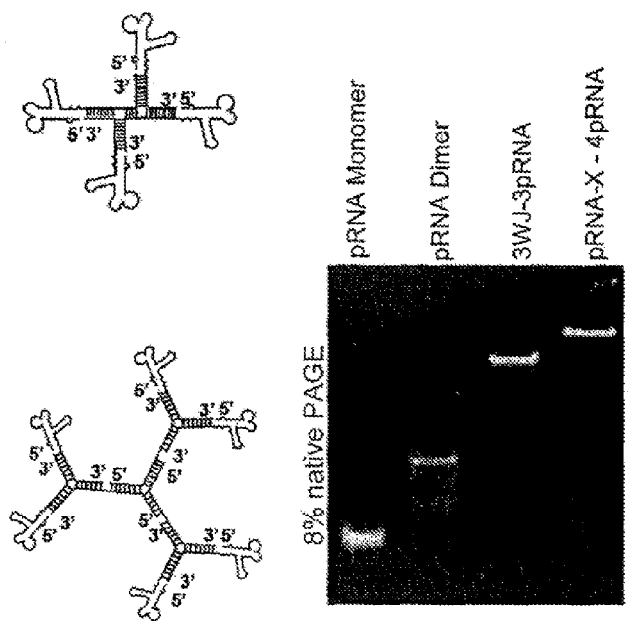

Figure 8
A Trimer:
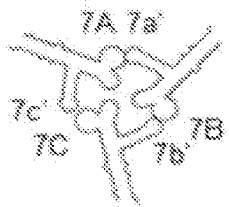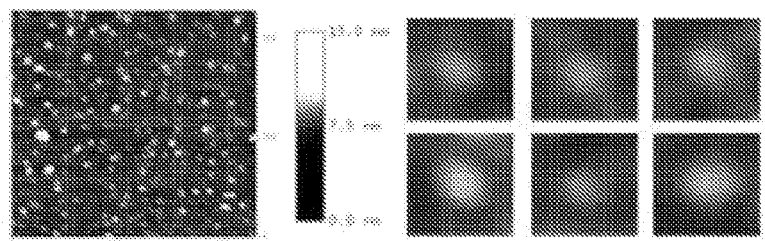
B Tetramer:
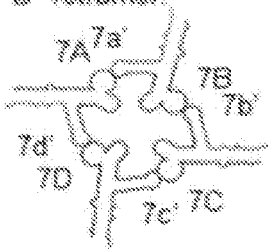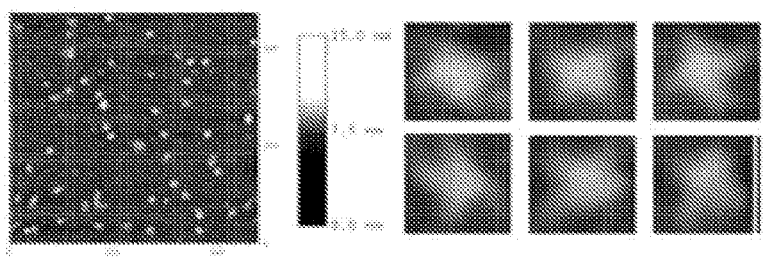
C Pentamer:
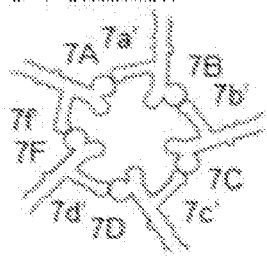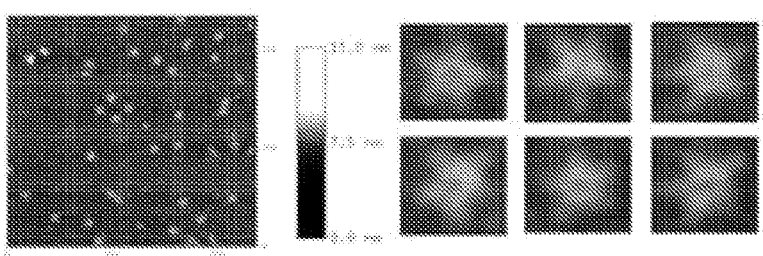
D Hexamer:
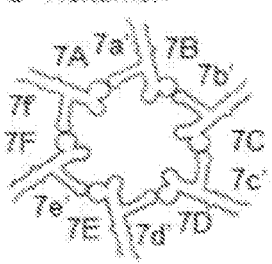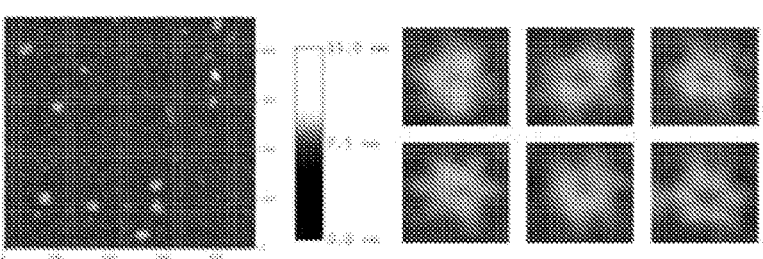
E Heptamer:
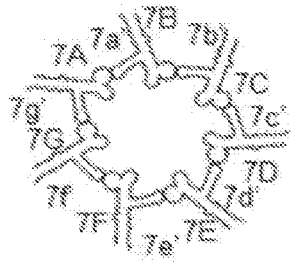

Figure 13

Figure 14     SEQ ID NO: 79-120

| Family | Name | Sequence 5'-3' | Assembly of 3WJ-pRNA harboring three pRNA monomers | |
|---|---|---|---|---|
| | | | Native Gel | 8M Urea Denaturing Gel |
| A | 16s H22-H23-H23a | a) GGA ACG CGG AUG CGG<br>b) ACG AGG GUUG GAA G<br>c) GCG AGC CAC CAG CG | No | No |
| | 16s H25-H25-H26a | a) GGG GCA AGG CGU<br>b) GGU CCA AUG CG<br>c) GCG CGA GGC CC | No | No |
| | 23s H46-Hx-H80 | a) GGC GAA UGG GU<br>b) AGC GGA AGG G<br>c) GCC CAG CGG CG | No | No |
| | 23s H99-H100-H101 | a) GAC GGU GGA AGA GU<br>b) GCC CGC GCC C<br>c) ACC ACU AGC AGA | No | No |
| B | 16s H33-H33a-H33b | a) AGG GAA CGG CGG GG<br>b) GGG AGC CCU<br>c) GCC CCG CCG GCC C | Yes | No |
| | 23s H33-H34-H35 | a) GGG GAA CGA GCU A<br>b) GAC GGU CGA GGU A<br>c) GCC GGA CUG ACC C | No | No |
| | 16s H28-H29-H43 | a) AGG GGG ACA AAG<br>b) GUG AAA ACG UGG GG<br>c) CCC CCG CGA GGC CG | No | No |
| | 16S H32-H33-H34 | a) GGGP GGA GGGG CCCC GGA GCGG CCCG AGGA G<br>b) GAC AGA UGC UGC AGG G<br>c) CAA CCG AGC CGC CCC | No | No |
| C | RNase P B-type | a) AGC CCA GGA<br>b) GGG AGA CGG CC<br>c) GCC UGG AAA CCC GG | No | No |
| | L11-RNA | a) GGCC ACG AGG GAG CGG<br>b) AGC UCA CGG CG<br>c) CCG CCG AGC AGA AGA ACG CC | No | No |
| Unknown | M2/NF | a) GGG GAG GGC ACA CGA GUG GG<br>b) CCC ACA UUG CGG CCC G<br>c) GCCC UCG CGG CAA | Yes | No |
| | SF5 | a) GGA GGG AGG UCA GAC GG<br>b) CCG ACA GCA GGG CAG<br>c) CUC UCCG CUG CC | Yes | No |
| | B103 | a) GGCGGAAGGCGAAAAAAGGCGGG<br>b) CCCGACAGCGG CAG CCGG<br>c) CCCGCGUUCGC | Yes | No |
| | GA1 | a) AAA GGG GGC UCG GGA AGA G<br>b) CCC GCG ACA CGG GGU AGG<br>c) CCA ACA CCG UGG AG | No | No |

Figure 31
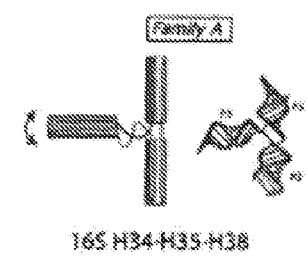
The sequences of the 3wj derived from 16S rRNA junction motifs (Family A).
16S H34-H35-H38
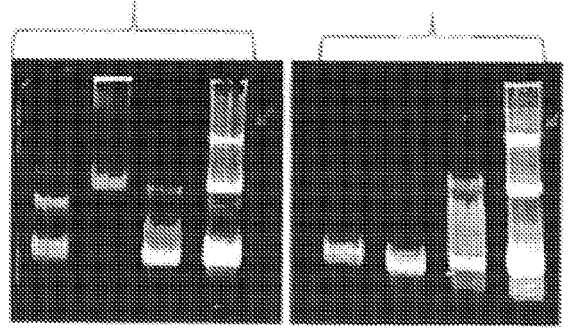
Eric Westhoff, RNA, 2006    pRNA 3WJ control
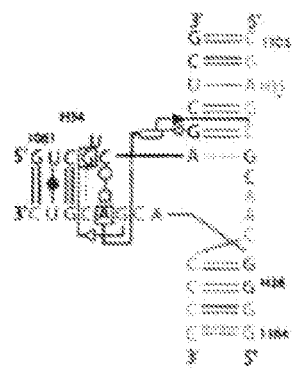

2 Structures:
 -3WJ from pRNA
 -S1 Truncated Aptamer (shows same efficiency of full Aptamer)

Figure 41
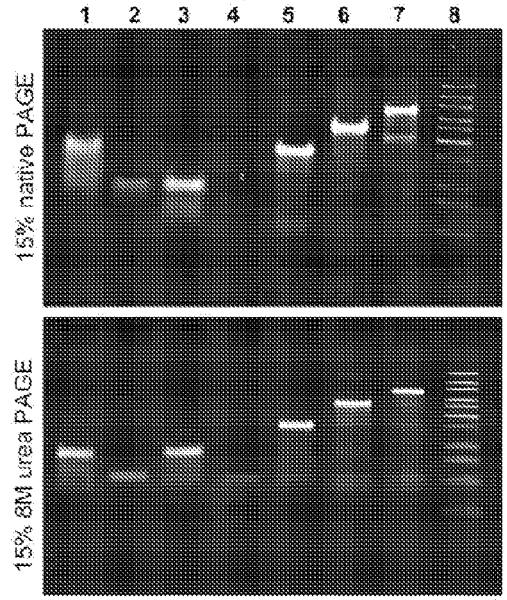
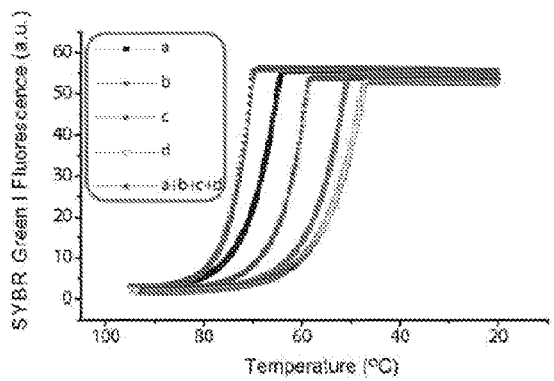

Figure 42
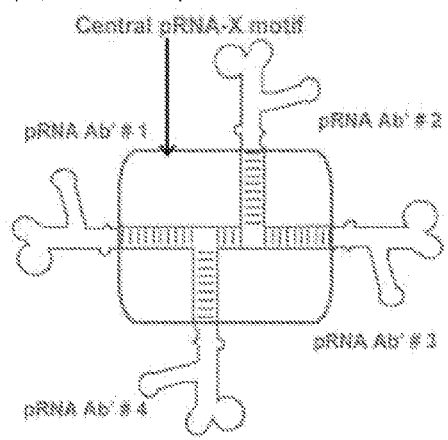
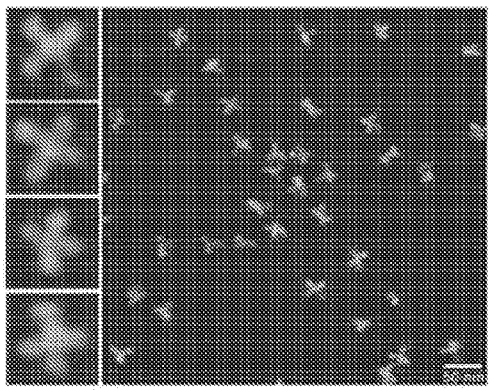
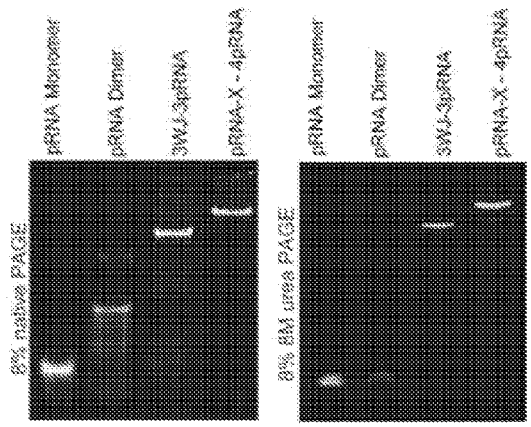
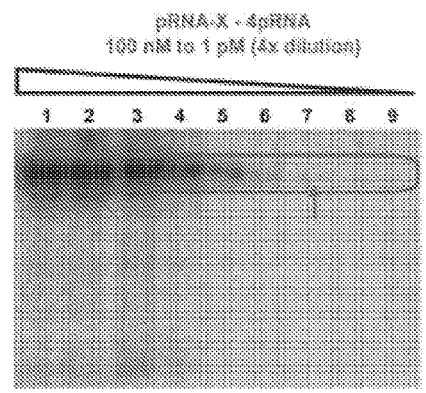

Figure 43
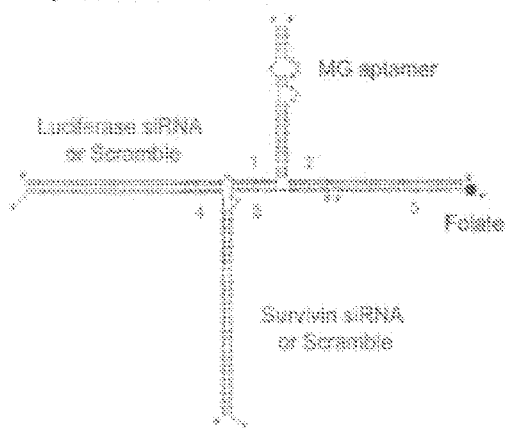
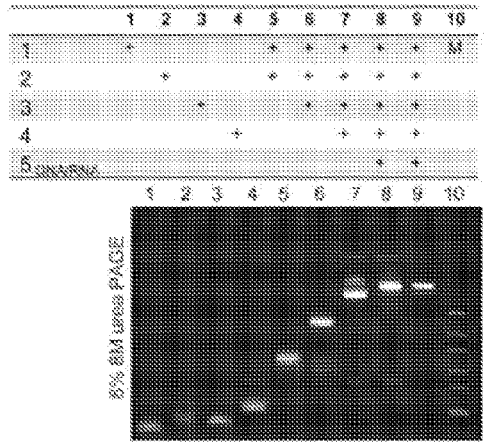
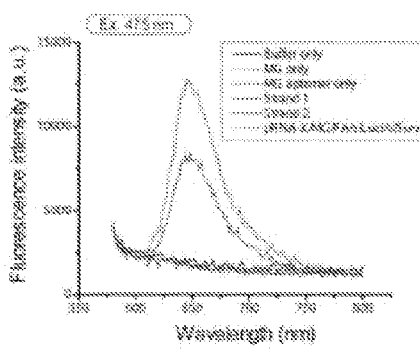
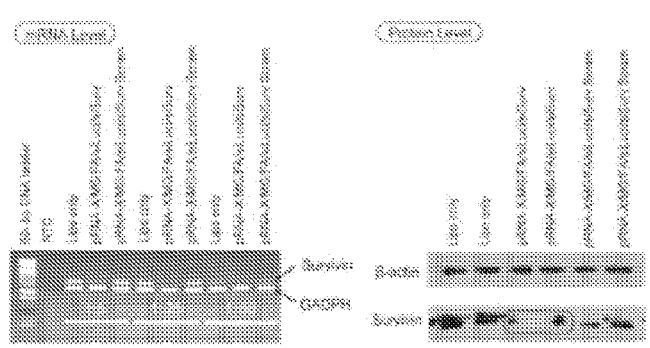
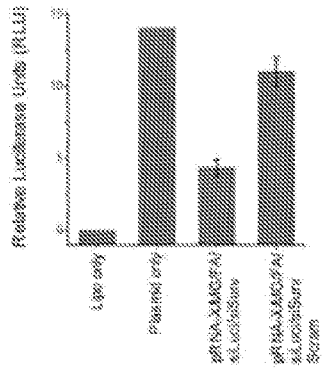

Figure 44
A In vitro binding and entry of tetravalent pRNA-X nanoparticles
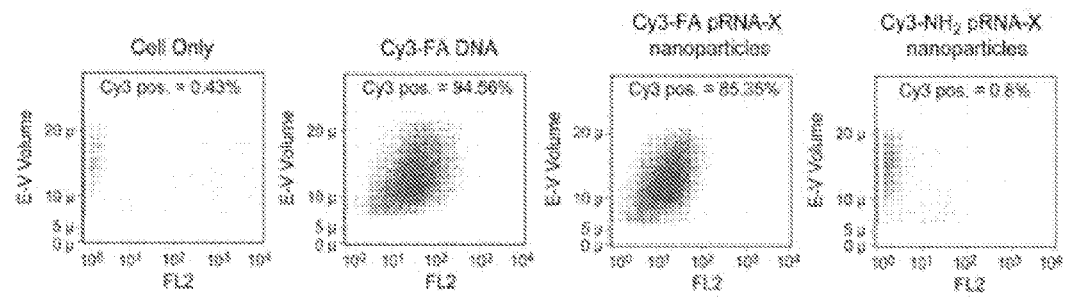
B Targeting of FA+ KB cells by tetravalent pRNA-X nanoparticles
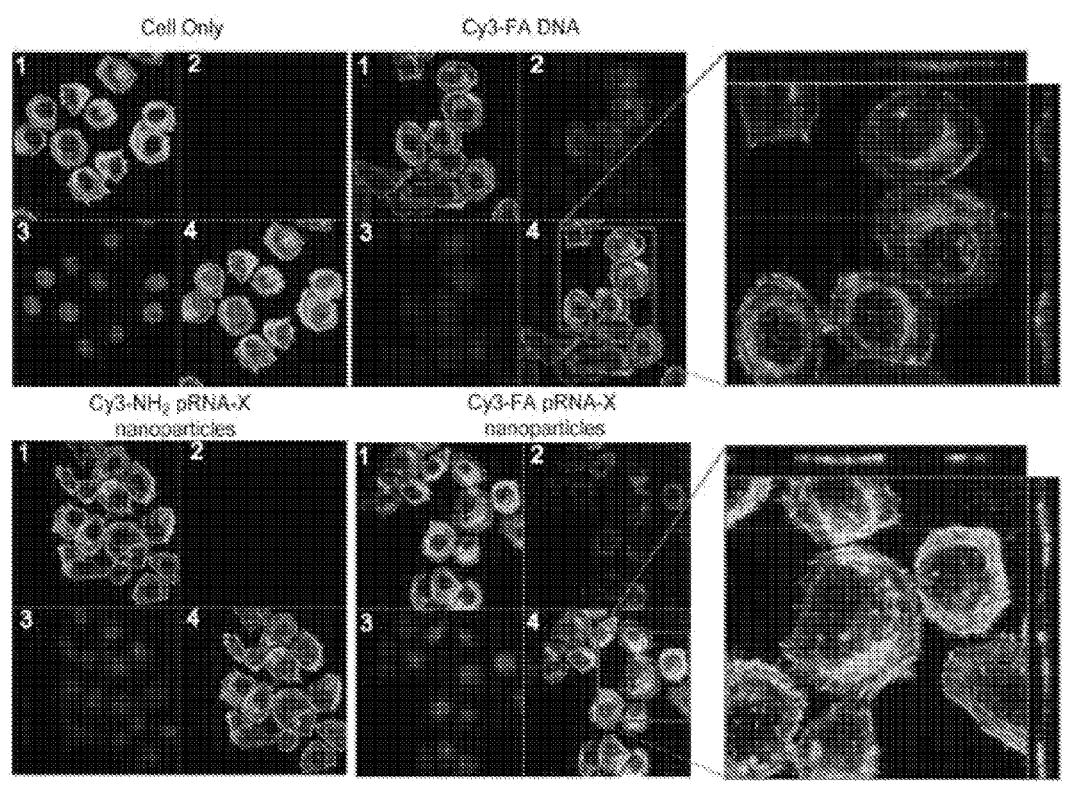

Figure 45
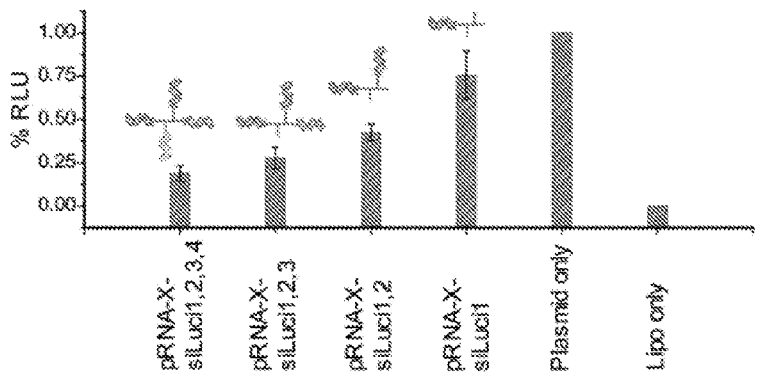
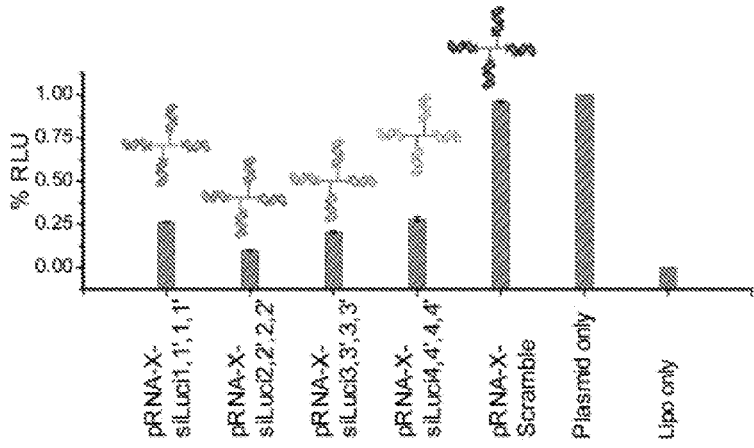

Figure 48
A  Foot-to-foot dimer
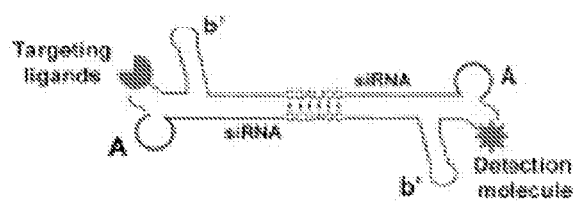 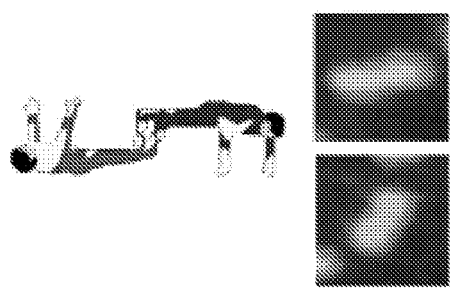
B  Tetramer
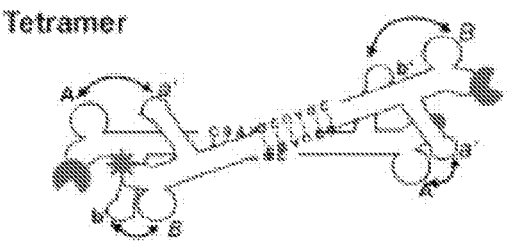 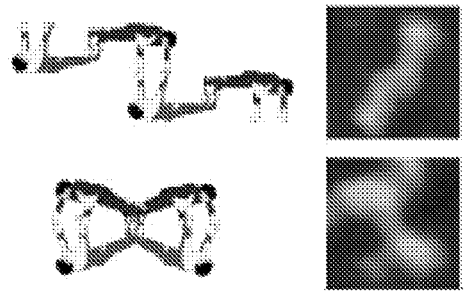

Figure 51
A
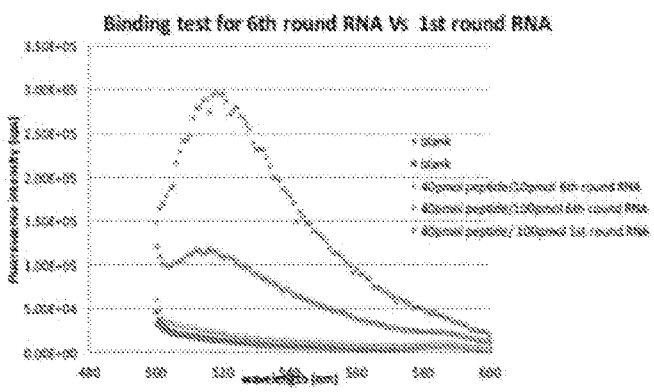
B
Assemble 3WJ RNA nanoparticle in TMS buffer.
sample 1: (10uM * 10ul)
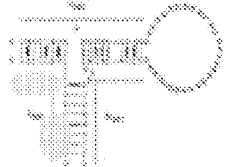
Sample 2: (10uM *10ul)
Sample 3: (10uM * 10ul)
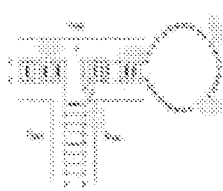
C
Test the sample by 8% Native Page
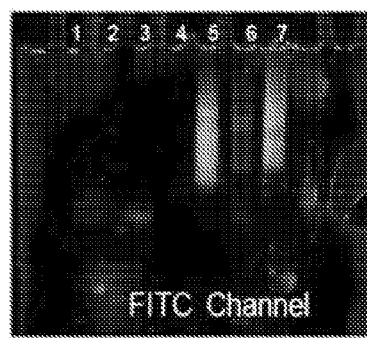
1. Ladder
2. $C_{3wj}$
3. FITC-$C_{3wj}$
4. 6th RNA library
5. FITC-6th RNA Library
6. Sample 1
7. Smaple 3

Figure 52
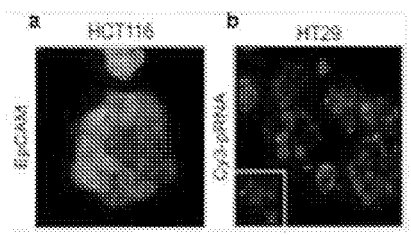
A
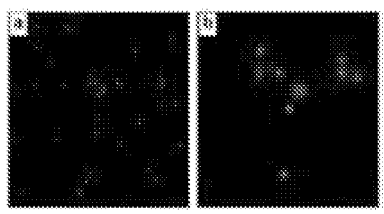
B
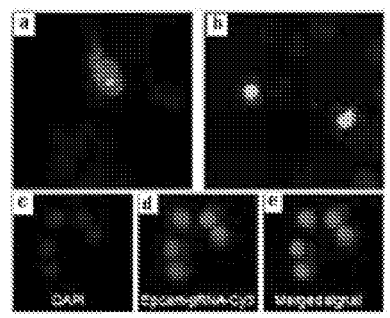
C
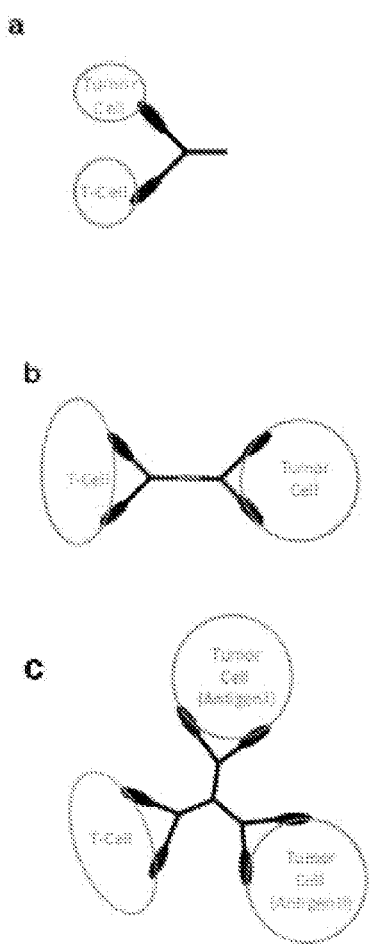
D

FIG. 53

Table 1 Sequence of loop extended pRNA homo-dimers and hetero-monomers

| name | | RNA sequence (5'→ 3') |
|---|---|---|
| Homo-dimers | 7Aa' | GGAAUGGUACGGUACUUCCAUUGUCAUGUGUAUGUUGGG<u>GAUUAAGUGGAC</u>CUGAUUGAGUU<br>CAGCCCACAUACUUUGUUGAU<u>UGUCCACU</u>GUCAAUCAUGGCAAAAGUGCACGCUACUUUCC |
| | 7Bb' | GGAAUGGUACGGUACUUCCAUUGUCAUGUGUAUGUUGGG<u>GAUUAACAGGCA</u>CUGAUUGAGUU<br>CAGCCCACAUACUUUGUUGAU<u>UUGCCUGU</u>GUCAAUCAUGGCAAAAGUGCACGCUACUUUCC |
| | 7Cc' | GGAAUGGUACGGUACUUCCAUUGUCAUGUGUAUGUUGGG<u>GAUUAGCGUUCU</u>CUGAUUGAGUU<br>CAGCCCACAUACUUUGUUGAU<u>UAGAACGC</u>GUCAAUCAUGGCAAAAGUGCACGCUACUUUCC |
| | 7Dd' | GGAAUGGUACGGUACUUCCAUUGUCAUGUGUAUGUUGGG<u>GAUUAAGGCUAG</u>CUGAUUGAGUU<br>CAGCCCACAUACUUUGUUGAU<u>UCUAGCCU</u>GUCAAUCAUGGCAAAAGUGCACGCUACUUUCC |
| | 7Ee' | GGAAUGGUACGGUACUUCCAUUGUCAUGUGUAUGUUGGG<u>GAUUAAGCACCA</u>CUGAUUGAGUU<br>CAGCCCACAUACUUUGUUGAU<u>UUGGUGCU</u>GUCAAUCAUGGCAAAAGUGCACGCUACUUUCC |
| | 7Ff' | GGAAUGGUACGGUACUUCCAUUGUCAUGUGUAUGUUGGG<u>GAUUAAGACGUG</u>CUGAUUGAGUU<br>CAGCCCACAUACUUUGUUGAU<u>UCACGUCU</u>GUCAAUCAUGGCAAAAGUGCACGCUACUUUCC |
| | 7Gg' | GGAAUGGUACGGUACUUCCAUUGUCAUGUGUAUGUUGGG<u>GAUUACACUAUC</u>CUGAUUGAGUU<br>CAGCCCACAUACUUUGUUGAU<u>UGAUAGUG</u>GUCAAUCAUGGCAAAAGUGCACGCUACUUUCC |
| | 7Hh' | GGAAUGGUACGGUACUUCCAUUGUCAUGUGUAUGUUGGG<u>GAUUAAGGCAGC</u>CUGAUUGAGUU<br>CAGCCCACAUACUUUGUUGAU<u>UGCUGCCU</u>GUCAAUCAUGGCAAAAGUGCACGCUACUUUCC |
| | 7Ii' | GGAAUGGUACGGUACUUCCAUUGUCAUGUGUAUGUUGGG<u>GAUUAAGCCUGC</u>CUGAUUGAGUU<br>CAGCCCACAUACUUUGUUGAU<u>UGCAGGCU</u>GUCAAUCAUGGCAAAAGUGCACGCUACUUUCC |
| Hetero-monomers | 7Ba' | GGAAUGGUACGGUACUUCCAUUGUCAUGUGUAUGUUGGG<u>GAUUAACAGGCA</u>CUGAUUGAGUU<br>CAGCCCACAUACUUUGUUGAU<u>UGUCCACU</u>GUCAAUCAUGGCAAAAGUGCACGCUACUUUCC |
| | 7Cb' | GGAAUGGUACGGUACUUCCAUUGUCAUGUGUAUGUUGGG<u>GAUUAGCGUUCU</u>CUGAUUGAGUU<br>CAGCCCACAUACUUUGUUGAU<u>UUGCCUGU</u>GUCAAUCAUGGCAAAAGUGCACGCUACUUUCC |
| | 7Dc' | GGAAUGGUACGGUACUUCCAUUGUCAUGUGUAUGUUGGG<u>GAUUAAGGCUAG</u>CUGAUUGAGUU<br>CAGCCCACAUACUUUGUUGAU<u>UAGAACGC</u>GUCAAUCAUGGCAAAAGUGCACGCUACUUUCC |
| | 7Ed' | GGAAUGGUACGGUACUUCCAUUGUCAUGUGUAUGUUGGG<u>GAUUAAGCACCA</u>CUGAUUGAGUU<br>CAGCCCACAUACUUUGUUGAU<u>UCUAGCCU</u>GUCAAUCAUGGCAAAAGUGCACGCUACUUUCC |
| | 7Fe' | GGAAUGGUACGGUACUUCCAUUGUCAUGUGUAUGUUGGG<u>GAUUAAGACGUG</u>CUGAUUGAGUU<br>CAGCCCACAUACUUUGUUGAU<u>UUGGUGCU</u>GUCAAUCAUGGCAAAAGUGCACGCUACUUUCC |
| | 7Af | GGAAUGGUACGGUACUUCCAUUGUCAUGUGUAUGUUGGG<u>GAUUAAGUGGAC</u>CUGAUUGAGUU<br>CAGCCCACAUACUUUGUUGAU<u>UCACGUCU</u>GUCAAUCAUGGCAAAAGUGCACGCUACUUUCC |
| | 7Ab' | GGAAUGGUACGGUACUUCCAUUGUCAUGUGUAUGUUGGG<u>GAUUAAGUGGAC</u>CUGAUUGAGUU<br>CAGCCCACAUACUUUGUUGAU<u>UUGCCUGU</u>GUCAAUCAUGGCAAAAGUGCACGCUACUUUCC |
| | 7Ac' | GGAAUGGUACGGUACUUCCAUUGUCAUGUGUAUGUUGGG<u>GAUUAAGUGGAC</u>CUGAUUGAGUU<br>CAGCCCACAUACUUUGUUGAU<u>UAGAACGC</u>GUCAAUCAUGGCAAAAGUGCACGCUACUUUCC |
| | 7Ad' | GGAAUGGUACGGUACUUCCAUUGUCAUGUGUAUGUUGGG<u>GAUUAAGUGGAC</u>CUGAUUGAGUU<br>CAGCCCACAUACUUUGUUGAU<u>UCUAGCCU</u>GUCAAUCAUGGCAAAAGUGCACGCUACUUUCC |

FIG. 53 Continued

| | |
|---|---|
| 7Fd' | GGAAUGGUACGGUACUUCCAUUGUCAUGUGUAUGUUGGG<u>GAUUAAGACGUG</u>CUGAUUGAGUU<br>CAGCCCACAUACUUUGUUGAUU<u>CUAGCC</u>UGUCAAUCAUGGCAAAAGUGCACGCUACUUUCC |
| 7Gf | GGAAUGGUACGGUACUUCCAUUGUCAUGUGUAUGUUGGG<u>GAUUACACUAUC</u>CUGAUUGAGUU<br>CAGCCCACAUACUUUGUUGAUU<u>CACGUC</u>UGUCAAUCAUGGCAAAAGUGCACGCUACUUUCC |
| 7Ag' | GGAAUGGUACGGUACUUCCAUUGUCAUGUGUAUGUUGGG<u>GAUUAAGUGGAC</u>CUGAUUGAGUU<br>CAGCCCACAUACUUUGUUGAUU<u>GAUAGUGG</u>UCAAUCAUGGCAAAAGUGCACGCUACUUUCC |

FIG. 54

Table 2 Sequence of branched pRNA nanostructures

| | Name | RNA sequence (5'→ 3') |
|---|---|---|
| 3WJ-pRNA | a_{3WJ} | 5' - UUG CCA UGU GUA UGU GGG - 3' |
| | b_{3WJ} | 5' - CCC ACA UAC UUU GUU GAU CC - 3' |
| | c_{3WJ} | 5' - GGA UCA AUC AUG GCA A - 3' |
| pRNA-X | a_{X-RNA} | 5' - UUG CCA UGU GUA UGU GGG UUC CAG CAC - 3' |
| | b_{X-RNA} | 5' - GUG CUG GAA CUG ACU GC - 3' |
| | c_{X-RNA} | 5' - GCA GUC AGC CCA CAU ACU UUG UUG AUC C - 3' |
| | d_{X-RNA} | 5' - GGA UCA AUC AUG GCA A - 3' |
| Foot-to-foot Hexamer | Strands a_{X-RNA} + b_{X-RNA} + c_{X-RNA} | |
| | d_{X-RNA}+PS6 | 5' - GGA UCA AUC AUG GCA AGC AUG C - 3' |
| 3WJ-based Branched Hexamer | Strands b_{3WJ} + c_{3WJ} | |
| | a3WJ_{FWD} + a3WJ_{REV} | 5' - UUG CCA UGU GUA UGU GGG U GGG UGU AUG UGU ACC GUU - 3' |
| | a3WJ_{FWD} + b3WJ_{REV} | 5' - UUG CCA UGU GUA UGU GGG CCU AGU UGU UUC AUA CAC CC - 3' |
| | a3WJ_{FWD} + c3WJ_{REV} | 5' - UUG CCA UGU GUA UGU GGG AAC GGU ACU AAC UAG G - 3' |

FIG. 55

Table 3 Sequence of inserted functional moieties

| name | RNA sequence |
|---|---|
| MG binding aptamer | 5'-AUGGUAACGAAUGA-3' |
|  | 5'-CAAUCCGACAU-3' |
| STV binding aptamer | 5'-CGACCAGAAUCAUGCAAGUGCGUAAGAUAGUCGCGGGUCG-3' |
| folate-DNA strand | 5'-Folate-CTCCCGGCCGCCATGGCCGCGGGAT-3' |
| HBV ribozyme | working ribozyme:<br>CAAAUUCUUUACUGAUGAGUCCGUGAGGACGAAACGGGUC<br><br>disabled ribozyme:<br>CAAAUUCUUUACUAAUGAGUCCGUGAGGACGAAACGGGUC |
| firefly luciferase | siLuci 1: sense: 5'-GUGCGCUGCUGGUGCCAAC-3'<br>anti-sense: 3'-CACGCGACGACCACGGUUG-5'<br><br>siLuci 2: sense: 5'-CUUACGCUGAGUACUUCGA-3'<br>anti-sense: 3'-GAAUGCGACUCAUGAAGCU-5'<br><br>siLuci 3: sense: 5'-GCUAUGAAACGAUAUGGGC-3'<br>anti-sense: 3'-CGAUACUUUGCUAUACCCG-5'<br><br>siLuci 4: sense: 5'-UUCGUCACAUCUCAUCUAC-3'<br>anti-sense: 3'-AAGCAGUGUAGAGUAGAUG-5'<br><br>control: sense: 5'-UCUCCUUCACGAAACCGAC-3'<br>anti-sense: 3'-AGAGGAAGUGCUUUGGCUG-5' |

US 9,297,013 B2

PRNA MULTIVALENT JUNCTION DOMAIN FOR USE IN STABLE MULTIVALENT RNA NANOPARTICLES

PRIORITY CLAIMS AND CROSS REFERENCES

This invention is submitted as the national stage entry in US for international application PCT/US2012/040823, filed on Jun. 5, 2012, which claims the priority benefits under 35 U.S.C. Section 119 (e) of U.S. provisional application 61/494,706 filed Jun. 8, 2011. The provisional application is incorporated herein entirely. In addition, this invention incorporates Shu et al Nature Nanotechnology Vol. 6, October 2011, U.S. Pat. No. 7,655,787, U.S. Pat. No. 8,088,912 and PCT/US12/020469 entirely.

STATEMENT OF GOVERNMENT INTEREST

This invention was made with government support under Grant Nos. GM059944, EB003730, EY018230 and U01CA151648 awarded by the National Institutes of Health. The government has certain rights in this invention.

BACKGROUND

1. Technical Field

The presently disclosed invention embodiments relate to RNA nanoparticles and methods for their preparation and use. In particular, the present embodiments relate to multiple-way junctional fragments of dsDNA virus packaging RNA (pRNA), and their derivatives, for assembling and stabilizing multivalent RNA nanoparticles.

2. Description of the Related Art

In living systems there exists a wide variety of highly-ordered or patterned structures including smart nanomachines, and elegant arrays that are made up of macromolecules to perform diverse biological functions. Over the past 30 years, for instance, there has been a rapid expansion of knowledge in DNA nanotechnology. Both RNA and DNA share some common properties, such as polynucleotide strand complementarities and self-assembly, and can serve as powerful building blocks for bottom-up fabrication of nanostructures and nano-devices.

There has been a heightened interest in RNA therapeutics since the discovery of small interfering RNA (siRNA). RNA interference (RNAi) is a polynucleotide sequence-specific, post-transcriptional gene silencing mechanism effected by double-stranded RNA that results in degradation of a specific messenger RNA (mRNA), thereby reducing the expression of a desired target polypeptide encoded by the mRNA (see, e.g., WO 99/32619; WO 01/75164; U.S. Pat. No. 6,506,559; Fire et al., *Nature* 391:806-11 (1998); Sharp, *Genes Dev.* 13:139-41 (1999); Elbashir et al. *Nature* 411:494-98 (2001); Harborth et al., *J. Cell Sci.* 114:4557-65 (2001)). RNAi is mediated by double-stranded polynucleotides as also described hereinbelow, for example, double-stranded RNA (dsRNA), having sequences that correspond to exonic sequences encoding portions of the polypeptides for which expression is compromised. RNAi reportedly is not effected by double-stranded RNA polynucleotides that share sequence identity with intronic or promoter sequences (Elbashir et al., 2001). RNAi pathways have been best characterized in *Drosophila* and *Caenorhabditis elegans*, but "small interfering RNA" (siRNA) polynucleotides that interfere with expression of specific polypeptides in higher eukaryotes such as mammals (including humans) have also been described (e.g., Tuschl, 2001 *Chembiochem.* 2:239-245; Sharp, 2001 *Genes Dev.* 15:485; Bernstein et al., 2001 *RNA* 7:1509; Zamore, 2002 *Science* 296:1265; Plasterk, 2002 *Science* 296:1263; Zamore 2001 *Nat. Struct. Biol.* 8:746; Matzke et al., 2001 *Science* 293:1080; Scadden et al., 2001 *EMBO Rep.* 2:1107) and subsequently elaborated upon.

According to a current non-limiting model, the RNAi pathway is initiated by ATP-dependent, processive cleavage of long dsRNA into double-stranded fragments of about 18-27 (e.g., 19, 20, 21, 22, 23, 24, 25, 26, etc.) nucleotide base pairs in length, called small interfering RNAs (siRNAs) (see review by Hutvagner et al., *Curr. Opin. Gen. Dev.* 12:225-32 (2002); Elbashir et al., 2001; Nykänen et al., *Cell* 107:309-21 (2001); Zamore et al., *Cell* 101:25-33 (2000); Bass, *Cell* 101:235-38 (2000)). In *Drosophila*, an enzyme known as "Dicer" cleaves the longer double-stranded RNA into siRNAs; Dicer belongs to the RNase II family of dsRNA-specific endonucleases (WO 01/68836; Bernstein et al., *Nature* 409:363-66 (2001)). Further according to this non-limiting model, the siRNA duplexes are incorporated into a protein complex, followed by ATP-dependent unwinding of the siRNA, which then generates an active RNA-induced silencing complex (RISC) (WO 01/68836). The complex recognizes and cleaves a target RNA that is complementary to the guide strand of the siRNA, thus interfering with expression of a specific protein (Hutvagner et al., supra).

In *C. elegans* and *Drosophila*, RNAi may be mediated by long double-stranded RNA polynucleotides (WO 99/32619; WO 01/75164; Fire et al., 1998; Clemens et al., *Proc. Natl. Acad. Sci. USA* 97:6499-6503 (2000); Kisielow et al., *Biochem. J.* 363:1-5 (2002); see also WO 01/92513 (RNAi-mediated silencing in yeast)). In mammalian cells, however, transfection with long dsRNA polynucleotides (i.e., greater than 30 base pairs) leads to activation of a non-specific sequence response that globally blocks the initiation of protein synthesis and causes mRNA degradation (Bass, *Nature* 411:428-29 (2001)). Transfection of human and other mammalian cells with double-stranded RNAs of about 18-27 nucleotide base pairs in length interferes in a sequence-specific manner with expression of particular polypeptides encoded by messenger RNAs (mRNA) containing corresponding nucleotide sequences (WO 01/75164; Elbashir et al., 2001; Elbashir et al., *Genes Dev.* 15:188-200 (2001)); Harborth et al., *J. Cell Sci.* 14:4557-65 (2001); Carthew et al., *Curr. Opin. Cell Biol.* 13:244-48 (2001); Mailand et al., *Nature Cell Biol.* Advance Online Publication (Mar. 18, 2002); Mailand et al. 2002 *Nature Cell Biol.* 4:317).

siRNA polynucleotides may offer certain advantages over other polynucleotides known to the art for use in sequence-specific alteration or modulation of gene expression to yield altered levels of an encoded polypeptide product. These advantages include lower effective siRNA polynucleotide concentrations, enhanced siRNA polynucleotide stability, and shorter siRNA polynucleotide oligonucleotide lengths relative to such other polynucleotides (e.g., antisense, ribozyme or triplex polynucleotides).

By way of a brief background. "antisense" polynucleotides bind in a sequence-specific manner to target nucleic acids, such as mRNA or DNA, to prevent transcription of DNA or translation of the mRNA (see, e.g., U.S. Pat. No. 5,168,053; U.S. Pat. No. 5,190,931; U.S. Pat. No. 5,135,917, U.S. Pat. No. 5,087,617; see also, e.g., Clusel et al., 1993 *Nucl. Acids Res.* 21:3405-11, describing "dumbbell" antisense oligonucleotides). "Ribozyme" polynucleotides can be targeted to any RNA transcript and are capable of catalytically cleaving such transcripts, thus impairing translation of mRNA (see, e.g., U.S. Pat. No. 5,272,262; U.S. Pat. No. 5,144,019; and U.S. Pat. Nos. 5,168,053, 5,180,818, 5,116,742 and 5,093, 246; U.S. 2002/193579). "Triplex" DNA molecules refers to single DNA strands that bind duplex DNA to form a colinear triplex molecule, thereby preventing transcription (see. e.g., U.S. Pat. No. 5,176,996, describing methods for making synthetic oligonucleotides that bind to target sites on duplex DNA). Such triple-stranded structures are unstable and form only transiently under physiological conditions.

Because single-stranded polynucleotides do not readily diffuse into cells and are therefore susceptible to nuclease digestion, development of single-stranded DNA for antisense or triplex technologies often requires chemically modified nucleotides to improve stability and absorption by cells. siRNAs, by contrast, are readily taken up by intact cells, are effective at interfering with the expression of specific polypeptides at concentrations that are several orders of magnitude lower than those required for either antisense or ribozyme polynucleotides, and do not require the use of chemically modified nucleotides.

RNA-based therapeutic approaches using siRNA, ribozymes and anti-sense RNA have been shown to down-regulate specific gene expression in cancerous or viral-infected cells. RNA has therefore been particularly attractive as a therapeutic platform, since it can be manipulated with simplicity characteristic of DNA, while possessing non-canonical base-pairing, versatile function and catalytic activity similar to that of proteins. Typically, RNA molecules contain a large variety of single-stranded stem-loops for inter- and/or intra-molecular interactions. These loops can serve as mounting dovetails, and thus external linking dowels might not be needed in fabrication and assembly.

Although the concept of RNA nanotechnology has been developed for more than ten years, the popularity of studying RNA nanostructures has emerged recently, as reflected by the observation that 90% of publications on RNA nanostructures were published during or after 2006. For example, the DNA packaging motor of the double-stranded DNA (dsDNA) bacteriophage phi29 is geared by a hexameric packaging RNA (pRNA) ring. Each pRNA contains two functional domains. The central domain of each pRNA subunit contains two interlocking loops, denoted as the right- and left-hand loops that can be reengineered to form dimers, trimers, tetramer, pentamer, hexamers or heptamer via hand-in-hand interactions (FIG. 3). The helical DNA packaging domain is located at the 5'/3' paired ends. The two domains fold separately, and replacement of the helical domain with a siRNA (or with a ribozyme or an antisense RNA) does not affect pRNA structure, folding or intermolecular interactions. The resultant pRNA/siRNA chimera has been demonstrated to be useful for gene therapy. In addition, the 5'/3' paired helical region serves as a site for the binding of a DNA packaging enzyme gp16.

RNA is therefore a particularly attractive building block for bottom-up fabrication of nanostructures. In a number of described systems, self-assembled nanoparticles composed of multiple RNA building blocks have been used as vehicles to escort siRNA, ribozymes, antisense RNA or other therapeutics to specific cells.

One of the challenges in this emerging field, however, is the relative instability of RNA nanoparticles that are formed without covalent modifications or chemical cross-linking, resulting in their dissociation at ultra low concentrations in vivo in human and animal circulation systems. This instability has seriously hindered the delivery efficiency and therapeutic applications of RNA nanoparticles. In addition, magnesium is critical for RNA folding and the optimum concentration is in the range of tens of mM; however, under physiological conditions (e.g., in the circulation of humans and other mammals), the magnesium concentration is less than 1 mM. Such low magnesium concentrations could result in RNA misfolding, as well as dissociation of the RNA nanostructures. An obstacle to reliable and convenient systemic delivery of therapeutic RNA nanoparticles is thus their dissociation at low concentrations, along with misfolding or unfolding in the low-magnesium environment after entering the circulatory system in the body.

Clearly there remains a need in the art for improved compositions and methods for preparation and delivery of nanoparticles such as therapeutic RNA-based nanoparticles. The herein described invention embodiments address this need and provide other related advantages.

BRIEF SUMMARY

This disclosure provides a multivalent RNA junction scaffold. In most of the preferred embodiments, the multivalent RNA junction scaffold comprising multiple RNA oligomers that form a polymer complex, wherein the polymer complex is configured to promote an array of thermodynamically and stoichiometrically stable RNA nanoparticles.

In one preferred embodiment, the RNA oligomer in the multivalent RNA junction scaffold further comprises sequences for at least one biologically active moiety.

In some embodiments, the aforementioned polymer complex is formed by extending at least one interlocking loop of the RNA oligomer to form hand-in-hand assembly of the RNA nanoparticle.

In some embodiments the aforementioned polymer complex is formed by extending 3'-end of at least one RNA oligomer with selective palindrome sequence to form foot-to-foot assembly of said RNA nanoparticle.

In another preferred embodiment, the RNA oligomer formed polymer complex further comprises RNA branches with selective RNA or DNA sticky ends or palindrome sequences therein.

In some embodiments, the oligomers-formed polymer complex could be a trimer, a tetramer, a pentamer, a hexamer, a heptamer, or an octamer.

In some embodiments, the bioactive moiety attached to the RNA scaffold is heterogeneous.

In certain embodiments, at least one of the bioactive moieties attached to the RNA scaffold is selected from the SEQ. ID. NO: 1-14. Certain bioactive moieties are drugs, markers, fluorescent dyes, chemicals, siRNAs, ribozymes, riboswitches, or other functionalities. In some preferred embodiments, these bioactive moieties are used as therapeutics for treatment of cancers, viral infections, genetic diseases and other ailing. In other preferred embodiments, these bioactive moieties are used for detection or diagnosis of cancers, viral infections, genetic diseases and other ailing.

In certain embodiments, the multifunctional bioactive moiety is used as an RNA antibody for detection or diagnosis of cancers, viral infections, genetic diseases and other ailing. In other preferred embodiments, these bioactive moieties are promoted to be crystalline by the RNA scaffold.

In one of the embodiments the multiple RNA junction scaffold is a trifurcate junction domain comprising:
a. an $a_{3WJ}$ RNA polynucleotide;
b. a $b_{3WJ}$ RNA polynucleotide; and
c. a $c_{3WJ}$ RNA polynucleotide.

In another embodiment, the multiple RNA junction scaffold is an X-motif domain comprising:
a. an $a_{X-RNA}$ polynucleotide;
b. a $b_{X-RNA}$ polynucleotide;
c. a $c_{X-RNA}$ polynucleotide; and
d. a $d_{X-RNA}$ polynucleotide.

In a preferred embodiment, a trifurcate junction domain comprising at least:
  (i) an $a_{3WJ}$ RNA polynucleotide comprises the SEQ. ID. NO: 15 (5'-UUG CCA UGU GUA UGU GGG-3')
  (ii) a $b_{3WJ}$ RNA polynucleotide comprises the SEQ. ID. NO: 16 (5'-CCC ACA UAC UUU GUU GAU CC-3')
  (iii) a $c_{3WJ}$ RNA polynucleotide comprises the SEQ. ID. NO: 17 (5'-GGA UCA AUC AUG GCA A-3').

In another preferred embodiment, an X-motif domain comprising:
  a. an $a_{X-RNA}$ Polynucleotide comprises the SEQ. ID. NO: 18 (5'-UUG CCA UGU GUA UGU GGG UUC AG CAC-3')
  b. a $b_{X-RNA}$ polynucleotide comprising the SEQ. ID. NO: 19 (5'-GUG CUG GAA CUG ACU GC-3')
  c. a $c_{X-RNA}$ polynucleotide comprising the SEQ. ID. NO: 20 (5'-GCA GUC AGC CCA CAU ACU UUG UUG AUC C-3'); and
  d. a $d_{X-RNA}$ polynucleotide comprising SEQ. ID. NO: 21 (5'-GGA UCA AUC AUG GCA A-3').

In certain preferred embodiments, the trifurcate RNA junction domain comprising:
  a. a first helical region RNA polynucleotide comprising 8 RNA nucleotide base pairs, said RNA polynucleotide forms canonical Watson-Crick bonds;
  b. a second helical region RNA polynucleotide comprising (i) 9 RNA nucleotide base pairs, (ii) at least one impaired RNA nucleotide base that is situated between the first helical region and the second helical region, and (iii) 3 unpaired RNA nucleotides situated at a 3'end of said second helical region RNA polynucleotide; and
  c. a third helical region RNA polynucleotide comprising 8 RNA nucleotide base pairs which form canonical Watson-Crick bonds.

In certain embodiments, the trifurcate RNA junction domain comprising:
  a. a first helical region RNA polynucleotide comprising 6 RNA nucleotide base pairs which form canonical Watson-Crick bonds;
  b. a second helical region RNA polynucleotide comprising (i) 9 RNA nucleotide base pairs, (ii) at least one unpaired RNA nucleotide base that is situated between the first helical region and the second helical region, and (iii) 3 unpaired RNA nucleotides situated at a 3'end of said second helical region RNA polynucleotide; and
  c. a third helical region RNA polynucleotide comprising 6 RNA nucleotide base pairs which form canonical Watson-Crick bonds.

This disclosure further provides a multipartite RNA nanoparticle. The multipartite RNA nanoparticle contains an array of thermodynamically and stoichiometrically stable, multifunctional bioactive moiety crystal. The multipartite RNA nanoparticle is assembled by a multivalent RNA junction scaffold. The multivalent RNA junction scaffold is a multiple RNA oligomer-formed polymer complex.

In certain embodiment, the RNA crystalline structure is formed by bottom-up self-assembly.

In certain embodiment, the RNA junction scaffold's core is a polygon formed by the multiple RNA oligomers.

In certain embodiment, the RNA crystalline structure is further arranged by alternating the orientation of at least one RNA polynucleotide's neighboring molecule.

In certain embodiment, the RNA crystalline structure is further arranged to form 1D and 2D sheets by controlling the RNA polynucleotides' numbers in a given unit of the scaffold.

This disclosure further provides a method of making a multipartite RNA nanoparticle. The method comprises admixing in substantially equimolar amounts of RNA polynucleotides. The RNA polynucleotides contain a collection of pRNA junction domains to form a multivalent RNA junction scaffold and promote the assembly of an array of bioactive moiety into crystalline structure.

This disclosure further provides a method of delivering a biological active moiety to a cell. The method comprises contacting the cell with a multipartite RNA nanoparticle. The multipartite RNA nanoparticle is assembled by an RNA junction scaffold.

This disclosure further provides a method of delivering a therapeutic agent or a detectable labeling agent, or both. The method comprises administering to the subject a multipartite RNA nanoparticle. The multipartite RNA nanoparticle is assembled by an RNA junction scaffold.

In certain preferred embodiments, the aforementioned RNA junction scaffold is a multiple oligomer-formed polymer complex that further comprises RNA branches to attach certain therapeutic agent or detectable labeling agent, or both.

In certain preferred embodiments, the aforementioned oligomer-formed polymer complex further comprises RNA branches with selective RNA or DNA sticky ends or palindrome sequences therein.

In certain preferred embodiments, the aforementioned oligomer-formed complex is a trimer, a tetramer, a pentamer, a hexamer, a heptamer or an octamer.

This disclosure provides a method of using trifurcate or four way X-motif junction domain as a scaffold to produce stable multivalent RNA aptamers, the stable multivalent RNA aptamers recognize at least one given substrate. The method comprising:
  a. attaching a collection of random sequences to pRNA trifurcate or four way X-motif junction domain;
  b. selecting said random sequences to identify those that having high binding affinity to said substrate; and
  c. conjugating said identified aptamer or an otherwise available aptamer to pRNA trifurcate or four way X-motif junction domain, wherein said available aptamer mimics at least one antibody to said at least one substrate.

In certain preferred embodiment, the stable aptamer carries multivalent variants that recognize both cytotoxic T lymphocytes and different tumor cells.

In certain preferred embodiment, the given substrate is an antigen, a protein, or a cell surface marker.

In certain preferred embodiment, the identified aptamer provides advantages over traditional antibody fragments.

In some of preferred embodiments, the trifurcate junction domain is used for therapeutic delivery, diagnosis of diseases, promotion of RNA crystallization, and creation of stable RNA aptamer to mimic a given antibody.

In some of preferred embodiments, the trifurcate junction domain includes the trifurcate junction domain of DNA packaging RNA from other phi29 family members, such as phages PZA, phi15, BS32, B103, Nf, M2Y and GA-1. These trifurcate junction domains are used for therapeutic delivery, diagnosis of diseases, promotion of RNA crystallization, or creation of stable RNA aptamer to mimic a given antibody.

In certain preferred embodiments, the trifurcate junction domain includes but is not limited to the followings: pRNA, 5s rRNA, HCV, Alu SRP, Hammerhead ribozyme, 16s H34-H35-H38, 23s H75-H76-H79, 23s H83-H84-H85, G-Riboswitch (Type I), TPP Riboswitch (Type II), and M-box Riboswitch (Type II), wherein said trifurcate junction domain is used for therapeutic delivery, diagnosis of diseases, promotion of RNA crystallization, or creation of stable RNA aptamer to mimic a given antibody.

In certain preferred embodiments, the trifurcate junction domain is selected from the followings:

Family A: rRNA (16S H20-21-22; 16S H22-23-23a; 16S H25-25-26a; 16S H34-35-38; 23S H3-4-23; 23S H5H6H7; 23S H48-X-60; 23S H49-59.1-X; 23S H75-76-79; 23S H99-100-101).

Family B: rRNA (16S H28-29-43; 16S H32-33-34; 16S H33-33a-33b; 23S H33-34-35; 23S H49-50-51; 23S H83-84-85).

Family C: rRNA (16S H4-5-15; 16S H30-31-32; 16S H35-36-37; 16S H38-39-40; 23S H2-3-24; 23S H18-19-20; 23S H32-33-35; 23S H90-91-92); L11 rRNA; 5S rRNA; Alu domain; S domain; HH; G-riboswitch; P4P6; Twort Intron; S-dom RNaseP B-typ Unclassified family: Packaging RNA from: phi29; B103; SF5; and MN/NF phages.

In certain embodiments, the four way junction X-motif is selected from the followings:

Family H: 1U9S_78 Ribonuclease P_A; 2A2E_70 Ribonuclease P_A; 1NBS_89 Ribonuclease P_B; 2A64_90 Ribonuclease P_B; 1M50_13 Hairpin ribozyme; 1S72_1827 23S rRNA; 2AW4_1771 23S rRNA; 2J01_1771 23S rRNA.

Family cH: 1KH6_4 HCV IRES; 2AVY_141 16S rRNA; 2J00_141 16S rRNA; 1NKW_2621 23S rRNA; 1S72_2678 23S rRNA; 2AW4_2642 23S rRNA; 2J01_2642 23S rRNA; 3F2Q_7 Riboswitch (FMN); 3F2Q_31 Riboswitch (FMN); 1NKW_1457 23S rRNA; 2AW4_1443 23S rRNA.

Family cL: 2AVY_568 16S rRNA; 2J00_568 16S rRNA; 1NKW_1282 23S rRNA; 1S72_1373 23S rRNA; 2AW4_1269 23S rRNA; 2J01_1269 23S rRNA; 1EFW_6 Transfer RNA; 1EHZ_6 Transfer RNA; 1N78_506 Transfer RNA; 1QRS_6 Transfer RNA; 1U08_6 Transfer RNA; 2GIS_7 Riboswitch (SAM I).

Family cK: 2AVY_114 16S rRNA; 2J00_114 16S rRNA; 1NKW_2263 23S rRNA; 1S72_2318 23S rRNA; 2AW4_2284 23S rRNA; 2J01_2284 23S rRNA; 1NKW_1360 23S rRNA; 1S72_1452 23S rRNA; 2AW4_1346 23S rRNA; 2J01_1347 23S rRNA; 2AVY_18 16S rRNA; 2J00_18 16S rRNA.

Family π: 1U9S_118 Ribonuclease P_A; 2A2E_110 Ribonuclease P_A.

Family cW: 1NKW_1682 23S rRNA; 1S72_1743 23S rRNA; 2AW4_1665 23S rRNA; 2J01 1665 23S rRNA.

Family ψ: 1S72_42 23S rRNA; 1NKW_1824 23S rRNA; 1S72_1888 23S rRNA; 2AW4_1832 23S rRNA; 2J01_1832 23S rRNA; 1NKW_244 23S rRNA; 2AW4_267 23S rRNA.

Family X: 1NKW_608 23S rRNA; 2AW4_600 23S rRNA; 2J01_600 23S rRNA.

Family cX: 2IHX_166 Sarcoma virus; 2AVY_942 16S rRNA; 2J00_940 16S rRNA.

These and other aspects of the present invention will become apparent upon reference to the following detailed description and attached drawings. All references disclosed herein are hereby incorporated by reference in their entirety as if each was incorporated individually.

BRIEF DESCRIPTION OF THE SEVERAL VIEWS OF THE DRAWINGS

FIG. 6. The branched pRNA nanoparticles. (A) pRNA 3WJ motif. (B) pRNA 3WJ derived X-shaped pRNA motif. (C) The assembled branched pRNA nanostructures based on pRNA 3WJ and X-shaped motif.

FIG. 8. AFM images for different kinds of pRNA nanoparticles. (A) pRNA trimer; (B) pRNA tetramer; (C) pRNA pentamer; (D) pRNA hexamer; (E) pRNA heptamer.

Figure 13:
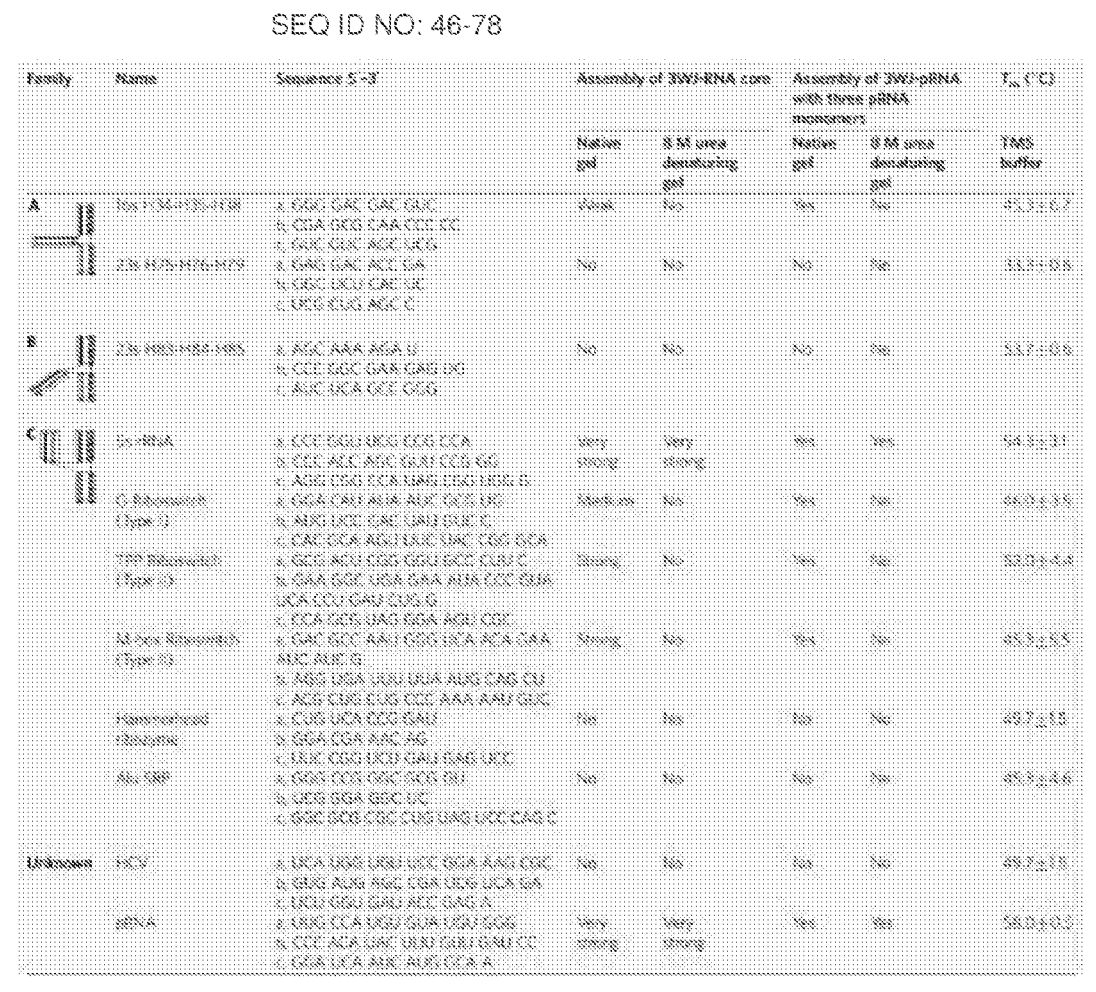

FIG. 13. Comparison of biophysical properties of various 3WJ cores.

FIG. 14. Comparison of assembly and stability of the other 14 3WJ cores that was not practical for thorough investigations.

FIG. 31 shows exemplary three-way junction (3WJ) structures (boxes) in packaging RNAs (pRNA).

FIG. 41. Assembly and stability of the pRNA-X core. In the table, '+' indicates the presence of the RNA oligo in samples of the corresponding lanes. (A) 15% native PAGE and 8M denaturing PAGE gels showing the step-wise assembly of the pRNA-X core. (B) Melting curves for the individual pRNA-X strands (orange, red, blue, and black) and the pRNA-X core (green).

FIG. 42. Construction of tetravalent pRNA-X nanoparticles harboring monomeric pRNA at each branch. (A) Schematic of pRNA-X-4pRNA constructs, (B) corresponding AFM images, (C) 8% native (upper) and denaturing (lower) PAGE gel, (D) Dissociation assay for the pRNA-X-4pRNA constructs by 4-fold serial dilution with [$^{32}$P] pRNA-X-4pRNA (lanes 1-9) from 100 nM-1 pM. Arrow indicates the lowest detectable concentration of 25 pM. Scale bar: 50 nm.

FIG. 43. Construction of multi-module RNA nanoparticles harboring MG (malachite green) aptamer, Folate, Luciferase siRNA, and Survivin siRNA. (A) Schematic and sequences of the tetravalent pRNA-X constructs. (B) Step-wise assembly of RNA nanoparticles using the pRNA-X as scaffold with functionalities assayed by 8% denaturing PAGE. (C) Functional assay of the MG aptamer incorporated in pRNA-X nanoparticles. MG fluorescence was measured using excitation wavelengths 475 and 615 nm. (D) Target Gene Knockdown effects of Survivin siRNA showed by RT-PCR (GADPH is the endogenous control) on mRNA level and Western Blot assay (β-actin bands served as loading control) on protein level. (E) Dual-luciferase assay for target gene knock-down of luciferase gene. The relative firefly luciferase activity reflects the level of luciferase gene expression and is obtained by normalizing firefly luciferase activity using the internal control renilla luciferase activity. Error bars represent s.d. (N=3).

FIG. 44. Binding and entry of tetravalent pRNA-X nanoparticles into targeted cells. (A) Flow cytometry revealed that [pRNA-X/MG/FA/siLuci/si/Surv] nanoparticles bound and specifically entered cells. Positive and negative controls were Cy3-FA-DNA and Cy3[pRNA-X/MG/NH$_2$/siLuci/si/Surv] (without FA), respectively. (B) Confocal images showed targeting of Folate positive (FA+) KB cancer cells by the co-localization (overlap, 4) of cytoplasm (green, 1) and fluorescent RNA nanoparticles (red, 2) (magnified, right panel). Blue represents nuclei, 3.

FIG. 45. Construction of tetravalent pRNA-X nanoparticles harboring multiple siRNA for enhanced gene silencing effects. (A) Sequences and notations of siRNA used in tetravalent constructs. Blue: siLuci-1 and 1'; Red: siLuci-2 and 2'; Green: siLuci-3 and 3'; Orange: siLuci-4 and 4'; Black: Control siRNA. (B-C) Quantification of Luciferase gene expression: Effects of increasing number of different Luciferase siRNAs (siLuci-1, 2, 3 and 4) (A); and four identical siRNA constructs (siLuci-1, 2, 3 or 4) incorporated in the pRNA-X motif (B). RLU: Relative Luciferase Units; siLuci-1', 2' 3' and 4' represent reversed siRNA sequences for siLuci-1, 2, 3 and 4 respectively. Error bars represent s.d. (N=3).

FIG. 48. Design of sticky ends or palindrome sequence for inter-DNA and RNA interactions.

FIG. 51. (A) Assay for binding affinity after 6th round RNA SELEX showing great enhancement comparing with 1st round RNA and (B) and (C) Preparation of FITC-EpCAM RNA aptamer library for cell binding test.

FIG. 52. (A) EpCAM binding and internalization of RNA nanoparticles containing the RNA aptamers from screening. (a) Cells were fixed and stained with the EpCAM antibody and visualized using the Alexa 488-conjugated secondary antibody as positive control. (b) EpCAM-pRNA nanoparticles (200 nM) labeled with Cy3 were incubated with HT29 cells for 24 h, fixed and imaged using confocal microscopy. Note the appearance of Cy3 signals in the cytoplasm of cells; the insert shows the enlarged image of a single cell. (Nuclei were labeled with DAPI.). (B) EpCAM binding and internalization. (a) EpCAM-pRNA (40 nM) labeled with Cy3 were incubated with HT29 cells for 4 h in serum-free media and imaged using confocal microscopy. Note the appearance of Cy3 signals representing RNA nanoparticles in the cytoplasm and nucleus of cells. (b) Enlarged image (5×) of a cells after EpCAM-pRNA treatment in serum free media. (C) Binding and internalization of RNA particles containing 2'-F modified stable EpCAM RNA aptamer. FITC labeled 2'-F EpCAM-pRNA (40 nM) were incubated with HT29 cells for 4 h in serum free media and imaged using confocal microscopy. 2'-F aptamer was screened from SELEX earlier round (a-b), and later round (c-e). (D) Schematic of Bispecific (a-b) and trispecific (c) 3WJ based aptamer platform. (a) using a single 3WJ scaffold (see Part IB). ( ) Using two 3WJ scaffolds linked by a sequence; (c) Hexamer constructs using three 3WJ scaffolds linked by a 3WJ core. The aptamers will be selected via modified nanotechnology-based SELEX approaches. The polyvalent nature of the RNA scaffolds will bring multiple targets together. Specific examples include, but not limited to, linking a T-cell with a tumor cell, targeting two antigens on a single tumor cell; target cytokines for inflammatory diseases or angiogenic factors for solid tumors.

FIG. 53 designates Table 1. Sequence of loop extended pRNA homo-dimers and hetero-monomers.

FIG. 54 designates Table 2. Sequence of branched pRNA nanostructures.

FIG. 55 designates Table 3. Sequence of inserted functional moieties.

Figure 1:
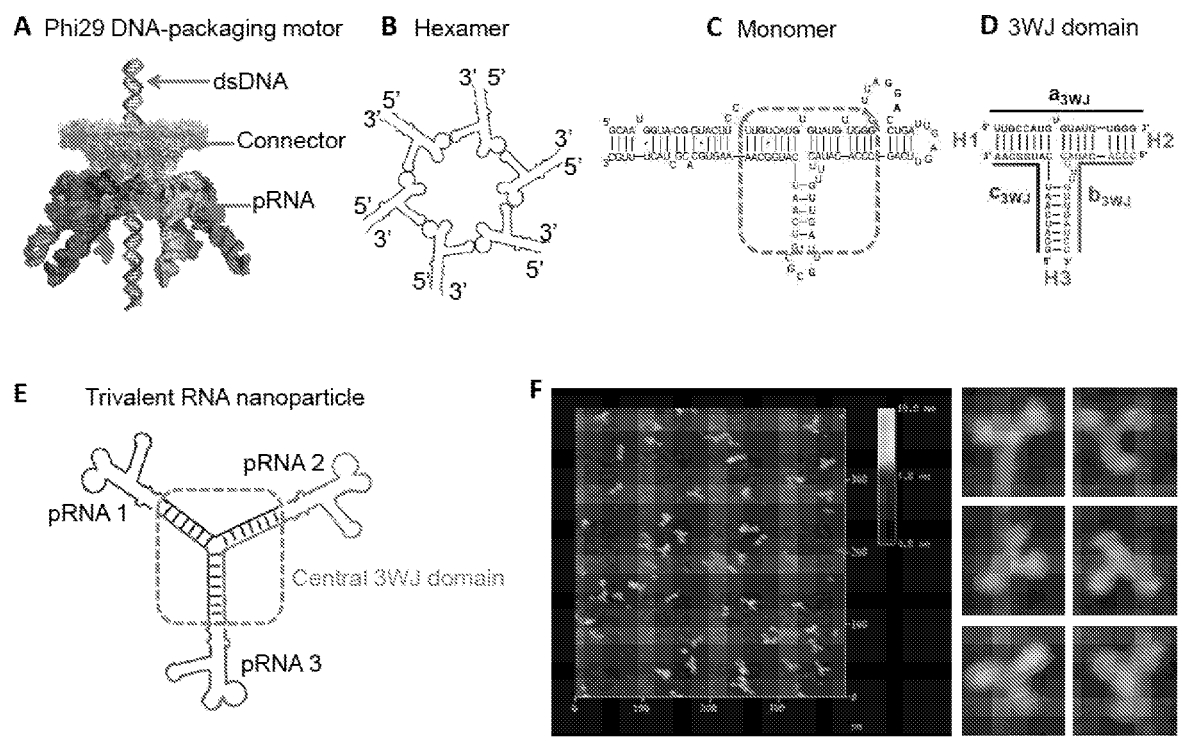
FIG. 1: Sequence and secondary structure of phi29 DNA-packaging RNA (pRNA). (A) Illustration of the phi29 packaging motor geared by six pRNAs (cyan, purple, green, pink, blue and orange structures). (B) Schematic showing a pRNA hexamer assembled through hand-in-hand interactions of six pRNA monomers. (C) Sequence of pRNA monomer Ab'. Green box: central 3WJ domain. In pRNA Ab', A and b' represent right- and left-hand loops, respectively. (D) 3WJ domain composed of three RNA oligomers in black, red and blue. Helical segments are represented as H1, H2, H3. (E), (F) A trivalent RNA nanoparticle consisting of three pRNA molecules bound at the 3WJ-pRNA core sequence (black, red and blue) (E) and its accompanying AFM images.

Alternatively, Applicant respectfully requests these tables be printed at the end of the specification.

BRIEF DESCRIPTION OF SEQUENCES

SEQ. ID. NO: 1: folate-DNA strand (5' folate-CTC CCG GCC GCC ATG GCC GCG GGA TT 3'),
SEQ. ID. NO: 2: Survivin siRNA antisense strand (5' UGA CAG AUA AGG AAC CUG CUU 3'),
SEQ. ID. NO: 3: scramble control of Survivin siRNA antisense strand (5' AUA GUG GGA CCA AUC AAG CUU 3'),
SEQ. ID. NO: 4: MG binding aptamer –1 (5' GGA UCC CGA CUG GCG AGA GCC AGG UAA CGA AUG GAU CC 3'),
SEQ. ID. NO: 5: MG binding aptamer –2 strand 1 (5' AUG GUA ACG AAU GA 3'),
SEQ. ID. NO: 6: MG binding aptamer –2 strand 2 (5' CAA UCC GAC AU 3'),
SEQ. ID. NO: 7: STV binding aptamer (5' CGA CCA GAA UCA UGC AAG UGC GUA AGA UAG UCG CGG GUC G 3'),
SEQ. ID. NO: 8: working HBV ribozyme (5' CAA AUU CUU UAC UGA UGA GUC CGU GAG GAC GAA ACG GGU C 3'),
SEQ. ID. NO: 9: disabled HBV ribozyme (5' CAA AUU CUU UAC UAA UGA GUC CGU GAG GAC GAA ACG GGU C 3'),
SEQ. ID. NO: 10: firefly Luciferase siRNA 1 antisense strand (5' GUU GGC ACC AGC AGC GCA C 3'),
SEQ. ID. NO: 11: firefly Luciferase siRNA 2 antisense strand (5' UCG AAG UAC UCA GCG UAA G 3'),
SEQ. ID. NO: 12: firefly Luciferase siRNA 3 antisense strand (5' GCC CAU AUC GUU UCA UAG C 3'),
SEQ. ID. NO: 13: firefly Luciferase siRNA 4 antisense strand (5' GUA GAU GAG AUG UGA CGA A 3'),
SEQ. ID. NO: 14: scramble control of firefly Luciferase siRNA antisense strand (5'GUC GGU UUC GUG AAG GAGA 3').
SEQ. ID. NO: 15 an $a_{3WJ}$ RNA polynucleotide (5'-UUG CCA UGU GUA UGU GGG-3');
SEQ. ID. NO: 16 a $b_{3WJ}$ RNA polynucleotide (5'-CCC ACA UAC UUU GUU GAU CC-3')
SEQ. ID. NO: 17 a $c_{3WJ}$ RNA polynucleotide (5'-GGA UCA AUC AUG GCA A-3').
SEQ. ID. NO: 18 an $a_{X-RNA}$ polynucleotide (5'-UUG CCA UGU GUA UGU GGG UUC CAG CAC-3')
SEQ. ID. NO: 19 a $b_{X-RNA}$ polynucleotide (5'-GUG CUG GAA CUG ACU GC-3')
SEQ. ID. NO: 20 a $c_{X-RNA}$ polynucleotide (5'-GCA GUC AGC CCA CAU ACU UUG UUG AUC C-3');
SEQ. ID. NO: 21 a $d_{X-RNA}$ polynucleotide (5'-GGA UCA AUC AUG GCA A-3').
SEQ. ID. NO: 22: GAPDH left: 5'-AGCCACATCGCTCAGACAC-3';
SEQ. ID. NO: 23: GAPDH right: 5'-GCCCAATACGACCAAATCC-3';
SEQ. ID. NO: 24: Survivin left: 5'-CACCGCATCTCTACATTCAAGA-3';
SEQ. ID. NO: 25: Survivin right: 5'-CAAGTCTGGCTCGTTCTCAGT-3'
SEQ. ID. NO: 26: 7Ba' pRNA with 3'-end palindrome sequences 5'GGAAUGGUACGGUACUUCCAUUGU-CAUGUGUAUGUUGGGGAUUAACAGGC ACUGA-UUGAGUUCAGCCCACAUACUUUGUUGA-UUGUCCACUGUCAAUCAUG GCAAAAGUGCACGCUACUUUCC CGAUCG 3'.
SEQ ID NO: 27: Sequence of pRNA monomer Ab' (FIG. 1C)
SEQ ID NO: 28-41 (Table under Table 2C) loop extension sequences (28-34 for right hand loops and 35-41 for left hand loops)
SEQ ID NO: 42 Sequence for $a_{3wj}$ (del U) UUGCCAUG-GUAUGUGGG (5'-3')
SEQ ID NO: 43 Sequence for b3wj (del UUU) CCAA-CAUACGUUGAUCC (5'-3')
SEQ ID NO: 44 Sequence for b3wj (del 4-nt) AACAUACU-UUGUUGAU (5'-3')
SEQ ID NO: 45 Sequence for c3wj (del 4-nt) AUCAAU-CAGUGC (5'-3')

SEQ ID NO: 46-48 Sequences for 16s RNA H34-H35-H38 3wj core
SEQ ID NO: 49-51 Sequences for 23S RNA H75-H76-H79 3wj core
SEQ ID NO: 52-54 Sequences for 23S RNA H83-H84-H85 3WJ CORE
SEQ ID NO: 55-57 sequences for 5s rRNA 3wj core
SEQ ID NO: 58-60 sequences for G-Riboswitch (type I) 3wj core
SEQ ID NO: 61-63 Sequences for TPP riboswitch (type II) 3wj core
SEQ ID NO: 64-66 sequences for M-box Riboswitch (type II) 3wj core
SEQ ID NO: 67-69 sequences for Hammerhead ribozyme 3wj core
SEQ ID NO:70-72 sequences for Alu SRP 3wj core
SEQ ID NO:73-75 sequences for HCV 3wj core
SEQ ID NO: 76-78 sequences for pRNA 3wj core
SEQ ID NO: 79-120 sequences for another 14 different 3wj cores not thoroughly investigated.
SEQ ID NO: 121 41nt RNA
SEQ ID NO:122 5' Primer for 41nt RNA
SEQ ID NO:123 3' Primer for 41nt RNA
SEQ ID NO:124 106nt RNA harboring HBV ribozyme
SEQ ID NO:125 DNA template for 106nt RNA harboring HBV ribozyme
SEQ ID NO:126 5' primer for 106nt RNA harboring HBV ribozyme
SEQ ID NO:127-128 3' primers for 106nt RNA harboring HBV ribozyme
SEQ ID NO: 129 106nt RNA harboring disabled HBV ribozyme
SEQ ID NO:130 DNA template for 106nt RNA harboring disabled HBV ribozyme
SEQ ID NO: 131 5' primer for 106nt RNA harboring disabled HBV ribozyme
SEQ ID NO: 132-133 3' primers for 106nt RNA harboring disabled HBV ribozyme
SEQ ID NO: 134 96nt RNA harboring MG binding aptamers
SEQ ID NO: 135 DNA template for 96nt RNA harboring MG binding aptamers
SEQ ID NO:136 5' primer for 96nt RNA harboring MG binding aptamers
SEQ ID NO: 137-138 3' primers for 96nt RNA harboring MG binding aptamers
SEQ ID NO: 139-147 Sequences for 5' loop of 7Aa'-7Ii' in FIG. 38A Table
SEQ ID NO: 148-156 Sequences for 3' loop of 7Aa'-7Ii' in FIG. 38A Table
SEQ ID NO: 157 Sequence for Luciferase-1 siRNA
SEQ ID NO: 158 Sequence for Luciferase-2 siRNA
SEQ ID NO: 159 Sequence for Luciferase-3 siRNA
SEQ ID NO: 160 Sequence for Luciferase-4 siRNA
SEQ ID NO: 161 Sequence for Scramble siRNA
SEQ ID NO: 162-170 Sequences for loop extended pRNA homo-dimers 7Aa' to 7Ii' in Table 1
SEQ ID NO: 171-182 sequences for loop extended pRNA hetero-dimers 7Ba' to 7Ag' in Table 1
SEQ ID NO: 183 Foot to Foot hexamer dx-RNA+PS6 in Table 2
SEQ ID NO: 184 in Table 2, 3wj-based branched hexamer a3WJ$_{FWD}$+a3WJ$_{REV}$
SEQ ID NO: 185 in Table 2, 3wj-based branched hexamer a3WJ$_{FWD}$+b3WJ$_{REV}$
SEQ ID NO: 186 in Table 2, 3wj-based branched hexamer a3WJ$_{FWD}$+c3WJ$_{REV}$

DETAILED DESCRIPTION

Disclosed herein for the first time are the unexpected findings that RNA loops, cores, motifs and palindromes derived from the pRNA of bacteriophage Phi29 DNA packaging motor are gathered in a tool kit and used for fabrication of RNA dimers, trimers, tetramers, pentamers, hexamers, haptamers, octamers and other branched diversity architectures via hand-in-hand, foot-to-foot and arm-on-arm interactions. These novel RNA nanostructures further harbor drugs, ligands, siRNAs, fluorescent markers, ribozymes, RNA aptamers or miRNA for detection, purification, trafficking, delivery, and therapy. These novel RNA nanostructures can also be used to mimic antibody and promote RNA crystallization. Incorporation of these functionality was achieved prior to but not subsequent to the assembly of the RNA nanoparticles, thus ensure the production of homogenous therapeutic nanoparticles. The versatility demonstrated by one biological RNA molecule implies an unparalleled potential concealed within the RNA nanotechnology field.

RNA is a polynucleotide acid that possesses all favorable multimeric nature of conventional polymers, while differently and desirable, RNA nanoparticles can be constructed using a bottom-up approach in a controlled and predictable manner to generate nanoparticles with defined structure and stoichiometry.

Figure 3:
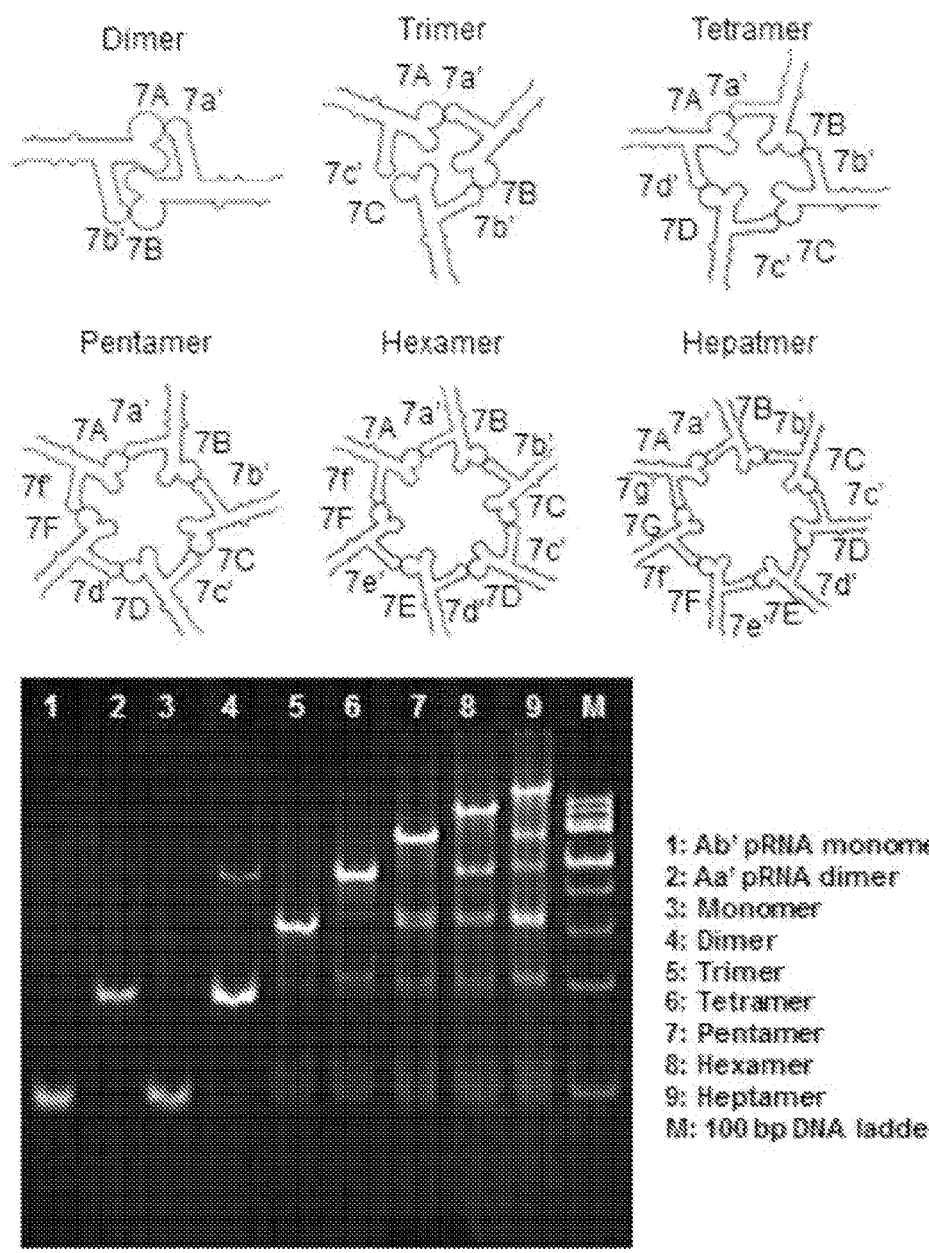
FIG. 3. The assembly of pRNA nanoparticles based on reengineered hand-in-hand interaction. 1: Wild-type pRNA Ab' monomer; 2: Wild-type pRNA Aa' dimer; 3: loop extended pRNA monomer; 4: loop extended pRNA dimer: 5: loop extended pRNA trimer; 6: loop extended pRNA tetramer; 7: loop extended pRNA pentamer; 8: loop extended pRNA hexamer; 9: loop extended pRNA heptamer; 10: 100 bp DNA ladder.

Research in nanotechnology involves modification, engineering, and/or assembly of organized materials from the bottom, besides the top-down approach, on the nanometer scale. Concerning the utility in nanotechnology, RNA is versatile in structure and function or even possesses enzymatic activity characteristic to proteins, which can be designed, predicted and manipulated at a level of simplicity similar to DNA. Holding the advantages of two worlds, RNAs are ideal materials for nanotechnological applications.

pRNA is one crucial component of bacteriophage phi29 DNA packaging motor (FIG. 1A). Each pRNA contains two functional domains. The helical DNA packaging domain is located at the 5'/3' paired ends. The central domain of each pRNA subunit (bases 23-97) embrace two interlocking loops denoted as the right- and left-hand loops for intermolecular interaction (FIG. 1C). The two domains fold separately, and replacement of the helical domain with a siRNA does not affect pRNA structure, folding or intermolecular interactions. Two interlocking loops can be reengineered to form dimers, trimers, tetramer, pentamer, hexamer or haptamers via hand-in-hand interactions (FIG. 3). In addition, the two domains are connected by a three-way junction (3WJ) motif (FIG. 1D).

In this disclosure we have demonstrated using the unique structure of pRNA and its interlocking loops extension, coupled with creative design of 3'end palindrome sequences to facilitate crystallization of RNA molecules and their associated biologic active moieties. The pRNA structure and its modification described herein enables 3WJ motif and its derivatives to fulfill the novel functions of pRNA.

Particularly, the disclosure overcomes the obstacle of template dependent forming a higher ordered pRNA polyvalent nanoparticle. For example, the pRNA hexamer assembly requires procapsid, a large protein complex of bacteriophage 29, to serve as the template scaffold for assembly. This presents difficulty in the art. Assembly of dimers and trimers have been reported, however the low affinity of loop/loop interaction leads to the dissociation when delivered in vivo. Many years of attempt to assemble pRNAs multimers free of protein with oligomerization number larger than three have not been successful due to such low affinity.

Figure 7:
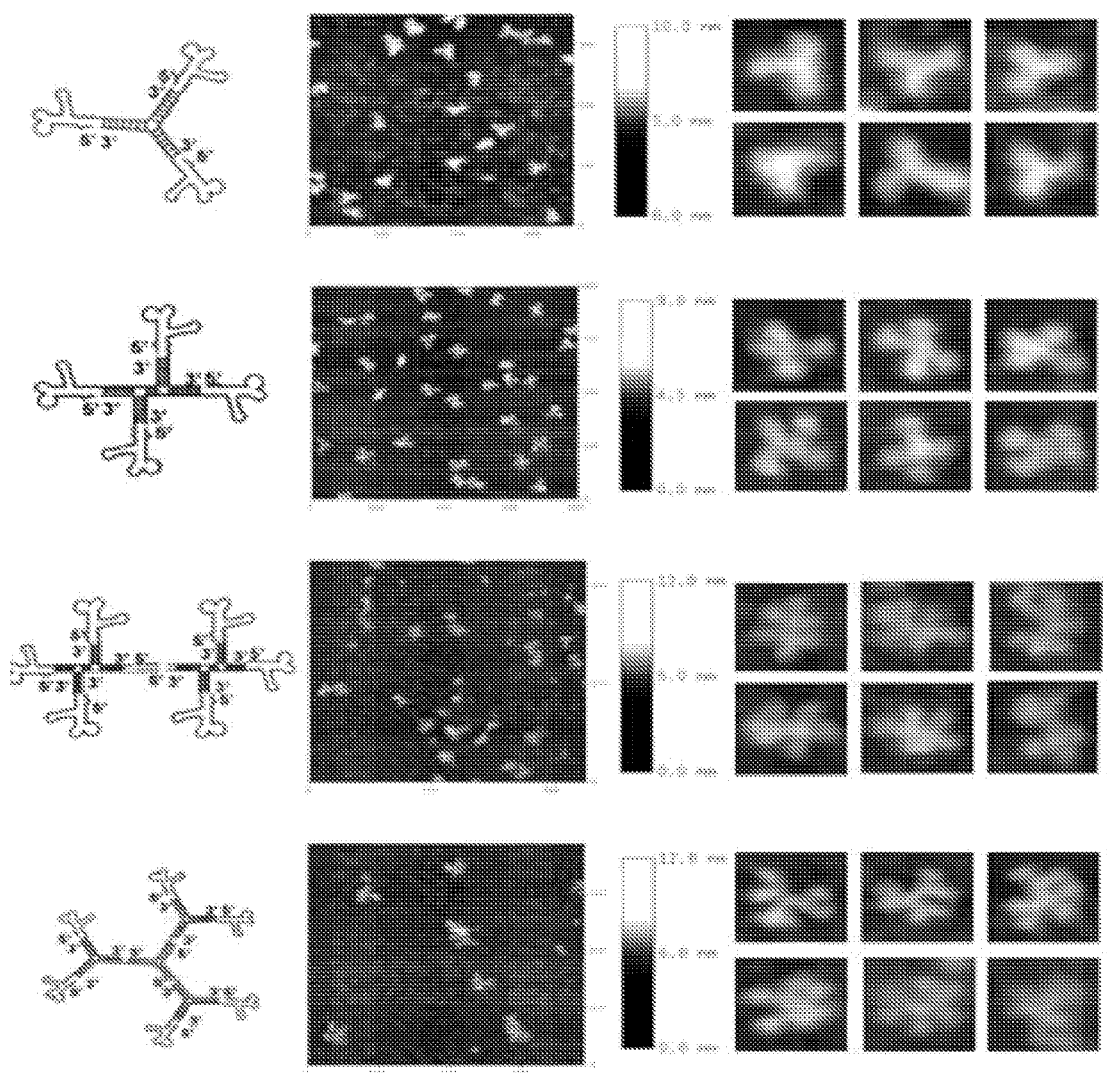
FIG. 7 AFM images for different kinds of branched pRNA nanoparticles.

Here we extend pRNA loop sequences from 4-nt interlocking interaction to 7-nt interlocking interaction (FIG. 2C) to construct varieties of novel pRNA nanoparticles such as tetramer, pentamer, hexamer, heptamer and octamer without template support. This disclosure details the construction of 3WJ, X-shaped motif as a scaffold to assembly RNA nanoparticles. With no limiting on the scope of use, such constructions are further extended to 5 way, 6 way, 7 way and 8 way motifs, etc (FIGS. 6 and 7).

Figure 4:
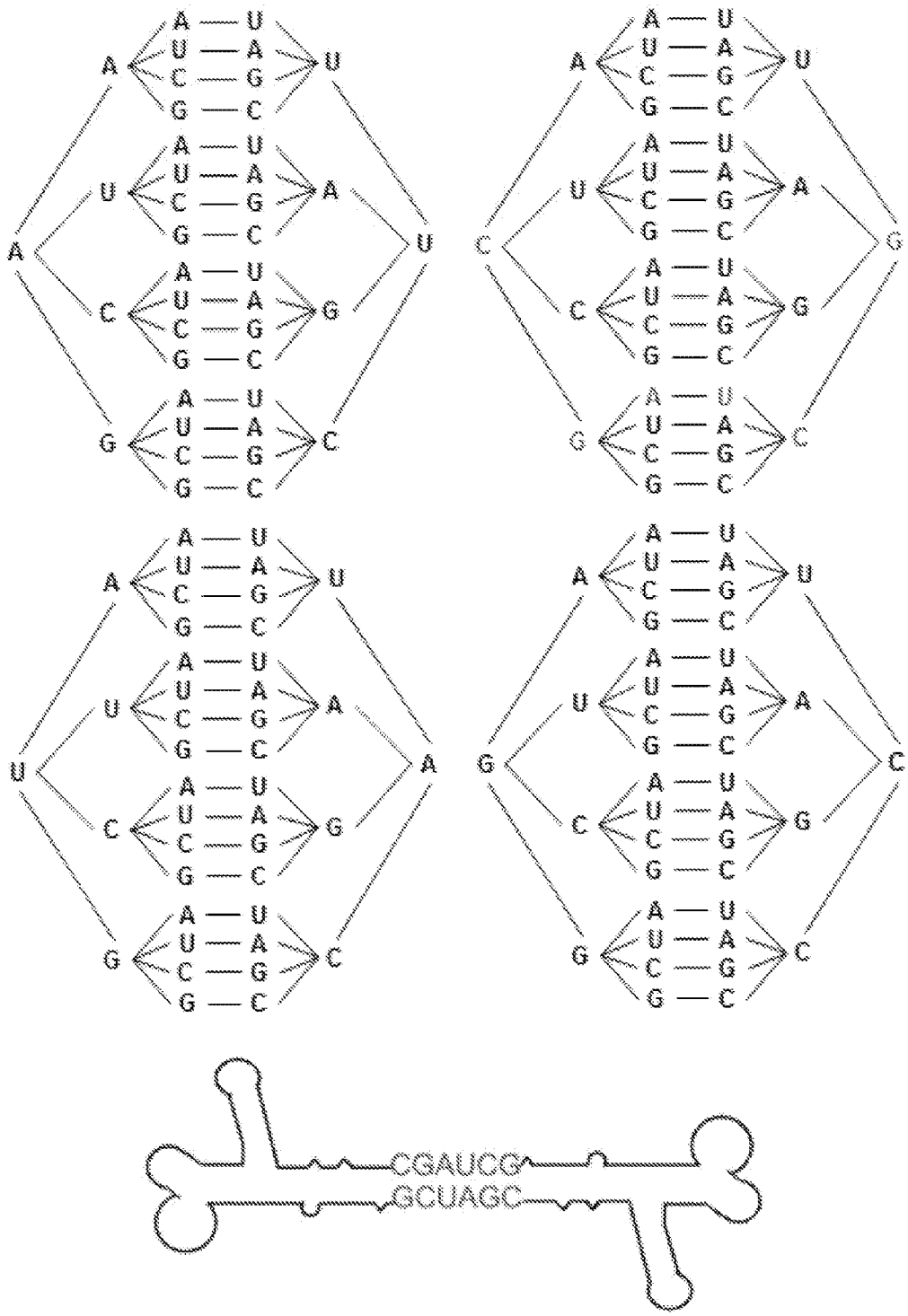
FIG. 4. Design of 6-nt palindrome sequence and formation of foot-to-foot dimer subunits for assembly of pRNA foot-to-foot nanoparticles.

In addition, introducing of palindrome sequence in the 3'-end of the pRNA (FIG. 4) also promoted the formation of novel foot-to-foot pRNA nanostructures.

The resulting complex is incredibly stable and resistant to denaturation even in presence of 8M urea. These toolkits are very useful to construct higher ordered diverse nanostructures with multiple functionalities as multivalent delivery system for nanotechnology and nanomedicine applications.

Construction of hexameric RNA nanoparticles with therapeutic functionalities have been reported by conjugation subsequent to the assembly of the RNA nanoparticles. Here we report the incorporation of all functionality prior but not subsequent to the assembly of the RNA nanoparticles, thus ensure the production of homogeneous therapeutic nanoparticles for medical application to ensure appropriate quality control.

There are many types of RNA molecules that could potentially be utilized for nanotechnology-based therapy such as small interfering RNAs, ribozymes, RNA aptamers, riboswitches, and miRNAs. Although the methods for gene silencing with high efficacy and specificity have been achieved in vitro, the effective delivery of RNA to specific cells in vivo remains challenging. The development of safe, efficient, specific and nonpathogenic nanodevices for the delivery of multiple therapeutic RNAs is in high demand. RNA nanotechnology holds great potential in this regard: (1) Homogeneous RNA nanoparticles can be manufactured with high reproducibility and known stoichiometry, thus avoiding unpredictable side effects or nonspecific toxicity associated with heterogeneous structures. (2) Using the bottom up approach, RNA nanoparticles can be assembled harboring multiple therapeutic, reporter and/or targeting payloads for synergetic effects. (3) Cell type-specific gene targeting can be achieved via simultaneous delivery and detection modules which reduces off-target toxicity and lowers the concentration of the drug administered, thus reducing the side effects of the therapeutics. (4) RNA nanoparticle size typically ranges from 10-50 nm, an optimal size for a non-viral vector as they are large enough to be retained by the body yet small enough to pass through the cell membrane via the cell surface receptors mediated endocytosis. The advantageous size has the potential to greatly improve the pharmacokinetics, pharmacodynamics, biodistribution, and toxicology profiles by avoiding non-specific cell penetration. (5) Protein-free RNA nanoparticles with RNA aptamers as anti-receptors can yield superior specificity compared to protein anti-receptors while displaying lowest antibody-inducing activity, thus providing an opportunity for repeated administration and treatment of chronic diseases. (6) RNA nanoparticles are treated as chemical drugs rather than biological entities, which will facilitate FDA approval.

However, one of the challenges in this emerging field of RNA nanotechnology is the relative instability without covalent modifications or cross-linking of the nanoparticles, resulting in the dissociation at ultra-low concentrations in vivo after systemic injection. This has seriously hindered the delivery efficiency and therapeutic applications of RNA nanoparticles.

The feasibility of RNA nanotechnology in disease therapy has been exemplified in the phi29 pRNA therapeutic system. The DNA packaging motor of bacteriophage phi29 (FIG. 1A) is geared by a hexameric pRNA ring, which contains two functional domains. The central domain of each pRNA subunit contains two interlocking loops, denoted as the right- and left-hand loops (FIG. 2B) that can be reengineered to form dimers or trimers via hand-in-hand interactions. The helical DNA packaging domain is located at the 5'/3' paired ends. The two domains are connected by a three-way junction (3WJ) region.

The trifurcate domain of the pRNA of bacteriophage phi29 DNA packaging motor can be assembled from three pieces of small RNA oligonucleotides ("oligos") with unusually stable properties. Two of the oligos were resistant to staining by reagents routinely used to stain RNA oligos. Self-assembled RNA nanoparticles with three or six pieces of RNA guided by the trifurcate domain were resistant to 10 M urea denaturation and remained undissociable at extremely low concentrations. In addition, magnesium was not required for nanoparticle assembly.

The branched RNA nanoparticles, with each arm fused to a cell receptor-binding ligand, aptamer, siRNA or ribozyme, were constructed with this trifurcate domain and assembled into homologous tri-stars, as demonstrated by atomic force microscopy (AFM) imaging. All modules within the nanostructure exhibited independent functionalities for specific cell binding, cell entry, gene silencing, catalytic function, and cancer targeting, both in vitro and in animal trials. The tri-stars were unusually stable and undissociable in vivo and were resistant to degradation by serum after chemical modifications.

As described herein, trifurcate RNA junction domains can be assembled from one, two or three RNA fragments. Compositions comprising the assembled trifurcate RNA junction domain, including RNA nanoparticles in which the RNA fragments further comprise one or more of an siRNA, a drug, a ribozyme, an RNA aptamer, a riboswitch, a targeting moiety (e.g., a folate moiety), a marker or detectable label moiety, a fluorescent dye, a chemical modification (e.g., a modified nucleotide that resists degradation such as a 2'-fluoro-modified RNA nucleotide), or another chemical moiety having a desired function, can be assembled from one, two or three components. In certain preferred embodiments, such assemblies are highly stable and do not dissociate following injection into the circulatory system of a human or animal. Surprisingly, the herein described trifurcate RNA junction domain, and RNA nanoparticles generated therefrom, can be stably assembled in the absence of magnesium, and exhibit stability without dissociating over a clinically relevant timeframe in low-magnesium environments such as a human or other mammalian circulatory system.

Figure 40:
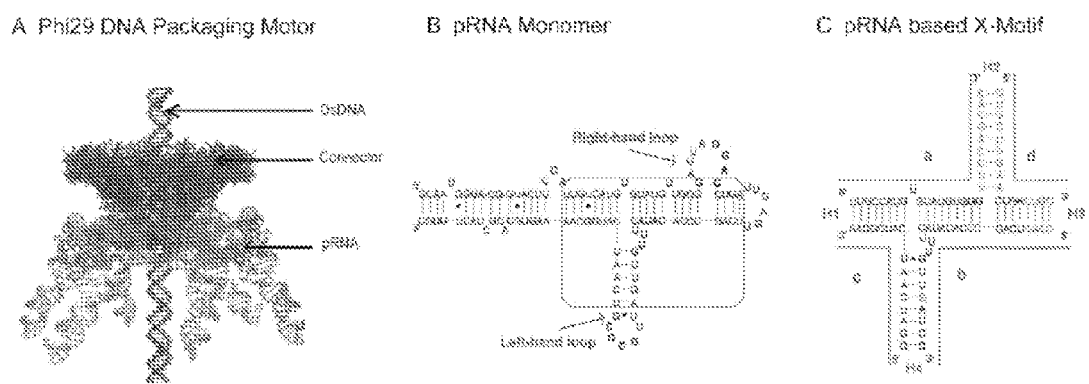
FIG. 40. Sequence and secondary structure of phi29 DNA-packaging RNA (pRNA). (A) Illustration of the phi29 packaging motor geared by hexameric pRNA ring (Cyan, Orange, Green, Blue, Brown, and Purple structures). (B) Sequence of pRNA monomer Ab'. The central domain for constructing the pRNA-X is boxed. (C) The core of the pRNA-X domain composed of four RNA oligos (a, b, c, and d). Helical segments are represented as H1, H2, H3 and H4. The additional bases used to construct the pRNA-X motif in helices H2 and H3 are marked in red. Ab' indicates non-complementary loops.
Figure 46:
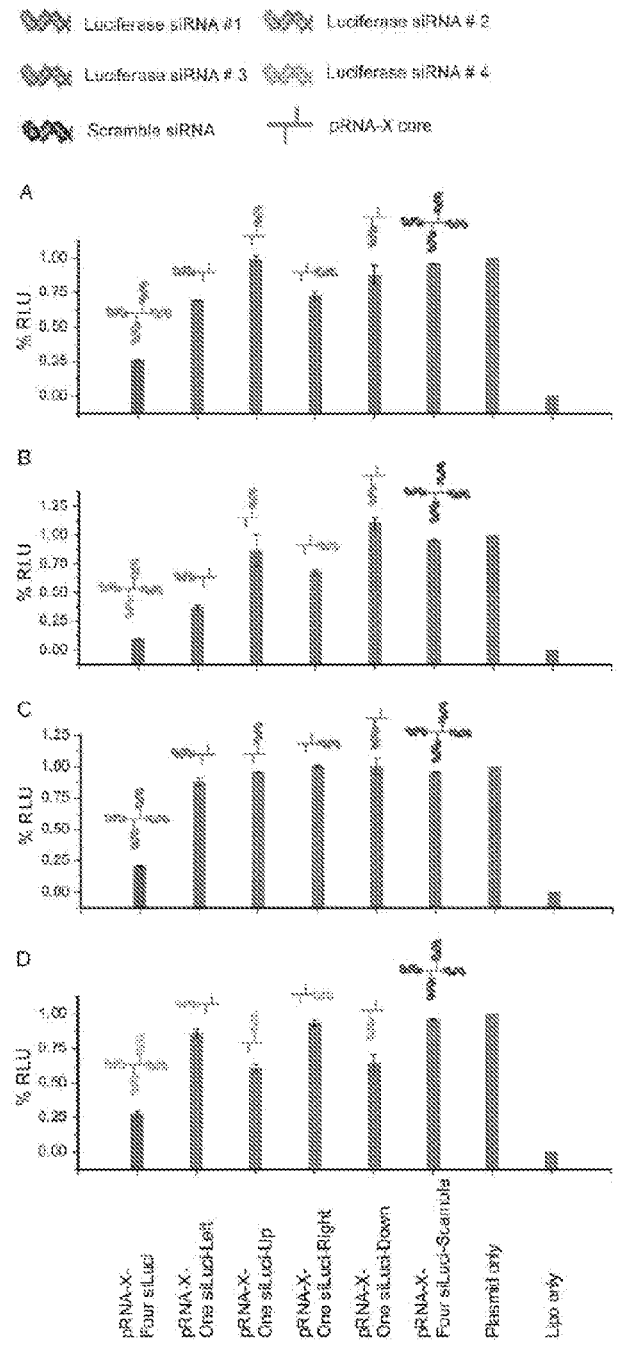
FIG. 46. Comparison of gene silencing effects for a single vs. multiple siRNAs incorporated in the pRNA-X motif. (A-D) Four identical siRNA (siLuci-1, A; siLuci-2, B; siLuci-3, C; siLuci-4, D) compared with a single siRNA harbored at each pRNA-X motif arm; RLU: Relative Luciferase Units; siLuci-1', 2' 3' and 4' represent reversed siRNA sequences for siLuci-1, 2, 3 and 4 respectively. Error bars represent s.d. (N=3).

Similar to the trifurcate domain design and function, we demonstrate that the centerfold domain of the pRNA could be engineered to form an X-shaped motif (FIG. 40C), which was thermodynamically stable, resistant to denaturation by 8 M urea and remained intact at ultra-low concentrations. Incubation of four RNA oligos with each carrying one of the four small RNA molecules, siRNA, receptor binding aptamer, or folate resulted in the formation of tetravalent RNA nanoparticles as potential therapeutic agents. We proved that each one of the four helixes in the X-motif can serve as sticky-ends to link one siRNA or other therapeutic molecules without affecting the folding of the central pRNA-X core. Systemic injection of nanoparticles with ligand into mice revealed that the RNA nanoparticles remained intact in vivo and strongly bound to receptor-positive cancers without trapping in liver, lung or any other organs or tissues.

The herein described trifurcate RNA junction domains and its derivative multivalent RNA junction domains will therefore find uses as scaffolds for the assembly of RNA nanoparticles carrying e.g., an siRNA, a drug, a ribozyme, an RNA aptamer, a riboswitch, a targeting moiety (e.g., a folate moiety), a marker or detectable label moiety, a fluorescent dye, a chemical modification (e.g., a modified nucleotide that resists degradation such as a 2'-fluoro-modified RNA nucleotide), or another chemical moiety having a desired function, for treatment and/or diagnosis of cancers, viral and/or other pathogenic infections, genetic diseases and other clinical disorders or conditions.

The self-assembled RNA nanoparticles carrying various bioactive moieties use herein described RNA junction scaffold form crystalline structure. Without limitation to its manners, the crystalline structure formation may utilize the bottom-up approach, as demonstrated in the Examples. By alternating the orientation of certain RNA polynucleotide's neighboring molecule, one can dictate the patterned array of the RNA crystalline structure. The RNA junction scaffold's core is usually a polygon formed by multiple RNA oligomers. In certain embodiments, the RNA crystalline structure is further arranged to form 1D and 2D sheets by controlling the RNA polynucleotides' numbers in a given unit of the scaffold.

The three-way junction (3WJ) and four-way junction (4WJ) motifs herein is used for the development of next-generation bispecific, trispecific and tetraspecific RNA aptamer platform using herein described RNA nanoparticle assembly approach. The RNA aptamers are selected via modified nanotechnology-based SELEX approaches (see Example 5 and FIG. 50-52). After the selection, the optimized aptamers are fused onto the 3WJ and 4WJ scaffolds, and the resultant RNA nanoparticles are further used in in vivo delivery of various diagnosis or therapeutic molecules.

Figure 50:
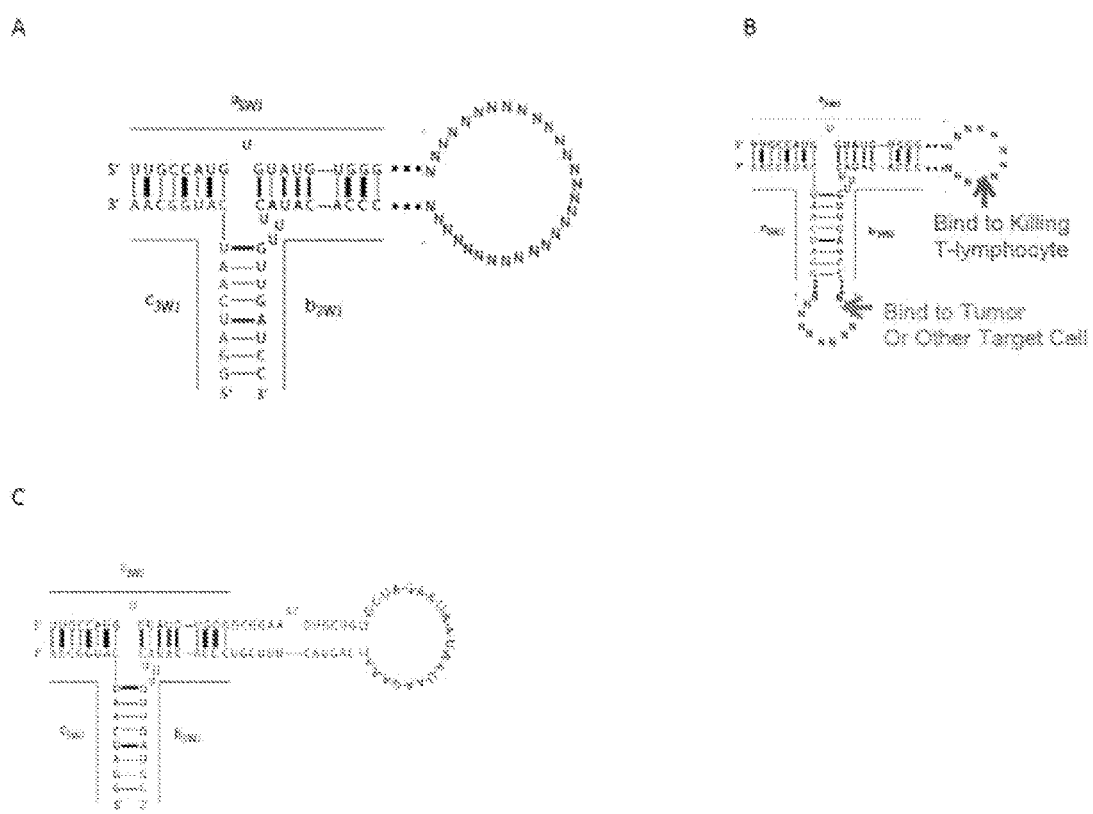
FIG. 50. Screening for RNA aptamers from different libraries that target cancer cell receptor, e.g. EPCAM. (A) 3WJ RNA with undefined number of random nucleotides at one branch of the loop of 3wj nanoparticle was used as library pool for the screening of RNA nanoparticles to bind cell receptors. (B) Undefined number of random sequence at the two loops of the 3WJ nanoparticle were used as library pool for the screening of RNA nanoparticles to bind cell receptors. (C) CEA aptamer was fused to 3WJ nanoparticle. In figures A-B, 37 N represent any number of any nucleotides.

To produce stable (2'-F modified) RNA aptamer with high binding affinity to a given substrate including antigen, protein, and cell surface markers, a collection of random sequences (12 nucleotides long) were attached to the terminus of H2 and H3 in pRNA trifurcate junction domain (FIG. 50-52). The resultant RNA complex harboring random sequence was evolved in vitro by SELEX techniques to identify those that bind to a given said substrate. Another strategy is to attach the available aptamer to the terminus of H2 and H3 in pRNA trifurcate junction domain. Such aptamer is different from traditional aptamer in that, in some embodiments, it has two or even more binding sites for the same substrate and the angle between H2 and H3 can be modulated by buffer conditions, therefore increase the efficacy of delivering targeted therapeutic molecule into living system; in other embodiments, one RNA nanoparticle carries multiple heterogeneous therapeutic molecules, therefore one RNA nanoparticle may bundle a particular combination of diagnosis or treatment molecule to the target site of a living system. A typical example of the later heterogeneous RNA nanoparticle carrier is a divalent aptamer carrying RNA molecules that recognize both cytotoxic T lymphocyte and a particular cancer cell marker. (FIG. 52D) The existence of such divalent aptamer in the living system will bring the T lymphocyte and tumor cells together, facilitate targeted cancer cell killing. Therefore, the model of Selex produced aptamer with high affinity to a given substrate mimics hybrid antibodies, and the two variable domains have huge clinical potential in disease detection and diagnosis.

Using herein described RNA aptamer selection and production, one can make various biological and synthetic RNAs to predetermined scaffolds. The resultant RNA nanoparticles can be used broadly for in vivo targeting and delivery of diagnosis or therapeutic molecules. An example would be using it for bi-specific, trispecific and tetra-specific (two antibody with each antibody for two valents, see FIG. 52D) in cancer killing.

The RNA 3WJ and 4WJ constructs harboring these selected aptamers herein described have the following features and offer significant advantages over the traditional monoclonal antibody fragments:

i. enhanced targeting capability with high specificity;
ii. enhanced thermodynamic and chemical stability;
iii. longer plasma half-life using chemically modified RNA;
iv. reproducible manufacturing framework for generating homogenous RNA nanoparticles via self-assembly of modular building blocks;
v. entirely RNA-based constructs, which will avoid immune responses and non-specific side effects,
vi. allows conjugation of chemotherapeutics to one of the branches of 3WJ/4WJ for 'cocktail' therapy;
vii. capable of crossing the blood-brain barrier for the treatment of head and neck cancer as well as brain cancer and central nervous system diseases.
viii. variable shaped RNA nanoparticles for optimized interactions.
ix. nanoscale size, which will enable it to bind to cryptic epitopes, that are not accessible by antibody fragments; escapes rapid kidney filtration.
x. deeper tumor penetrating capability
xi. offers multi-affinity targeting platform due to the polyvalent nature of the RNA scaffolds; will boost the therapeutic effects by engaging two or more targets simultaneously. Specific examples include, but not limited to, linking a T-cell with a tumor cell, targeting two antigens on a single tumor cell; cytokines for inflammatory diseases; angiogenic factors for solid tumors, etc.

Additional RNA junction domains beyond the phi29 pRNA trifurcate RNA junction domain are similarly stable, forming three-way, four-way, five-way, six-way or greater junctions as a scaffold to assemble RNA nanoparticles that can be used in various disease therapy or diagnosis. These RNA junction domains can also be used to promote RNA crystallization and to select stable RNA aptamer with high affinity to mimic antibody.

The trifurcate junction domain includes trifurcate junction domain of DNA packaging RNA from other phi29 family members, such as phages PZA, phi15, BS32, B103, Nf, M2Y and GA-1. These trifurcate junction domains are used for therapeutic delivery, diagnosis of diseases, promotion of RNA crystallization, or creation of stable RNA aptamer to mimic a given antibody.

The trifurcate junction domain includes but is not limited to the followings: pRNA, 5s rRNA, HCV, Alu SRP. Hammerhead ribozyme, 16s H34-H35-H38, 23s H75-H76-H79, 23s H83-H84-H85, G-Riboswitch (Type I), TPP Riboswitch (Type II), and M-box Riboswitch (Type II). These trifurcate junction domains are used for therapeutic delivery, diagnosis of diseases, promotion of RNA crystallization, or creation of stable RNA aptamer to mimic a given antibody.

Nomenclature

Figure 2:
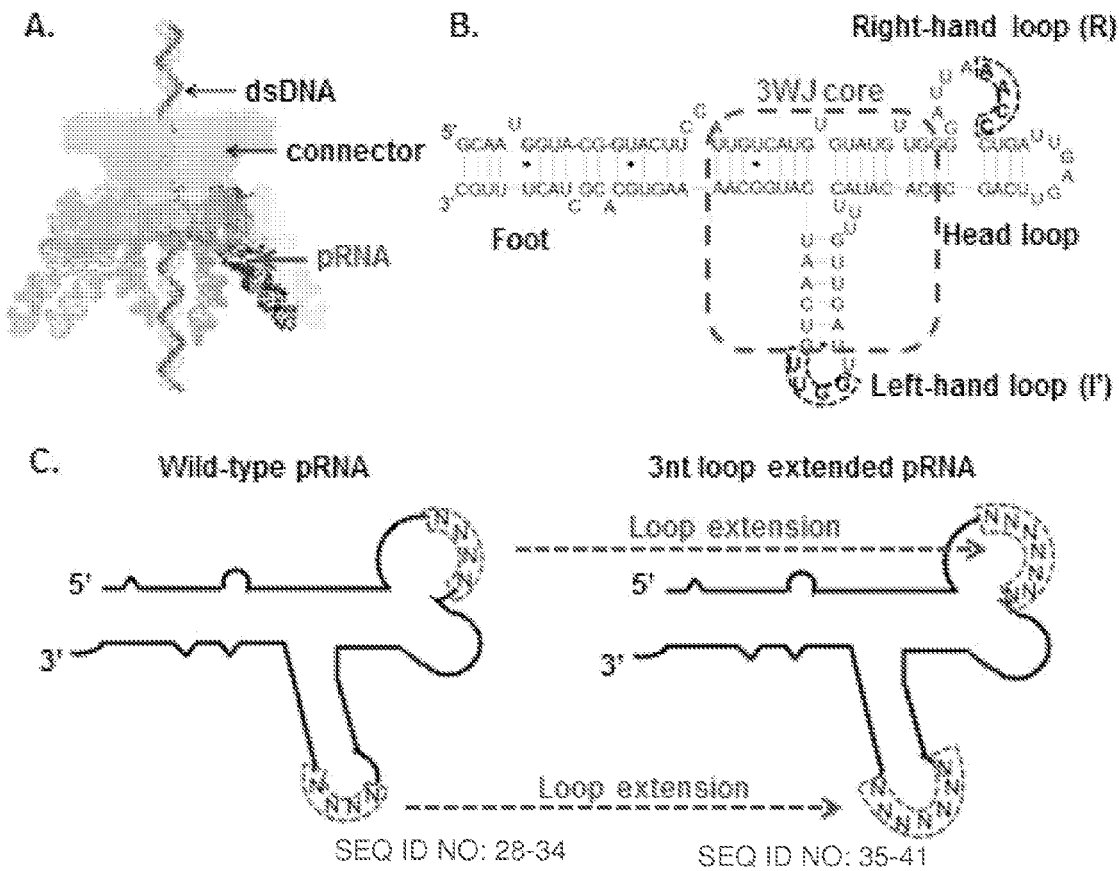
FIG. 2. The illustration of constructing loop extended pRNA. (A). Six copies of wild type pRNAs assemble a hexamer ring on the connector portal to gear the viral DNA into the prohead. (B) The primary sequence and secondary structure of wild-type pRNA. Two domains are connected by a 3WJ core. (C) The extension region of the pRNA loop sequences (4-nt to 7-nt). And the table of reengineered right hand and left hand loop sequences.

Following the pRNA nomenclature, a particular R-loop (upper loop) sequence is assigned an upper case letter (i.e., A, B, . . . ), and a particular L-loop (lower loop) sequence is assigned a lower case letter with a prime (i.e., a', b', . . . ). The same set of letters (i.e., Aa') designates complementary sequences in the R/L loop, while different letters indicate lack of sequence complementarities. In order to distinguish with the wild pRNA, a number 7 was added before the letters indicated that the loop-loop interaction sequences were extended from 4 bp to 7 bp (i.e. 7Aa'). The loop extended pRNA assigned with same set of letters (i.e. 7Aa') is in self-dimer format at native condition, so called "homo-dimer". The loop extended pRNA assigned with different set of letters (i.e. 7Ab') is in monomer format at native condition, so called "hetero-monomer" which require other partner subunits to form higher ordered pRNA polyvalent nanoparticles. "Hetero-dimer" is refer to pRNA dimers formed by two hetero-monomers such as 7Aa'-7Ba' (FIG. 2C).

The 3WJ domain of phi29 pRNA was constructed using three pieces of RNA oligos denoted as $a_{3WJ}$, $b_{3WJ}$ and $c_{3WJ}$. The three branches were named as H3-1, H3-2, and H3-3 (FIG. 6A). The 3WJ derived X-shaped pRNA was constructed using four pieces of RNA oligos denoted as $a_{4WJ}$, $b_{4WJ}$, $c_{4WJ}$, and $d_{4WJ}$. The four branches were named as H4-1, H4-2, H4-3, and H4-4 (FIG. 6B).

Techniques for Constructing RNA Nanoparticles.

Construction of nanoparticles may in preferred embodiments involve the use of programmable, addressable and predictable building blocks. Self-assembly of RNA building blocks in a predefined manner to form larger two-, three-, and four-dimensional structures is a prominent bottom-up approach and represents an important means by which biological techniques and biomacromolecules can be successfully integrated into nanotechnology.

Self-assembly may be regarded as having two main sub-categories: templated and non-templated assembly. Templated assembly involves the interaction of RNAs with one another under the influence of a specific external force, structure, or spatial constraint. RNA transcription, hybridization, replication, molding, and phi29 pRNA hexameric ring formation are all within this category. Non-templated assembly involves the formation of a larger structure by individual components without any external influence. Examples include ligation, chemical conjugation, covalent linkages, loop/loop interactions of RNA such as the HIV kissing loop, and phi29 pRNA dimer or trimer formation. Various approaches available for RNA nanoparticle construction are discussed herein and known in the art.

One approach utilizes the assembly mechanism of natural RNA nanoparticles that can form unique and intriguing multimers in vivo. For example, the retrovirus kissing loops facilitate genomic RNA dimerization. The pRNA of the bacteriophage phi29 DNA packaging motor assembles into dimers and hexamers via hand-in-hand interactions between two right and left interlocking loops. The bicoid mRNA of *Drosophila* embryos forms dimers via hand-in-arm interactions. *E. coli* noncoding RNA DsrA assembles into stripe patterns via their built-in palindrome sequence. The assemblies of RNA nanoparticles in vitro that mimic their natural counterparts were reported twelve years ago. The novel HIV kissing loop mechanism has also inspired the design of tecto-RNA architectures.

RNA is more rigid in bulge structure due to the occurrence in RNA (but typically not in DNA) of non-canonical interactions, while in DNA, the twisting typically requires the interaction of two DNA helices with four strands.

Recently, RNA cubic scaffold were constructed using several RNA sequences that do not fold on themselves but instead self-assemble with one another in a defined manner. This strategy is reminiscent of DNA nanotechnology, but in contrast to DNA strategies, RNA synthesis can be coupled to RNA self-assembly to generate fully assembled RNA cubes during in vitro transcription.

Another approach to RNA nanoparticle construction is to apply computational methods. Computational methodologies may be used to guide the design of novel RNA assemblies and to optimize sequence requirements for the production of nanoscale fabrics with controlled direction and geometry. In contrast to traditional methods in which raw materials are selected rather than designed for a given application, RNA building blocks may be designed a priori for programmed assembly and synthesis. In certain implementations there may be two steps in building RNA nanoparticles. The first step may be a computational approach (e.g., using Kinefold) utilizing the spontaneous self-folding property of RNA into defined structures via base/base interactions based on their characteristic $\Delta G$. The second step may then be the spontaneous assembly of the resulting RNA building blocks into larger assemblies, based on the predicted architecture. These and related strategies represent an effective computational pipeline for generating molecular models of RNA nanostructures. A recent example is the construction of cubic RNA-based scaffolds, whereby RNA sequence designs were optimized to avoid kinetic traps.

Yet another approach may utilize an existing RNA structure having a known function, as a building block in RNA nanoparticle construction. Varieties of mechanisms in RNA loop/loop interactions, tertiary architecture contacts, and formation of special motifs have been elucidated. Building-blocks may be first synthesized after computing intra- and intermolecular folding. Nanoparticles are built through spontaneous templated or nontemplated self-assembly as planned. A rich resource of well-developed databases can be utilized to extract known RNA structural units for construction of novel RNA nanoparticles with desired properties.

One of the RNA properties, loop/loop interactions, is useful for the construction of RNA nanoparticles. One such method is based on the structural features of the pRNA of the bacteriophage phi29 DNA packaging motor which uses a hexameric RNA ring (packaging RNA, or "pRNA") to gear the machine. The pRNA has been reengineered to form dimers, trimers, tetramers, hexamers and arrays via hand-in-hand or foot-to-foot interactions between two interlocking loops. Dimers are formed using two building blocks with A/b' (right and left hand, respectively) and B/a'. Trimers are formed using three building blocks with A/b', B/c', and C/a'. Multimers are formed using building blocks with multiple homo-dimers or hetero-monomers as defined previously.

Chimeric pRNA in which the naturally occurring pRNA sequence is altered, including by the repositioning of the 5'/3' break, by the replacement of some or all of the double-helical or translocation domain with biologically active moieties (e.g., siRNA, ribozymes, aptamers, antisense RNA, structures to promote receptor-mediated endocytosis), by chemical modification (e.g., by covalent attachment of ligand moieties such as folate, or of labeling moieties, or of therapeutic agents, or by incorporation of nuclease-resistant nucleotides) have been described, as has the formation of multivalent RNA nanoparticles therefrom, in e.g., WO/2002/016596; U.S. Pat. No. 7,655,787; WO/2005/003293; WO/2007/016507, which are expressly incorporated by reference herein. Dimers of pRNA in an extended configuration (twins) can also be efficiently self-assembled by introducing a palindrome sequence into the 3'-end of the pRNA. These nanoparticles have been used successfully as polyvalent vehicles to deliver a variety of therapeutic molecules. The use of pRNA as building blocks for the construction of RNA arrays has also been achieved.

When three twins. Ab', Bc' and Ca' are mixed, loop/loop interlocking makes the particles grow in three-dimensions.

Alternatively, RNA "architectonics" methodologies may be employed, whereby structural modules specifying for bends or stack can be encoded within artificial RNA sequences for self-assembling higher order specific shapes of RNA. Examples include, RNA filaments, molecular jigsaw puzzle units called tectosquares and tRNA antiprisms.

Certain preferred embodiments as described herein may employ a novel phi29 pRNA-derived 3WJ (three-way junction), where other 3WJ and four-way junctions (4WJ) or even more-way junctions may be selected from known RNA structures or motifs from certain biological system to serve as the cornerstone in nanoparticle construction. Some of these examples include: RNA-structural motif (from rRNA) to guide the tetramer assembly of L-shaped tectoRNAs; 3WJ-motif (from 23S rRNA) to construct T-shaped arrangement of three helices; and, tRNA motifs consisting of 4- and 5-WJ to fold L-shaped tertiary structures. Accordingly and as described herein, certain presently contemplated embodiments may expressly exclude, whilst certain other presently contemplated embodiments may include, 3WJ and/or 4WJ structures from these described biological systems such as those described in one or more of Severcan et al., 2009 *Nano. Lett.* 9(3):1270; Ouellet et al., 2010 *RNA* 16(8):1597; Lescoute et al., 2006 RNA 12(1):83; de la Pina et al., 2009 *RNA* 15(11):1949; Scluneing and Steitz, 2005 *Mol. Cell* 20:437; Vila-Sanjuro et al., 2003 *Proc. Nat. Acad. Sci. USA* 100:8682; Golden et al., 1998 *Science* 282:259; Ban et al., 2000 *Science* 289:905, Schuler et al., 2006 *Nat. Struct. Mol. Biol.* 13:1092; Schuwirth et al., 2006 *Nat. Struct. Mol. Biol.* 13:879. The applicant thereby first time applies the concept of multiple-way junction domains with the modifications detailed in this disclosure to the described uses herein.

Attachment of Functionalities

An siRNA helix may comprise 18-30, 18-27, or preferably 20-25 nucleotides, and interferes with gene expression through the cleavage of mRNA by a protein/RNA complex named RISC (RNA-induced silencing complex), as also discussed above. The siRNA specifically (e.g., with statistical significance, relative to an appropriate control of irrelevant structure) suppresses the expression of a target protein whose mRNA includes a sequence identical to the sense strand of the siRNA.

A ribozyme may comprise an RNA molecule that has enzymatic activity. Ribozymes have significant therapeutic potential and may be capable of regulating gene function by intercepting and cleaving RNA substrates, such as mRNA or the viral genome of RNA containing a sequence complementary to the catalytic center of the ribozyme.

An RNA aptamer may be a member of a family of oligonucleotides with functions similar to that of antibodies in their ability specifically to recognize ligands (e.g., organic compounds, nucleotides, or peptides) through the formation of binding pockets. Systematic evolution of ligands by exponential enrichment (SELEX) is a method used to screen for aptamers having desired binding specificities, from randomized RNA pools developed in vitro, Using this technique, various aptamers have been selected for targeting markers relevant to diseases.

Riboswitches include RNA components that bind small molecules and control gene expression in response to an organism's needs. As a biological control mechanism, riboswitches can recognize metabolites, induce premature termination of mRNA transcription, block ribosomes from translating mRNAs, cleave mRNAs, and even trigger mRNA destruction. Therefore, RNA switches can be reengineered to create a new generation of controllers regulated by drug-like molecules to tune the expression levels of targeted genes in vivo. Such RNA-based gene-control machines hold promise in future gene therapies by supplying nanoscale cis-acting modulation.

Various RNA moieties including siRNAs, ribozymes, antisense RNAs, aptamers, riboswitches, as well as other catalytic or editing RNAs can, according to art-accepted methodologies, be readily fused to or conjugated with RNA oligonucleotide subunits of the herein described trifurcate RNA junction domains, to provide a modular system for the assembly of RNA nanoparticles. Among the advantages of the thus-provided compositions and methods as disclosed herein, e.g., for RNA nanomedicine, there are included the attributes of: 1) self-assembly; 2) high physicochemical and physiological stability, 3) multi-valency; 4) targeted delivery; 5) protein-free (including advantages associated with being non-immunogenic, non-inflammatory, non-toxic, non-eliciting of lymphokine, chemokine or cytokine responses such as an interferon response); 6) nanoscale size; 7) controlled synthesis with defined structure and stoichiometry; 8) combining therapy and detection of therapy effects into one particle.

Bottom-up assembly of RNA can lead to multi-valency. Each subunit may be separately functionalized to carry different therapeutic payloads, reporters and/or targeting ligands. Cell-type-specific delivery allows a lower concentration of the drug to be administered, thus reducing the side effects. The multivalent approach permits certain embodiments to be contemplated in which a mixture of therapeutic agents (e.g., different drugs delivered via a different subunit that may be assembled into the nanoparticle complexes assembled using the herein described trifurcate RNA junction domain) is used to produce a synergistic effect. The multivalency offers an additional advantage in these and/or other contemplated embodiments that permit therapy along with detection of therapeutic effects, combined into one nanoparticle that is introduced in a single administration.

The present embodiments overcome problems associated with previous nanomedicine approaches, such as uncertainty in the structure and/or stoichiometry of delivered nanoparticles that could cause unpredictable side effects or nonspecific toxicity. The present trifurcate RNA junction domain-based nanotechnology, and their derivative scaffolds, by contrast, provides for the production of homogeneous nanoparticles that can be "manufactured" with high reproducibility, and with defined structure and stoichiometry, thus facilitating quality and safety control.

RNA nanoparticles assembled using the present trifurcate RNA junction domain or multivalent RNA junction scaffold may be typically and advantageously sized in the nanometer-scale. For effective delivery to diseased tissues, many studies suggest that particles ranging from 10-50 nm are optimal for a nonviral vector as they are large enough to be retained by the body yet small enough to pass through the cell membrane via the cell surface receptor mediated endocytosis. The herein described nanoparticle delivery thus may improve the pharmacokinetics, pharmacodynamics, biodistribution, and safety of therapeutic and/or diagnostic agents. Additionally and as noted above, the protein-free nature of the herein described RNA nanoparticles assembled using the present trifurcate RNA junction domain may result in these nanoparticles being substantially non-immunogenic; by avoiding the induction of antibodies in a recipient, these embodiments permit safely repeated administration of the nanoparticles for the treatment of chronic diseases including cancers, viral infections, and genetic ailments. RNA nanoparticles are classified by the FDA as chemical rather than biological entities.

Methodologies for RNA nanotechnology in disease therapy has been exemplified using the phi29 pRNA therapeutic system and may now be enhanced through the use of the herein described RNA nanoparticles assembled using the presently disclosed trifurcate RNA junction domain and other multivalent RNA junction scaffolds derivatives.

In the phi29 pRNA system, incubation of synthetic polyvalent RNA nanoparticles containing receptor-binding aptamers or ligands resulted in cell binding and entry of the incorporated therapeutics, subsequently modulating apoptosis. The delivery efficiency and therapeutic effect were later confirmed in animal trials. The 3D design, circular permutation, folding energy alteration, and nucleotide modification of RNA were applied to generate RNase resistant RNA nanoparticles with low toxicity, and to ensure processing of the chimeric RNA complexes into siRNA by Dicer after delivery. Accordingly, the trifurcate RNA junction domain as disclosed herein for the first time provides, inter alia, enhanced stability, production efficiency, safety and versatility for use according to the established pRNA platform.

As described herein and in certain preferred embodiments, two or three or even more RNA nanostructure domains (e.g., similar or dissimilar domains such as biologically active moiety-containing or other functional domains, for instance, siRNA, molecular targeting moieties, ribozymes, anti-sense RNA, aptamers, etc.) may be connected by the herein disclosed trifurcate RNA junction domain (e.g., FIG. 1E) or multivalent RNA junction scaffolds, which may be derived from phi29 pRNA. The unique structure of pRNA and of this trifurcate region or its multivalent derivatives will find numerous uses in RNA nanotechnology, including in therapeutics, diagnostics, drug screening, biological and biomedical research, and other arenas.

As also disclosed herein, the trifurcate RNA junction domain, or trifurcate region, comprises a domain or motif of the pRNA that can be assembled from three pieces of small RNA (e.g., RNA oligonucleotides) having unusually high affinity for one another. The resulting complex is highly stable and resistant to denaturation even in the presence of strong denaturants such as 10M urea. Incubation of three RNA oligonucleotides, each comprising one of the three small RNA molecules, which in certain embodiments may also comprise one or more of an siRNA, a receptor binding aptamer, a ribozyme, or another desired RNA sequence or RNA-based structure, results in the formation of tri-star RNA nanoparticles which may find a variety of uses, for instance, as therapeutic agents.

Therapeutic Methods.

One or more RNA nanoparticles, such as a nanoparticle comprising the herein described trifurcate RNA junction domain, for example a nanoparticle comprising one or more siRNA polynucleotides that are capable of interfering with target polypeptide expression, may also be used to modulate (e.g., inhibit or potentiate) target polypeptide activity in a patient. As used herein, a "patient" may be any mammal, including a human, and may be afflicted with a condition associated with undesired target polypeptide activity or may be free of detectable disease. Accordingly, the treatment may be of an existing disease or may be prophylactic. Non-limiting examples of conditions associated with inappropriate activity of specific siRNA target polypeptides may include disorders associated with cell proliferation, including cancer, graft-versus-host disease (GVHD), autoimmune diseases, allergy or other conditions in which immunosuppression may be involved, metabolic diseases, abnormal cell growth or proliferation, infectious diseases, obesity, impaired glucose tolerance and diabetes, and cell cycle abnormalities.

For administration to a patient, one or more RNA nanoparticles, such as a nanoparticle comprising the herein described trifurcate RNA junction domain, or comprised in an appropriate vector (e.g., including a vector which comprises a DNA sequence from which the subunits of the RNA nanoparticle can be transcribed and then self-assembled) are generally formulated as a pharmaceutical composition. A pharmaceutical composition may be a sterile aqueous or non-aqueous solution, suspension or emulsion, which additionally comprises a physiologically acceptable carrier (i.e., a non-toxic material that does not interfere with the activity of the active ingredient). Such compositions may be in the form of a solid, liquid or gas (aerosol). Alternatively, compositions of the present invention may be formulated as a lyophilizate or compounds may be encapsulated within liposomes using well known technology. Pharmaceutical compositions within the scope of the present invention may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, stabilizers, dyes, flavoring agents, and suspending agents and/or preservatives.

Any suitable carrier known to those of ordinary skill in the art may be employed in the pharmaceutical compositions of the present invention. Carriers for therapeutic use are well known, and are described, for example, in *Remingtons Pharmaceutical Sciences*, Mack Publishing Co. (A. R. Gennaro ed. 1985). In general, the type of carrier is selected based on the mode of administration. Pharmaceutical compositions may be formulated for any appropriate manner of administration, including, for example, topical, oral, nasal, intrathecal, rectal, vaginal, sublingual or parenteral administration, including subcutaneous, intravenous, intramuscular, intrasternal, intracavernous, intrameatal or intraurethral injection or infusion. For parenteral administration, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, kaolin, glycerin, starch dextrins, sodium alginate, carboxymethylcellulose, ethyl cellulose, glucose, sucrose and/or magnesium carbonate, may be employed.

A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The compositions described herein may be formulated for sustained release (i.e., a formulation such as a capsule or sponge that effects a slow release of compound following administration). Such compositions may generally be prepared using well known technology and administered by, for example, oral, rectal or subcutaneous implantation, or by implantation at the desired target site. Sustained-release formulations may contain an agent dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Within a pharmaceutical composition, a therapeutic agent comprising an RNA nanoparticles comprising the herein described trifurcate RNA junction domain, as described herein (or, e.g., a recombinant nucleic acid construct comprising a polynucleotide encoding one or more of the RNA subunits of such a nanoparticle) may be linked to any of a variety of compounds. For example, such an agent may be linked to a targeting moiety (e.g., a small molecule ligand, an aptamer, a monoclonal or polyclonal antibody, a protein or a liposome) that facilitates the delivery of the agent to the target site. As used herein, a "targeting moiety" may be any substance (such as a compound or cell) that, when linked to an agent enhances the transport of the agent to a target cell or tissue, thereby increasing the local concentration of the agent. Targeting moieties include small molecule ligands (e.g., folate), aptamers, antibodies or fragments thereof, receptors, ligands and other molecules that bind to cells of, or in the vicinity of, the target tissue. An antibody targeting agent may be an intact (whole) molecule, a fragment thereof, or a functional equivalent thereof. Examples of antibody fragments are $F(ab')_2$, Fab'. Fab and F[v] fragments, which may be produced by conventional methods or by genetic or protein engineering. Linkage is generally covalent and may be achieved by, for example, direct condensation or other reactions, or by way of bi- or multi-functional linkers. Targeting moieties may be selected based on the cell(s) or tissue(s) toward which the agent is expected to exert a therapeutic benefit.

Pharmaceutical compositions may be administered in a manner appropriate to the disease to be treated (or prevented). An appropriate dosage and a suitable duration and frequency of administration will be determined by such factors as the condition of the patient, the type and severity of the patient's disease, the particular form of the active ingredient and the method of administration. In general, an appropriate dosage and treatment regimen provides the agent(s) in an amount sufficient to provide therapeutic and/or prophylactic benefit (e.g., an improved clinical outcome, such as more frequent complete or partial remissions, or longer disease-free and/or overall survival, or a lessening of symptom severity). For prophylactic use, a dose should be sufficient to prevent, delay the onset of or diminish the severity of a disease associated with cell proliferation.

Optimal dosages may generally be determined using experimental models and/or clinical trials. In general, the amount of RNA nanoparticles (comprising the herein described trifurcate RNA junction domain) that is present in a dose, or that is produced in situ by DNA present in a dose (e.g., from a recombinant nucleic acid construct comprising an encoding polynucleotide), ranges from about 0.01 µg to about 100 µg per kg of host, typically from about 0.1 µg to about 10 µg. The use of the minimum dosage that is sufficient to provide effective therapy is usually preferred. Patients may generally be monitored for therapeutic or prophylactic effectiveness using assays suitable for the condition being treated or prevented, which will be familiar to those having ordinary skill in the art. Suitable dose sizes will vary with the size of the patient, but will typically range from about 10 mL to about 500 mL for 10-60 kg animal.

Multifunctional RNA nanoparticles assembled using the trifurcate RNA junction domain of phi29 pRNA as an assembly scaffold were extremely stable and did not dissociate at ultra-low concentrations as demonstrated by radiolabel and competition assays. The RNA nanoparticles were resistant to dissociation under extreme denaturing conditions (10M urea), compared to dsDNA that is denatured with 5M or 7M urea. The complexes may be assembled with high efficiency from chemically synthesized short RNA oligos at room temperature in the absence of magnesium. By simple chemical modifications with nucleotide derivatives, such as 2'-Fluoro modified nucleotides, the resulting RNA nanoparticles have significantly enhanced stability in the serum for an extended period of time. The in vitro constructed RNA therapeutic nanoparticles were functionally active, as demonstrated by cell binding assays via receptor-binding aptamer, substrate cleavage with a (hammerhead) ribozyme, and fluorescence emission through the MG binding capability. The RNA nanoparticles remained intact for several hours circulating in the animal body and were observed to bind to target cells with high specificity, to silence the gene in cancer cells in vivo and to inhibit the tumor growth in a tumor-xenografted mouse model. These results demonstrated that the phi29 trifurcate domain and its derivatives can be used as a platform for the construction of RNA nanoparticles containing multiple functionalities for the delivery of therapeutics to specific cells for the treatment of cancer, viral infection, and genetic diseases.

The following Examples are presented by way of illustration and not limitation.

EXAMPLES

Example 1

Experimental Procedures

In Vitro Synthesis and Purification of pRNA and Chemically Modified pRNA.

The pRNAs were synthesized by enzymatic methods as described previously. RNA oligos were synthesized chemically by IDT. 2'-deoxy-2'-Fluoro (2'-F) modified RNAs were synthesized by in vitro transcription with the mutant Y639F T7 RNA polymerase using the 2'-F modified dCTP and dUTP (Trilink).

Construction and Purification of pRNA Dimers and Trimers.

Dimers were constructed by mixing equal molar ratios of pRNA Ab' and Bb' in presence of 5 mM magnesium [TBM (89 mM Tris, 200 mM Boric Acid, 5 mM $MgCl_2$, pH 7.6) or TMS (89 mM Tris, 5 mM $MgCl_2$, pH 7.6) buffer]. Similarly, trimers were assembled by mixing pRNA Ab', Bc', and Ca'. To purify the complex, the band corresponding to the trifurcate domain was excised from 8%0 native PAGE gel, eluted (0.5 M $NH_4OAC$, 0.1 mM EDTA, 0.1% SDS, and 0.5 mM $MgCl_2$) for ~4 hrs at 37° C., followed by ethanol precipitation overnight. The dried pellet was then rehydrated in DEPC treated water or TMS buffer.

Construction and Purification of the Trifurcate Domain Using Three Pieces of RNA Oligos.

The trifurcate domain was constructed using three pieces of RNA oligos, denoted as $a_{3WJ}$, $b_{3WJ}$, and $c_{3WJ}$ that were mixed at 1:1:1 molar ratio in DEPC treated water. The formation of the complexes was then analyzed by 15% native PAGE or 8M urea PAGE gel, as indicated. After running at 4° C. for 3 hrs, the RNA was visualized by ethidium bromide or SBYR Green II staining. The trifurcate domain was then purified by 8% native PAGE gel.

Construction of Tri-Star RNA Nanoparticles Harboring Three pRNA Nanoparticles (3WJ-3pRNA) or Therapeutic and Reporter Moieties (3WJ-Folate-Ribozyme-siRNA or 3WJ-Folate-Aptamer-siRNA).

Sequences for each of the RNA strands $a_{3WJ}$, $b_{3WJ}$, and $c_{3WJ}$ were added to the 3'-end of each 117-nt pRNA-Ab' (FIG. 1E). The pRNA-$a_{3WJ}$, pRNA-$b_{3WJ}$, and pRNA-$c_{3WJ}$ were then synthesized in vitro by transcription of the corresponding DNA template by the T7 RNA polymerase. The pRNA chimeras were purified in 8% urea PAGE gel. Tri-star 3WJ-3pRNAs were then self-assembled by mixing the three subunits in equal molar concentrations. Alternatively, the three individual templates can be co-transcribed and assembled in one step followed by purification in 8% native PAGE gel.

Figure 15:
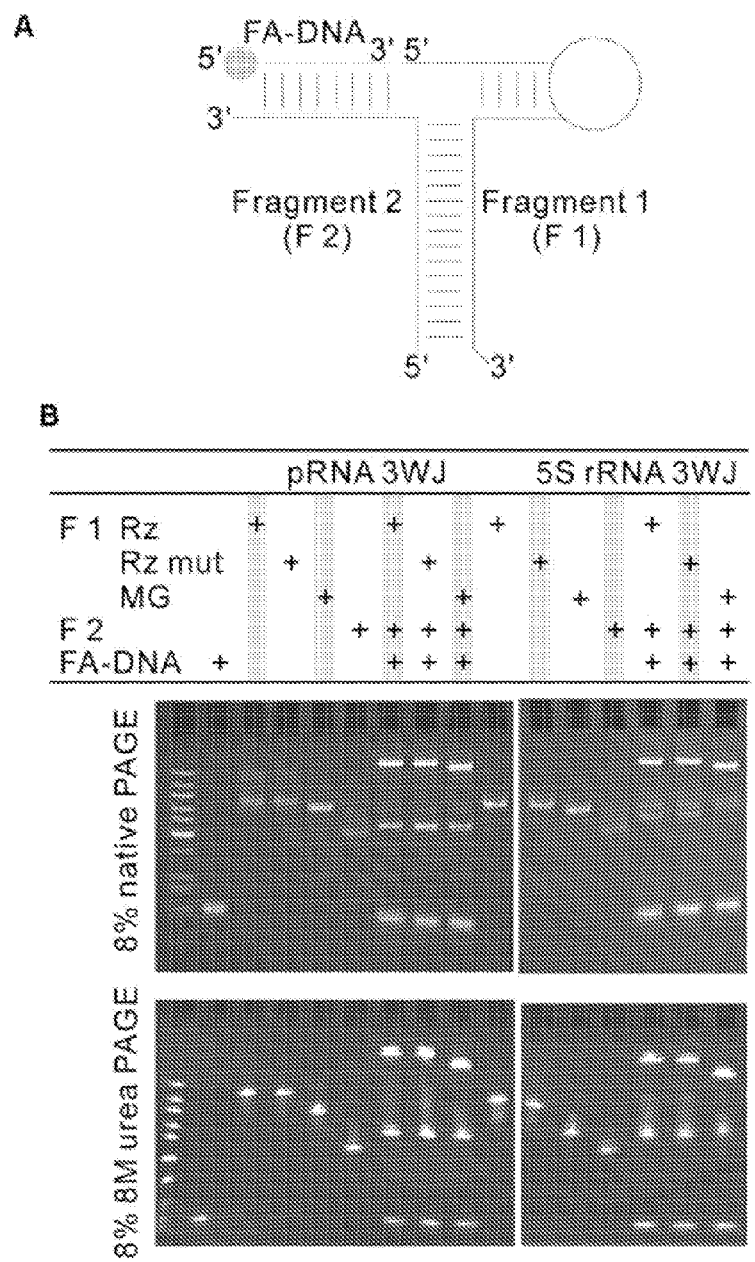
FIG. 15 Assembly of RNA nanoparticles with functionalities using 3WJ-pRNA and 3WJ-5S rRNA as scaffolds. (A) Illustration. (B) 8% native (upper) and denaturing (lower) PAGE gel.
Figure 30:
FIG. 30 presents sequences used for constructing the RNA nanoparticles with functionalities
Figure 32:
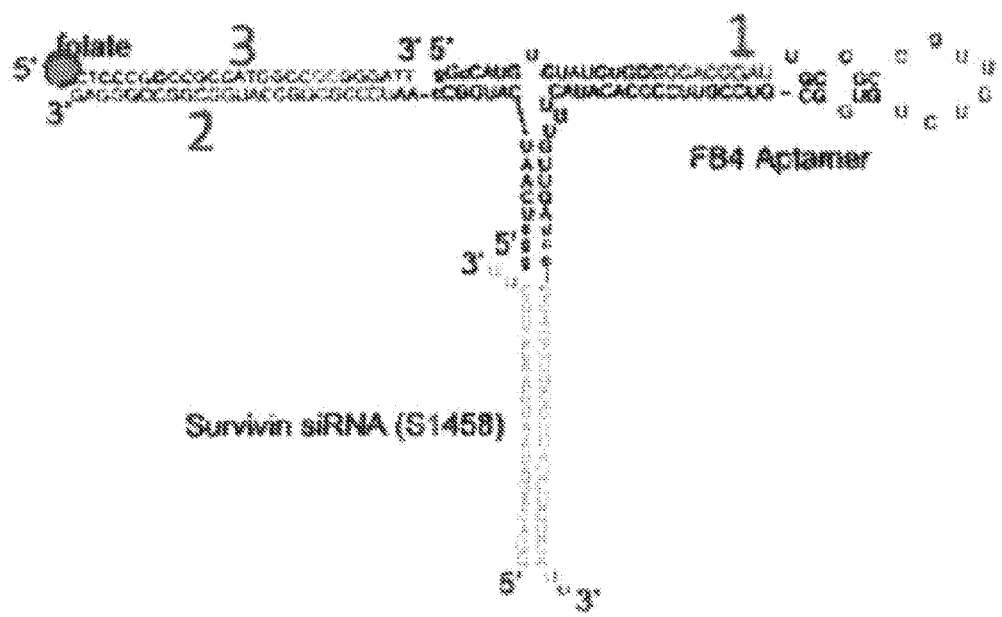
FIG. 32 shows a trifurcate RNA three-way junction (3WJ) incorporated into an RNA having three different biologically active moieties including a folate targeting moiety, an FB4 aptamer moiety and a survivin-specific siRNA moiety.
Figure 33:
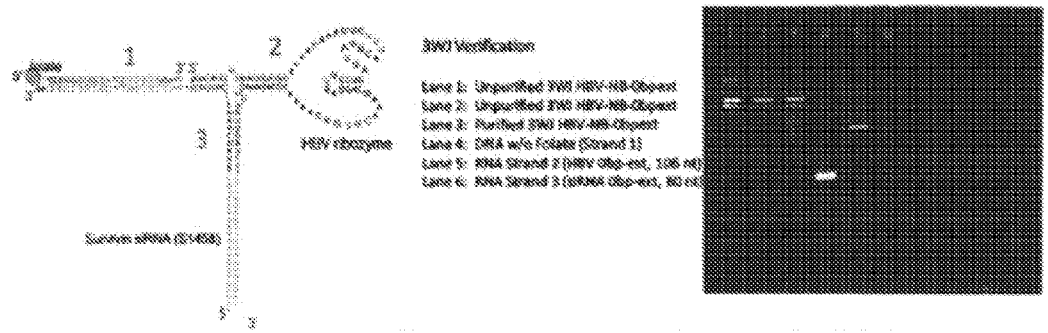
FIG. 33 shows a trifurcate RNA three-way junction (3WJ) incorporated into an RNA having three different biologically active moieties including a folate targeting moiety, an HBV ribozyme moiety and a survivin-specific siRNA moiety.
Figure 34:
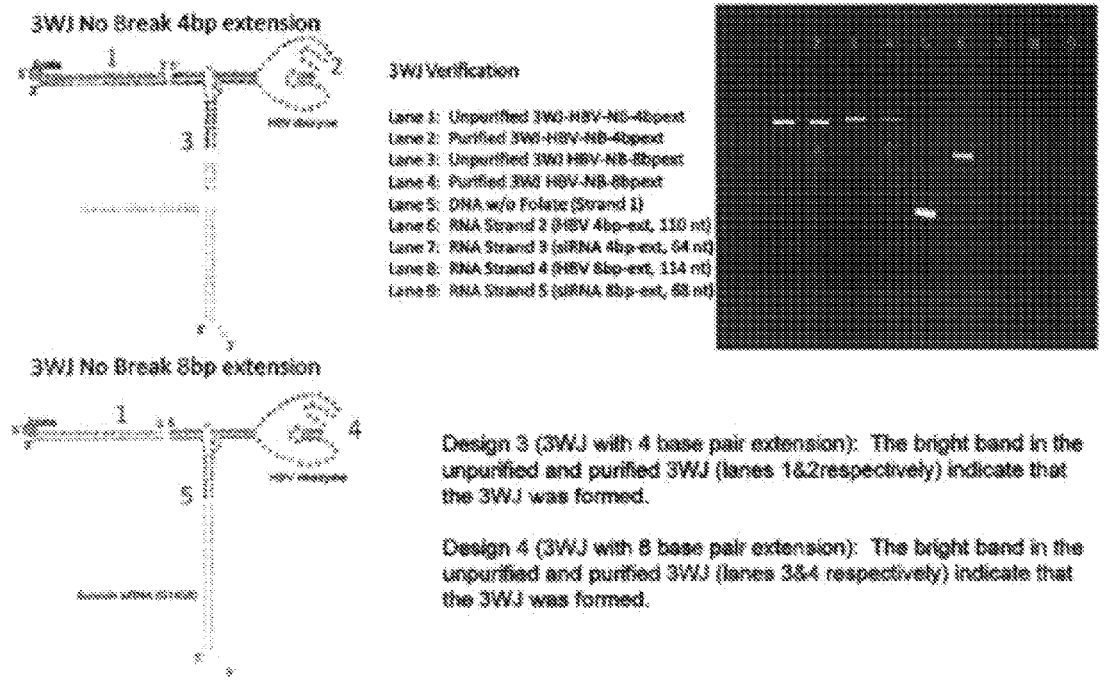
FIG. 34 shows trifurcate RNA three-way junctions (3WJ) incorporated into RNAs having three different biologically active moieties including a folate targeting moiety, an HBV ribozyme moiety and a survivin-specific siRNA moiety.
Figure 35:
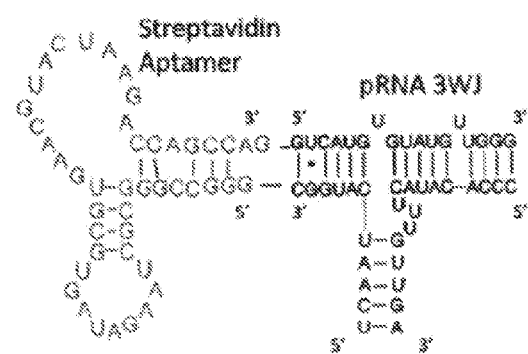
FIG. 35 shows a trifurcate RNA three-way junction (3WJ) incorporated into an RNA having a streptavidin aptamer.
Figure 36:
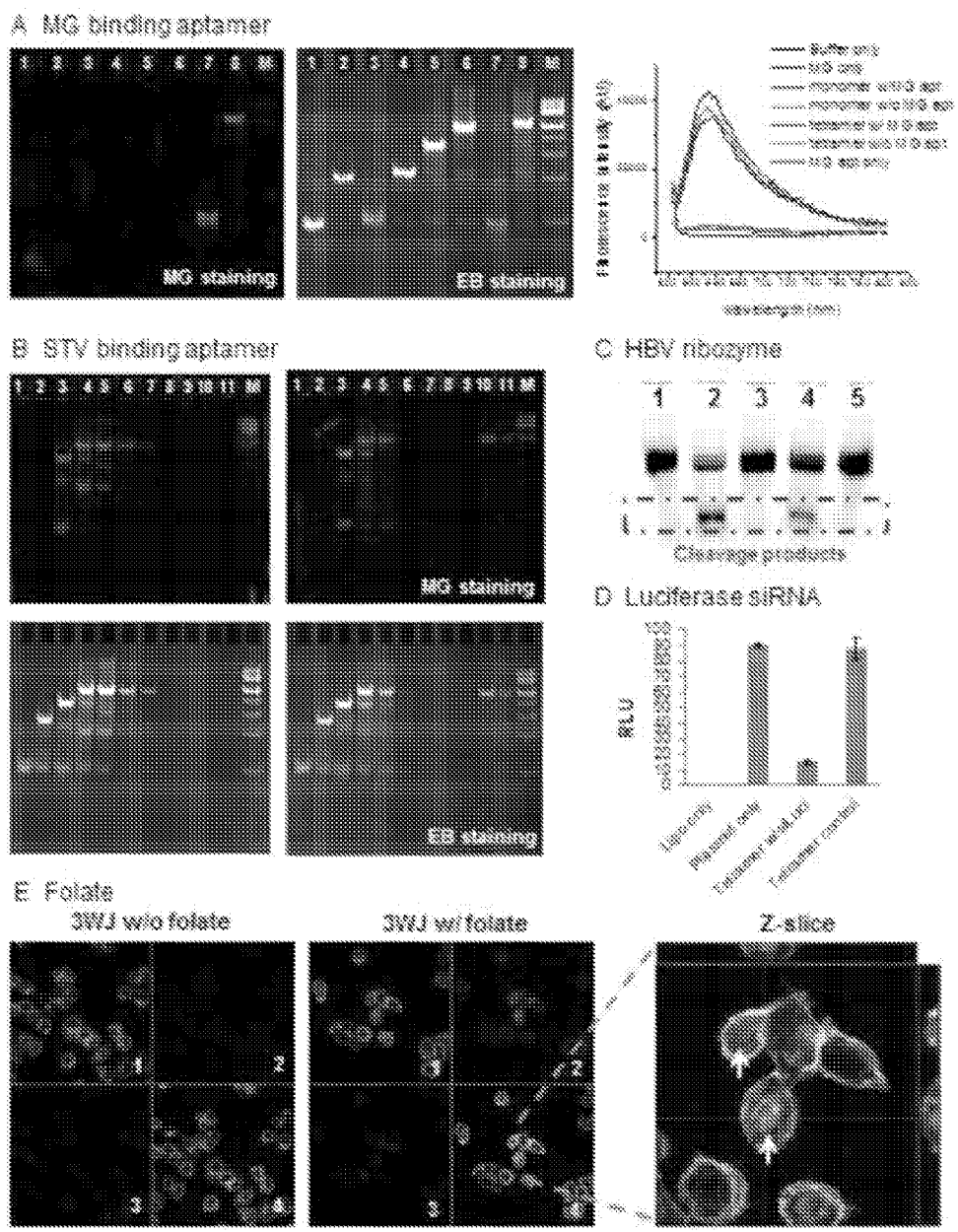
FIG. 36. Assay of each functional moiety while incorporating in pRNA nanoparticles. (A) MG aptamer binding assay. 6% native PAGE (1: Wild-type pRNA Ab' monomer; 2: Wild-type pRNA Aa' dimer; 3: loop extended pRNA monomer; 4: loop extended pRNA dimer; 5: loop extended pRNA trimer, 6: monomer subunit harboring MG binding aptamer; 7: tetramer harboring MG binding aptamer) visualized by both MG staining and ethidium bromide staining. (B) STV binding assay. 6% native PAGE (1: loop extended pRNA monomer, 2: loop extended pRNA dimer; 3: loop extended pRNA trimer; 4: loop extended tetramer control; 5: passing through; 6: wash 1; 7: wash 2; 8: wash 6; 9: wash 7; 10: elution; 11: elution 2; 12: 100 bp DNA ladder) visualized by both MG staining and ethidium bromide staining. (C) Assay HBV ribozyme function. (D) Dual-luciferase assay for investigate siRNA function. (E) Confocal images showed targeting of FA+KB cells by co-localization (overlap, 4) of cytoplasm (green, 1) and RNA nanoparticles (red, 2) (magnified, right panel). Blue-nuclei, 3.
Figure 37:
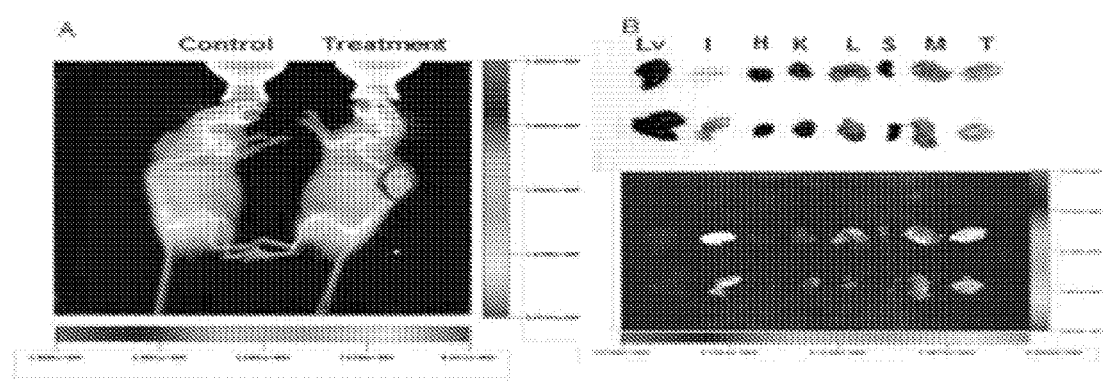
FIG. 37. In vive binding and entry of pRNA nanoparticles into targeted cells. (A) whole body imaging of pRNA nanoparticles target FA tumor xenografts on systemic administration in nude mice. Treatment group is injecting pRNA nanoparticle with Alex647 labeling. Control group is injecting PBS. (B) Organ imaging of pRNA nanoparticles target FA tumor (Lv, liver; K, kidney, H, heart; L, lung; S, spleen; I, intestine; M, muscle; T, tumour).

The sequences for the siRNA, HBV ribozyme, malachite green (MG) binding aptamer and folate labeled RNA were rationally designed with the sequences of the strands $a_{3WJ}$, $b_{3WJ}$, and $c_{3WJ}$, respectively (FIG. 15, FIG. 30). Therapeutic 3WJ-folate-ribozyme-siRNA or 3WJ-folate-aptamer-siRNA was assembled from four individual fragments including a 26-nt folate labeled RNA (Trilink) or folate-DNA strand (synthesized in house); and, chemically synthesized 21-nt siRNA or scramble siRNA anti-sense strand (IDT). The 106-nt strand harboring HBV ribozyme sequence or 96-nt strand harboring MG binding aptamer and the 41-nt strand holding the folate-DNA/RNA were transcribed from DNA template amplified by PCR (FIG. 30). Fluorescent dyes were labeled on the 106-nt RNA strand by using the Label IT® siRNA Tracker Intracellular Localization Kit. Cy™3 (Mirus Bio LLC). The four RNA strands were mixed after purification in TMS buffer at equal molar ratio and then heated up to 80° C. for 5 mins, followed by slow cooling to 4° C. The assembled nanoparticles were then purified from 8% native PAGE gel.

Assessment of Dissociation Conditions of pRNA Nanoparticles by Radiolabel Chasing and Competition Assays.

The stability of the dimer, trimer, and the tri-star 3WJ-3pRNA were evaluated by radiolabel chasing and competition assays using [$\alpha$-$^{32}$P] labeled RNA.

Dilation Assay to Test Dissociation at Extremely Low Concentrations:

purified [$\alpha$-$^{32}$P]3WJ-3pRNA complexes were serial diluted from 40 nM to 160 pM in TMS buffer, and then loaded onto 8% PAGE gel in TBM buffer for autoradiograph.

Competition Assay:

The amount of [$\alpha$-$^{32}$P] labeled 3WJ-3pRNA nanoparticles was kept constant in each lane at 10 nM. Varying concentrations (10 μM-128 pM) of unlabeled pRNA (one of the three strands) were incubated with the labeled 3WJ-3pRNA complex. The samples were then loaded onto 8% native PAGE gel for autoradiograph.

Stability Assay by Urea Denaturation.

The dimer, trimer, and the tri-star 3WJ-3pRNA nanoparticles (0.2 pM each) were assessed in 8% PAGE gel with varying concentrations of urea (0-10M). The loading buffer also contained the same concentration of urea.

Stability Assay in Serum for RNase Stability.

RNA nanoparticles were synthesized in the presence 2'-F dCTP and dUTP, and incubated in RPMI-1640 medium containing 10% fetal bovine serum (Sigma). 200 ng of samples were taken at 10 mins, 1 hr, 12 hr, and 36 hr time points after incubation at 37° C., followed by analysis using 8% native PAGE gel.

Flow Cytometry Analysis of Folate Mediated Cell Binding.

KB cells were maintained in folate-free RPMI-1640 medium (Gibco), then trypsinized and rinsed with PBS. 200 nM Cy3 labeled folate-3WJ-3pRNA-siRNA and the folate-free control NH$_2$-3WJ-siRNA were each incubated with the 2×10$^5$ KB cells at 37° C. for 1 hr. After washing with PBS (137 mM NaCl, 2.7 mM KCl, 100 mM Na$_2$HPO$_4$, 2 mM KH$_2$PO$_4$, pH7.4), the cells were resuspended in PBS buffer. Flow Cytometry (Beckman Coulter) was used to observe the cell binding efficacy of the 3WJ-RNA nanoparticles.

Confocal Microscopy.

Cells were grown on glass coverslides in folate free medium overnight. Cy3 labeled folate-3WJ-3pRNA-siRNA and the folate-free control NH$_2$-3WJ-siRNA were each incubated with the cells at 37° C. for 2 hrs. After washing with PBS, the cells were fixed by 4% paraformaldehyde and stained by Alexa Fluor® 488 phalloidin (Invitrogen) for cytoskeleton and TO-PRO®-3 iodide (642/661) (Invitrogen) for nucleus. The cells were then assayed for binding and cell entry by Zeiss LSM 510 laser scanning confocal microscope.

Activity Assay for the HBV Ribozyme Incorporated in the RNA Nanoparticles.

Figure 22:
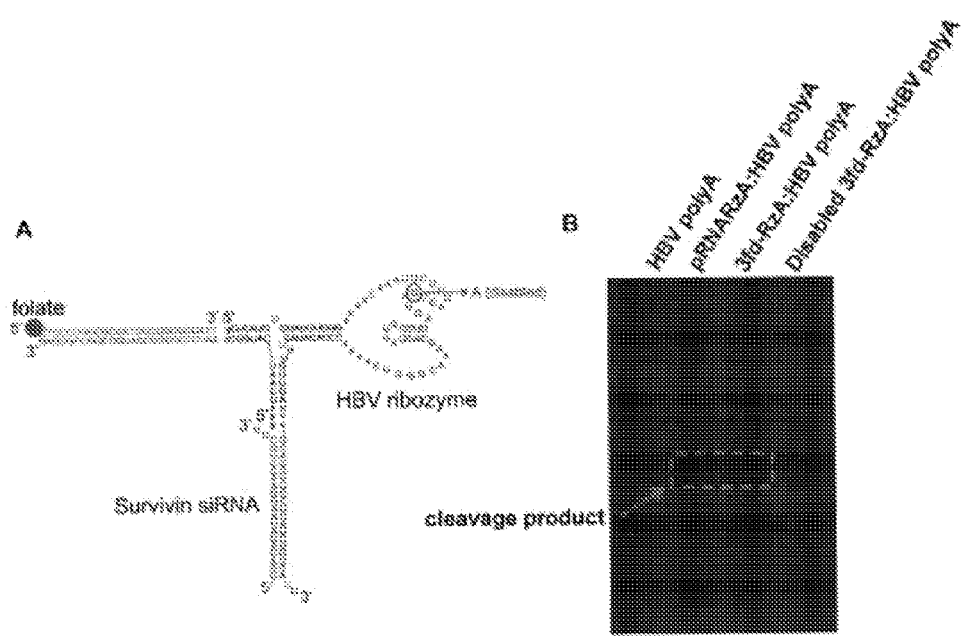
FIG. 22. [$^{32}$P]-assay for assessing the catalytic activity of the HBV ribozyme Incorporated into the therapeutic tri-star RNA nanoparticles by 8% Urea PAGE gel. HBV, hepatitis B virus.

HBV ribozyme is an RNA enzyme that cleaves the genomic RNA of the Hepatitis B Virus genome. The HBV genomic RNA substrate was radiolabeled by [$\alpha$-$^{32}$P] UTP (PerkinElmer, Inc) and incubated with the tri-star harboring HBV ribozyme at 37° C. for 60 mins. pRNA/HBV ribozyme served as a positive control and a disabled ribozyme with a point mutant (G→A, see FIG. 22) was used as a negative control. The samples were then loaded on 8% PAGE/8M urea-denaturing gel for autoradiograph.

Binding Assay for the Malachite Green (MG) Aptamer Incorporated in the Tri-Star RNA Nanoparticles.

Tri-star RNA harboring MG binding aptamer (1 μM) was mixed with MG (1 μM) in 100 mM KCl, 5 mM MgCl$_2$, and 10 mM HEPES (pH 7.4) and incubated at room temperature for 30 mins. The fluorescence was measured using a fluorospectrometer (Horiba Jobin Yvon; SPEX Fluolog-3), excited at 470 nm and scanned from 540 to 800 nm for emission.

Assay for the Silencing of Genes in Cancer Cell Model.

Two 3WJ-RNA constructs were assayed for the subsequent gene silencing effects: one harboring folate and survivin siRNA [3WJ-RNA(FA-siSur)]; and, the other harboring folate and survivin siRNA scramble control [3WJ-RNA(FA-scramble)].

KB cells were transfected with 25 nM of the individual 3WJ-RNAs and a positive siRNA control (Ambion, Inc.) using Lipofectamine 2000 (Invitrogen). After 48 hrs treatment, cells were collected and target gene silencing effects were assessed by both qRT-PCR and Western Blot assays.

Cells were processed for total RNA using illustra RNAspin Mini kits (GE Healthcare). The first cDNA strand was synthesized on mRNA (500 ng) from KB cells with the various 3WJ-RNAs treatment using SuperScript™ III First-Strand Synthesis System (Invitrogen). Real-time PCR was performed using Roche Universal Probe Library Assay. All reactions were carried out in a final volume of 10 μl and assayed in triplicate.

Primers for human GAPDH and survivin were:

```
SEQ. ID. NO: 22: GAPDH left:
5'-AGCCACATCGCTCAGACAC-3';

SEQ. ID. NO: 23: GAPDH right:
5'-GCCCAATACGACCAAATCC-3';

SEQ. ID. NO: 24: Survivin left:
5'-CACCGCATCTCTACATTCAAGA-3';

SEQ. ID. NO: 25: Survivin right:
5'-CAAGTCTGGCTCGTTCTCAGT-3'.
```

PCR was performed on LightCycler 480 (Roche) for 45 cycles. The data were analyzed by the comparative $C_T$ Method ($\Delta\Delta C_T$ Method).

Cells were lysed by RIPA lysis buffer (Sigma) and the cell total protein was extracted for the assay. Equal amounts of proteins were then loaded onto 15% SDS-PAGE and electrophoretically transferred to Immun-Blot PVDF membranes (Bio-Rad). The membrane was probed with survivin antibody (R&D) (1:4000 diluted) and β-actin antibody (Sigma) (1:5000 diluted) overnight, followed by 1:10000 anti-rabbit secondary antibody (Millipore) for 1 hr. Membranes were blotted by ECL kits (Millipore) and exposed to film for autoradiography.

AFM Imaging.

RNA was imaged using specially modified mica surfaces (APS mica) with MultiMode AFM NanoScope IV system (Veeco/Digital Instruments, Santa Barbara, Calif.), operating in tapping mode.

In Vivo Stability and Systemic Pharmacokinetic Analysis in Animals.

Each mouse was injected via the tail vein with 150 μg (6 mg/kg) of AlexaFluor647-labeled pRNA nanoparticles that contain the trifurcate domain as a scaffold. DY647-labeled siRNA with equal molar concentration (40 μg/mice or 1.6 mg/kg) was used as a control. Up to 20 μl of blood samples were collected via the lateral saphenous vein at 1, 4, 8, 12, 16, and 24 hours post injection. Blood samples were collected in BD Vacutainer® SST™ Serum Separation Tubes, and samples were mixed by inverting the tubes five times, and kept for 30 minutes at room temperature. After clotting, serum was collected by centrifugation at 1000-1300 g for 10 minutes. Each 2 μl of serum was mixed with 1 μl of protein-ase-K and 37 μl of water, and incubated at 37° C. for 30 minutes before loading for capillary gel electrophoresis (CGE-Beckman Coulter, dsDNA 1000 Kit), for measuring the fluorescence intensity using a P/ACE MDQ capillary electrophoresis system, equipped with a 635 nm laser (Beckman Coulter, Inc., Fullerton, Calif.). Samples were loaded into a 32 cm×100 μm capillary, by voltage injection for 40 second at 4 kV, and ran for 25 mins at 7.8 kV. The results were integrated using the software "32 Karat" version 7 (Beckman Coulter). The pRNA concentration was calculated from a standard curve. The serum concentration profiles were fitted with an IV bolus non-compartmental model using the Kinetica program (Fisher Scientific, Inc.) to deduce the key secondary pharmacokinetic parameters including $T_{1/2}$ AUC (area under the curve), $V_d$ (volume of distribution), Cl (clearance), and MRT (mean residence time).

Animal Trial: In Vivo Targeting of Tumor Xenograft by Systemic Injection of Fluorescent-Folate (FA)-pRNA Nanoparticle.

For biodistribution, stability assay and specific tumor targeting studies on pRNA nanoparticles with the trifurcate domain as a scaffold, 6-week-old male nude mice (nu/nu) (NCI/Frederick) were fed a folate-free diet for a total of 2 weeks before the experiment. The mice were injected with cancer cells (KB cells ~3×10$^6$ cells per mouse) in a 40% matrigel in a folate free RPMI-1640 medium. When the tumors grew up to about 500 mm$^3$, the mice were injected intravenously through the tail vein with a single dose of 600 μg of FA-AlexaFluor647-labeled pRNA nanoparticle (about 15 nmol in PBS buffer, equal to 24 mg/kg). After 24 hours post injection, the mouse was euthanized by $CO_2$ asphyxiation. Whole-body imaging was carried out with an IVIS® Lumina station with the body of the mouse lying sideways in the imaging chamber. After whole-body imaging, the tumors, liver, spleen, heart, lung, intestine, kidney, and skeleton muscle of the mice were dissected and individually imaged.

In Vitro Synthesis and Purification of RNA Strands for Nanoparticle Assembly

The pRNA were synthesis by enzymatic methods as described previously. Short DNA and RNA oligos were synthesized chemically by IDT (Iowa).

To assemble hand-in-hand pRNA nanoparticles, the homodimers and hetero-monomers of pRNA were transcribed from DNA template generated by PCR following sequences in Table. 1.

To assemble foot-to-foot pRNA nanoparticles, the 7Ba' pRNA with 3'-end palindrome sequences was transcribed from DNA template generated by PCR following sequences of SEQ. ID. NO: 26:

5'GGAAUGGUACGGUACUUCCAUUGUCAUGUGUAUGUUGGGAUUAA

CAGGCACUGAUUGAGUUCAGCCCACAUACUUUGUUGAUUGUCCACUG

UCAAUCAUGGCAAAAGUGCACGCUACUUUCC*CGAUCG*3'.

The arm-on-arm branched pRNA nanoparticles were assembled from RNA strands transcribed from DNA template generated by PCR following sequences in Table. 2.

Assay pRNA Polyvalent Nanoparticles Formation Via Hand-in-Hand Interaction n Native PAGE Higher ordered pRNA polyvalent nanoparticles formation was assay by mixing required heter-monomers at equal molar ratio and then incubating in TMS buffer at 37° C. for 1 hr (Dimer: 7Ab'-7Ba'; Trimer: 7Ba'-7Cb'-7Ac'; Tetramer: 7Ba'-7C'-7Dc'-7Ad'; Pentamer: 7Ba'-7Cb'-7Dc'-7Fd'-7Af'; Hexamer: 7Ba'-7Cb'-7Dc'-7Ed'-7Fe'-7Af'; Heptamer: 7Ba'-7Cb'-7Dc'-7Ed'-7Fe'-7Gf'-7Ag'), followed by 6% native PAGE gel by running in TBM buffer (89 mM Tris, 200 mM Boric Acid, 5 mM MgCl2, pH 7.6) for 3~4 hrs at 4° C. Each polyvalent nanoparticles formation was visualized by ethidium bromide.

Assay pRNA Polyvalent Nanoparticles Formation Via Foot-to-Foot Interaction in Native PAGE The formation of the foot-to-foot complexes were accomplished by extending 3'-end of one loop extended pRNA heter-monomers with palindrome sequence (5' CGAUCG 3'). All the RNA hetero-monomers required for assembling each polyvalent nanoparticles were mixed at equal molar ratio and then incubating in TMS buffer at 37° C. for 1 hr and then analyzed by 4% native PAGE in TBM running buffer, as specified in the Results Section. After running at 4° C. for 4-5 hrs, the RNA was visualized by ethidium bromide.

Formation of pRNA Nanoparticles with Functional Moieties.

Higher ordered pRNA polyvalent nanoparticles formation was assay by mixing required heter-monomers at equal molar ratio and then incubating in TMS buffer at 37° C. for 1 hr (Dimer: 7Ab'-7Ba'; Trimer: 7Ba'-7Cb'-7Ac'; Tetramer: 7Ba'-7Cb'-7Dc'-7Ad'; Pentamer: 7Ba'-7Cb'-7Dc'-7Fd'-7Af'; Hexamer: 7Ba'-7Cb'-7Dc'-7Ed'-7Fe'-7Af'; Heptamer: 7Ba'-7Cb'-

7Dc'-7Ed'-7Fe'-7Gf'-7Ag'), followed by 6% native PAGE gel by running in TBM buffer (89 mM Tris, 200 mM Boric Acid, 5 mM MgCl2, pH 7.6) for 3-4 hrs at 4° C. Each polyvalent nanoparticles formation was visualized by ethidium bromide.

AFM Imaging

For all samples specially modified mica surfaces (APS mica) were used. The APS mica was obtained by incubation of freshly cleaved mica in 167 nM 1-(3-aminopropyl) silatrane. The details of APS mica surface modification is described elsewhere (6811, 6812). The native PAGE purified RNA samples were diluted with 1×TMS buffer to a final concentration of 3-5 nM. Then, the droplet of samples (5-10 uL) was immediately deposited on APS mica. After 2 min incubation on the surface, excess samples were washed with DEPC treated water and dried under a flow of Argon gas. AFM images in air were acquired using MultiMode AFM NanoScope IV system (Veeco/Digital Instruments, Santa Barbara, Calif.) operating in tapping mode. Two type of AFM probes were used for tapping mode imaging in air: (1) regular tapping Mode Silicon Probes (Olympus from Asylum Research, Santa Barbara, Calif.) with a spring constant of about 42 N/m and a resonant frequency between 300-320 kHz. (2) non-contact NSG01_DLC probes (K-Tek Nanotechnology, Wilsonville, Oreg.) with a spring constant of about 5.5 N/m and a resonance frequency between 120-150 kHz.

Assay of Each Functionalities within pRNA Nanoconstructs

Binding assay for the MG aptamer incorporated into pRNA nanoparticles: pRNA tetramer harboring MG binding aptamer and the monomer subunit harboring MG binding aptamer (100 nM) was mixed with MG (2 µM) in binding buffer containing 100 mM KCl, 5 mM $MgCl_2$, and 10 mM HEPES (pH 7.4) (6817, 6818) and incubated at room temperature for 30 mins. RNA tetramer without MG binding aptamer served as negative control. MG binding aptamer itself served as the positive control. The fluorescence intensity was measured using a fluorospectrometer (Horiba Jobin Yvon; SPEX Fluolog-3), excited at 615 nm (scanning from 625 to 800 nm for emission). The same samples can also nm into 6% native PAGE in TBM running buffer at 4° C. for 3~4 hrs. After stain the gel with 5~10 µM MG in binding buffer, the MG signal can be excited and imaged by Typhoon FLA 7000 (GE healthcare) at Cy5 channel.

Binding assay for the streptavidin (STV) binding aptamer incorporated into pRNA nanoparticles: The pRNA tetramer harboring STV binding aptamer was premixed and preassembled in PBS buffer with 10 mM Mg2+ before incubation with streptavidin agarose resin (Thermo Scientific) and the streptavidin resin was equilibrated at room temperature and wash with PBS w/10 mM Mg2+ before binding. 50 uL resin each tube was spin down at 500 g for 1 min to remove storage solution. The tetramer harboring STV binding aptamer (total ~4.8 ug) in 10 mM Mg2+PBS was added to incubate with resin at room temperature for 1 hr. Tetramer without STV binding aptamer served as the negative control. After incubation, the resin was spin down again and supernatant was removed to another tube as "passing through". Then, 50 uL PBS buffer containing 10 mM Mg2+ was added to wash the resin for 15 min incubation by 7 times, and all the supernatant after each washing step was kept as "wash 1-7". Finally, RNA was eluted out by 5 mM biotin which can competitively bind to the resin in PBS buffer (10 mM Mg2+). The samples were taken to run the 6% native PAGE in TBM buffer, the RNA was visualized by MG staining or ethidium bromide staining.

Activity assay for the HBV ribozyme incorporated in pRNA nanoparticles: HBV ribozyme is an RNA enzyme that cleaves the genomic RNA of the Hepatitis B Virus genome {2550}. The HBV RNA substrate was fluorescent labeled by Cy3 (Mirus) and incubated with the pRNA tetramer harboring HBV ribozyme (1:2 and 1:4 molar ratio) at 37° C. for 60 mins in a buffer containing 20 mM $MgCl_2$, 20 mM NaCl, and 50 mM Tris-HCl, pH 7.5, respectively. The pRNA/HBV ribozyme served as a positive control {2550}, and pRNA tetramer harboring a disabled HBV ribozyme was used as a negative control. The samples were then loaded on 8M urea/10% PAGE gel and scanned by Typhoon FLA 7000 (GE healthcare) at Cy3 channel.

Confocal microscopy assay folate mediated binding and internalization while conjugating in pRNA nanoparticles: KB or Hela cells were grown on glass coverslides in folate free medium overnight. 200 nM Cy3 labeled 3WJ pRNA nanoparticle harboring folate labeled and the folate-free control were each incubated with the cells at 37° C. for 2 hrs. After washing with PBS, the cells were fixed by 4% paraformaldehyde and stained by Alexa Fluor® 488 phalloidin (Invitrogen) for cytoskeleton and TO-PRO®-3 iodide (642/661) (Invitrogen) for nucleus. The cells were then assayed for binding and cell entry by Zeiss LSM 510 laser scanning confocal microscope.

Assay for the silencing of luciferase genes in cancer cell model: Dual-luciferase assay was used to test the potential of the pRNA tetramer escorting siRNA delivered into cells. For dual-luciferase assays, Hela cells were seeded in 24-well plates. Gene silencing assays were performed by co-transfecting 1.25 nM pRNA tetramer harboring different copies of firefly luciferase siRNA with both plasmid pGL-3 control and pRL-TK (Promega, Madison, Wis.) coding for firefly and renilla luciferase, respectively. The latter served as an internal control to normalize the luciferase data (Dual-Luciferase Reporter Assay System; Promega). The pRNA tetramer harboring random sequences served as the negative control. The target firefly luciferase siRNAs was from literature {7111}. Cells were washed once with phosphate-buffered saline (PBS) and lysed with passive lysis buffer. The plates were shaken for 15 minutes at room temperature. 20 µl of lysate were added to 50 µl of luciferase assay reagent (LAR II) in 96-well white plate (Thermo Scientific) and firefly luciferase activity was measured using Synergy 4 plate reader (Bioteck). Upon addition of 50 µl of Stop & Glo Reagent, control measurements of renilla luciferase activity were then obtained. The data was then normalized with respect to the renilla activity for determining the average ratio of firefly to renilla activity over several trials.

Animal Trial: In Vivo Targeting of Tumor Xenografts by Systemic Injection of pRNA Nanoparticle 7 weeks old of NOD/SCID IL2R null male mice were injected 5×106 KB cells and maintained 3 weeks to allow tumor engraftment. Tumor was apparent ~2 weeks after xenograft injection of KB tumor cells under the skin. Three weeks prior to injection of nanoparticle, mice were maintained on a folate free diet, after which NOD/SCID IL2R null mice with KB tumor were injected with 250 µM (76 µl) X-shaped pRNA nanoparticles with folate and Alex647 labeling through the tail-vein. Control mice were injected with 76 µl PBS. Mice were euthanized 24 hours after injection and whole body imaging was conducted using Kodak Carestream MultiSpectral FX with added multi-angle 2D performance Station. Following whole-body imaging, the mice were dissected and the major organs were isolated for imaging.

Example 2

Construction of Trifurcate Domain and its Derivatives from Phi29 pRNA

Unusual Properties Displayed by the Trifurcate Domain Assembled from Three RNA Oligos.

Figure 9:
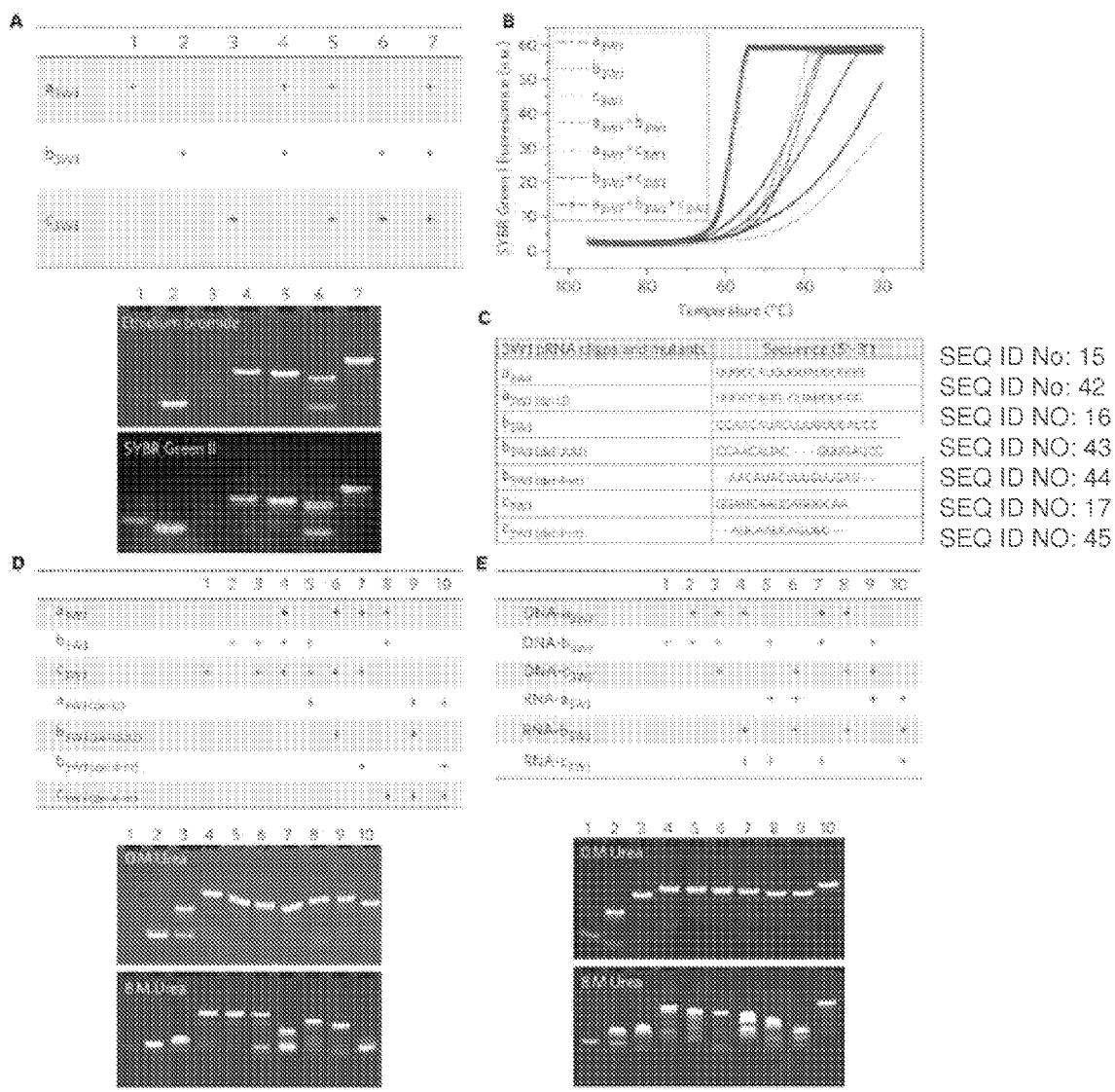
FIG. 9. Assembly and stability studies of 3WJ-pRNA. In the tables, '+' indicates the presence of the strand in samples of the corresponding lanes. (A) 15% native PAGE showing the assembly of the 3WJ core, stained by ethidium bromide (upper) and SYBR Green II (lower). (B) Tm melting curves for the assembly of the 3WJ core. Melting curves for the individual strands (brown, green, silver), the two-strand combinations (blue, cyan, pink) and the three-strand combination (red) are shown. (C) Oligo sequences of 3WJ-pRNA cores and mutants. 'del U', deletion of U bulge; 'del UUU', deletion of UUU bulge; 'del 4-nt', deletion of two nucleotides at the 3' and 5' ends, respectively. (D) Length requirements for the assembly of 3WJ cores and stability assays by urea denaturation. (E) Comparison of DNA and RNA 3WJ core in native and urea gel.

The trifurcate domain of phi29 pRNA was constructed using three pieces of RNA oligos denoted $a_{3WJ}$, $b_{3WJ}$, and $c_{3WJ}$ (FIG. 1D). Two of the oligos $a_{3WJ}$ and $c_{3WJ}$ were resistant to staining by ethidium bromide (FIG. 9A). Using SYBR Green II RNA gel stain, $a_{3WJ}$ could be weakly stained, while $c_{3WJ}$ remained unstainable (FIG. 9A). Ethidium bromide is an intercalating agent; generally, it can stain dsRNA and dsDNA as well as ssRNA containing secondary structures or base-stacking. SYBR Green II is well known for its ability to stain both single-stranded and double-stranded RNA or DNA. The absence of staining, particularly in $c_{3WJ}$ indicates an unusual structural property.

The mixing of the three oligos $a_{3WJ}$, $b_{3WJ}$, and $c_{3WJ}$ at 1:1:1 stoichiometric ratio at room temperature resulted in unusually high efficient formation of the trifurcate domain without leaving any detectable unassembled oligos at 100 µM. Generally. RNA folding requires magnesium; however, in this case magnesium was not required for complex assembly, and the trifurcate domain remained stable without dissociating at room temperature for weeks (data not shown). If one of the oligos was omitted (FIG. 9A, lanes 4-6), dimers were observed, as exhibited by faster migration rates compared to the trifurcate domain (FIG. 9A, lane 7). Generally, dsDNA and dsRNA are denatured and dissociate in presence of 5M or 7M urea. Surprisingly, in the presence of 8M urea, the trifurcate domain remained stable and did not show any signs of dissociation (FIG. 8D). The complex was even resistant to 10M urea, the highest urea concentration that could be feasibly tested, thereby demonstrating its robust nature.

Length Requirements of the Helical (H) Region of the Three Branches for the Stable Formation of the Trifurcate Domain Under Strongly Denaturing Conditions.

The length of the helices for H1, H2 and H3 were 8, 9, and 8 base pairs, respectively. RNA complexes with the deletion of 2 base-pairs in H1 and H3 (FIG. 1D, FIG. 9C) had no effect on the stability (FIG. 9D, lanes 8, 9). However, deletion of 2 base-pairs at H2 (FIG. 1D), did not affect the formation of the complex, but made the trifurcate domain unstable in the presence of 8M urea with dissociation observed (FIG. 9D, lanes 7, 10). According to non-limiting theory, these results demonstrate that while 6 base pairs were sufficient in two of the stem regions (H1 and H3), 8 bases were preferred for H2 to keep the junction domain stable under strong denaturing conditions.

Comparison of DNA and RNA Trifurcate Domains.

To further evaluate the chemical and thermodynamic properties of the trifurcate domain of phi29 pRNA, the same sequences were used to construct a DNA trifurcate domain. In a native gel, when the three DNA oligos were mixed in a 1:1:1 stoichiometric ratio, the trifurcate domain assembled, as demonstrated by similar gel mobility compared to RNA trifurcate domain (FIG. 9E). However, the DNA trifurcate complex dissociated in the presence of 8M urea (FIG. 9E, bottom). DNA/RNA hybrid trifurcate domains exhibited increasing stability as more RNA strands were incorporated. According to non-limiting theory, by controlling the ratio of DNA to RNA in the trifurcate domain region, the stability of the complex can be tuned accordingly.

Extension of the Trifurcate Domain into Larger Structures with Three Branches.

Figure 27:
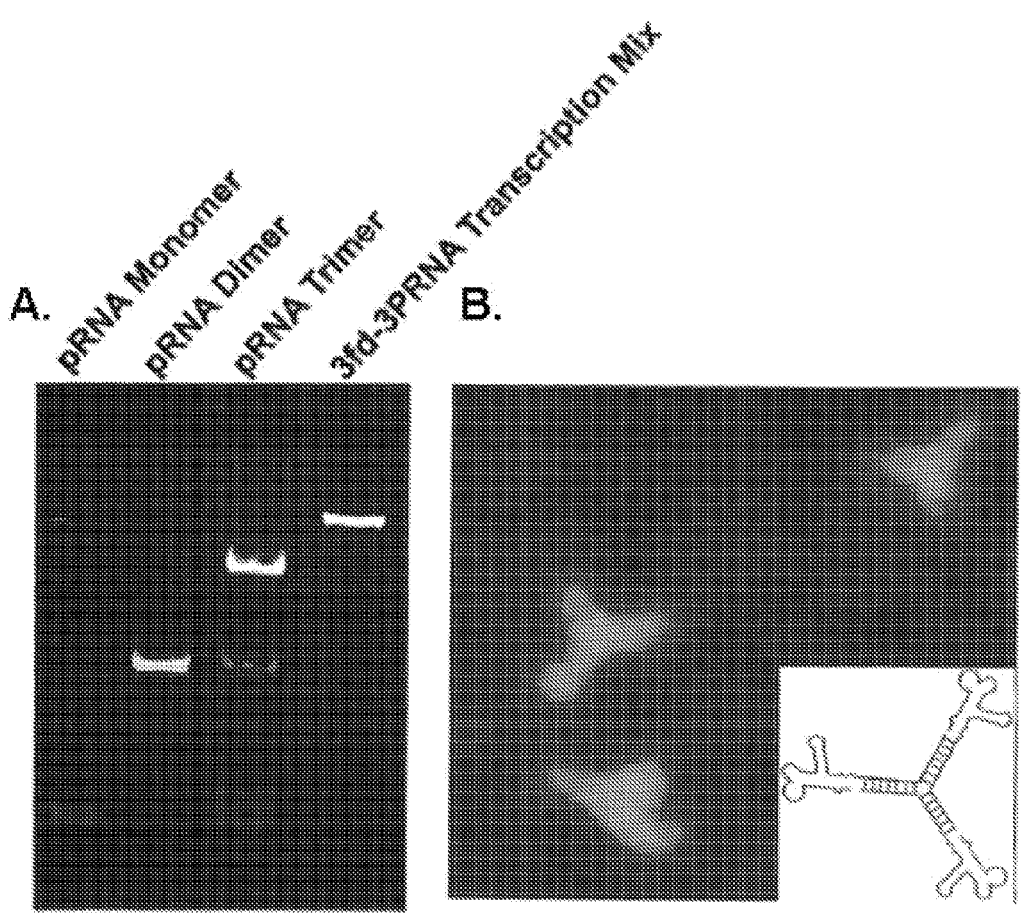
FIG. 27. Formation of tri-star RNA nanoparticles 3WJ-3pRNA In one step during transcription carrying three pRNA molecules using the trifurcate core. The sequences of each of the three RNA oligos $a_{3WJ}$, $b_{3WJ}$, and $c_{3WJ}$ were placed at the 3'-end of the pRNA monomer Ab' and the complex assembled into a three-way branched nanoparticles harboring one pRNA at each arm (lane 4), as demonstrated by 8% native PAGE gel (A) and AFM (B). Insert: A schematic of the assembled 3WJ-3pRNA.
Figure 28:
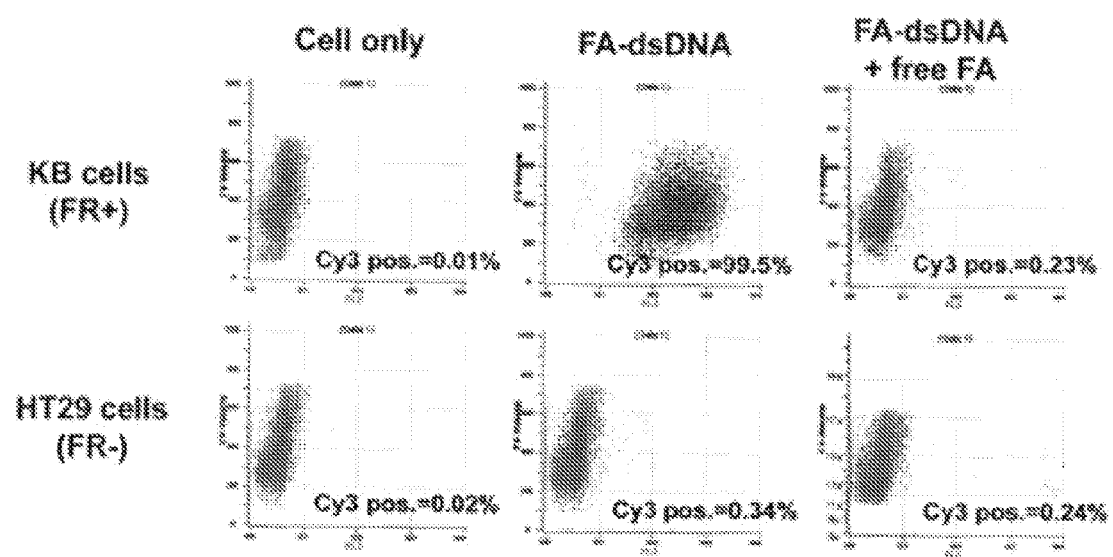
FIG. 28. Folate labeled particle specifically target folate receptor positive cell lines. The folate receptor positive KB cell line (FR+) showed 99.5% folate-RNA binding compared to the folate receptor negative HT29 cell line (FR-). Free folate competed the strong binding of folate-RNA to KB cells indicated the specificity.

It has been previously demonstrated that the extension of the phi29 pRNA at the 3'-end does not affect the folding of pRNA global structure. The sequences of the three RNA oligos $a_{3WJ}$, $b_{3WJ}$, and $c_{3WJ}$, were placed at the 3'-end of the pRNA monomer, Ab'. Mixing of the three resulting pRNA chimeras containing $a_{3WJ}$, $b_{3WJ}$, and $c_{3WJ}$ sequences respectively, at equimolar concentrations led to the assembly of three-way branched nanoparticles harboring one pRNA at each branch (denoted as, tfd-3pRNA). AFM images strongly confirmed the formation of larger RNA complexes with three-branches (FIG. 1E), which were consistent with gel shift assays. The 3WJ-3pRNA nanoparticles could also be co-transcribed and assembled in one step during transcription with high yield (FIG. 27).

Determination of Dissociation of the Larger Structure with Three Branches at Extremely Low Concentration.

When RNA nanoparticles are delivered systemically to the body, the particles will exist in low concentrations due to dilution by circulating blood. Only those RNA particles that are not dissociated at low concentrations can be considered as therapeutic agents for systemic delivery.

To determine whether the larger RNA nanoparticle structures assembled with trifurcate RNA junction domains and having three branches harboring therapeutic functionalities were subjected to dissociation at low concentration, the $[\alpha\text{-}^{32}P]$ labeled 3WJ-3pRNA nanoparticles were serially diluted to extremely low concentrations. It was found that the concentration for dissociation was below the detection limit of the $[^{32}P]$-labeling technology. Even at 160 pM in TMS buffer, the lowest concentration tested, the dissociation of the nanoparticles was undetectable (FIG. 10C).

Assessment of Dissociation Conditions of pRNA Nanoparticles by Radiolabel Chasing and Competition Assays.

To determine the stability of the trifurcate domain harboring pRNA on each branch, a fixed amount (10 nM) of $[\alpha\text{-}^{32}P]$ labeled 3WJ-3pRNA nanoparticles were incubated with varying concentrations (10 µM-128 pM) of unlabeled building blocks of pRNA-$b_{3WJ}$ (FIG. 10A). The interchange of labeled and unlabeled pRNA-$b_{3WJ}$ within the 3WJ-3pRNA nanoparticle was undetectable, even with 1000 fold excess of competitor unlabeled partner, thereby demonstrating the robust and highly stable nature of the nanoparticle. The results from competition experiments as well as dilution assays indicated that the 3WJ-3pRNA nanoparticle was stable enough that its dissociation constant was beyond the detection limit of current dissociation constant measurement techniques using $[\alpha\text{-}^{32}P]$ labeling.

Assessment of the Stability of the Larger pRNA Nanoparticles with Three Therapeutic Branches.

Figure 11:
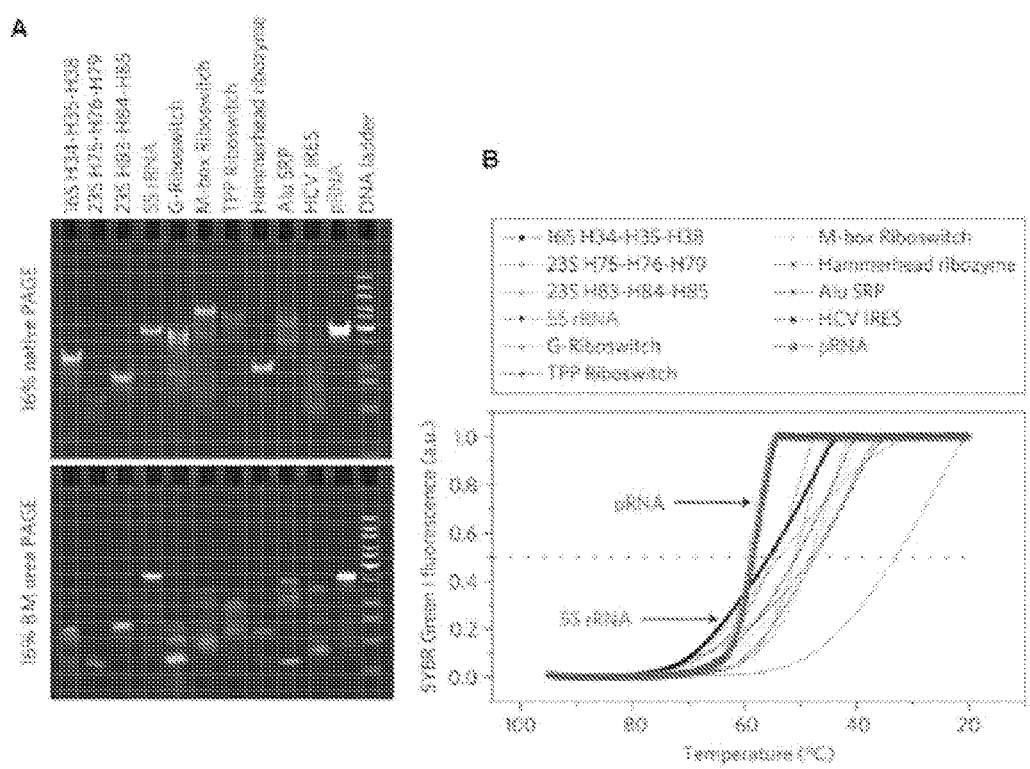
FIG. 11. Comparison of different 3WJ-RNA cores. (A) Assembly and stability of 11 3WJ-RNA core motifs assayed in 16% native (upper) and 16% 8 M urea (lower) PAGE gel. (B) Melting curves for each of the 11 RNA 3WJ core motifs assembled from three oligos for each 3WJ motif under physiological buffer TMS.
Figure 12:
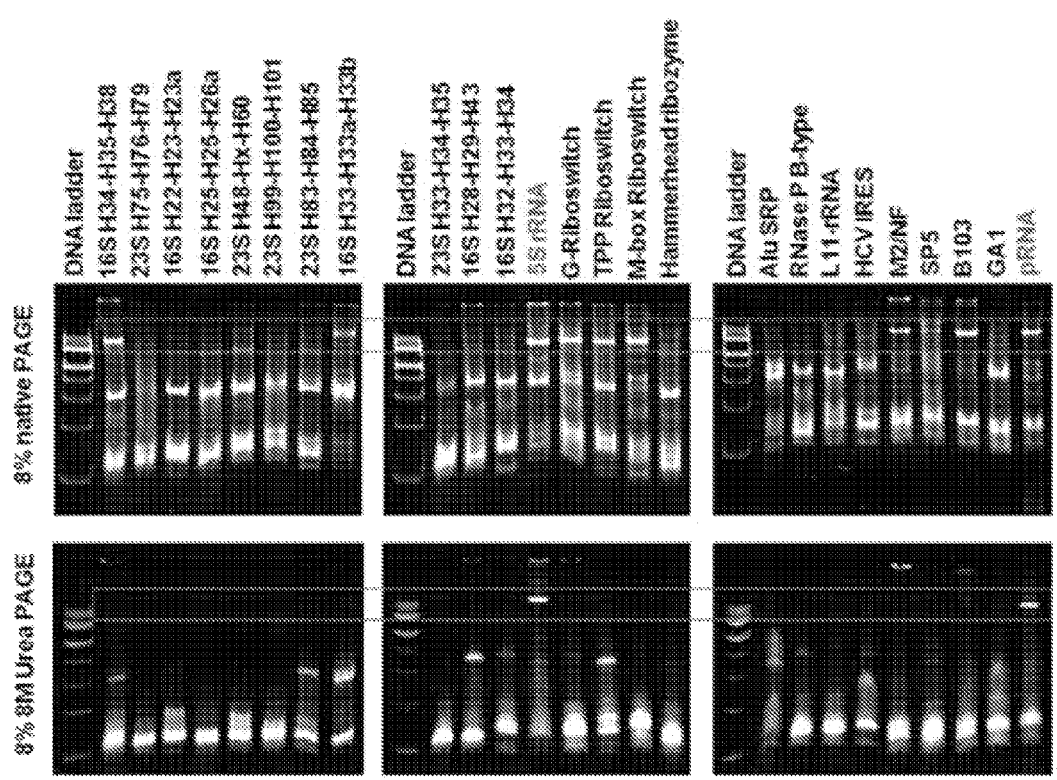
FIG. 12. Assembly and stability of 25 3WJ-3pRNA constructs. Three individual phi29 pRNAs subunits with three protruding ends were used as modules. The sequences of each of the three RNA oligos of the respective 3WJs were placed at the 3'-end of the pRNA monomer Ba' and the complex was assembled into a three-way branched nanoparticles harboring one pRNA at each arm, as demonstrated by 8% native (upper) and 8M Urea (lower) PAGE gel. The bands corresponding to the assembled 3WJ structures are boxed in red.

The 3WJ-3pRNA nanoparticles were assessed by denaturation in polyacrylamide gels containing varying concentrations of urea (0-6M) (FIG. 11B). The data demonstrate that the presently disclosed trifurcate RNA junction domain was stable and resistant to dissociation under denaturing conditions.

The 3WJ-3pRNA with Therapeutic RNA Functionalities Remained Undissociable in the Absence of Magnesium.

Generally, RNA folding requires magnesium concentrations in the tens of millimolar. However, the magnesium concentration is lower than 1 mM in human blood system. Thus. RNA nanoparticles formed at supraphysiological magnesium concentrations in vitro, using multiple subunits, may dissociate when they reach the blood circulatory system. It is therefore desirable to create RNA nanoparticles that are resistant to dissociation in a low-magnesium environment. Surprisingly, the 3WJ-3pRNA composed of three subunits remained intact in the denaturing gel in absence of magnesium. Magnesium was therefore not required for keeping the 3WJ-3pRNA nanoparticles intact.

Construction of a Variety of 3WJ-RNA Therapeutic Nanoparticles Using the Trifurcate Domain as a Scaffold.

Therapeutic RNA nanoparticles were constructed using the herein described trifurcate RNA junction domain as a scaffold (FIG. 15). Each branch of the three-way junction carried one RNA module with a defined functionality, (e.g., cell receptor binding ligand, aptamer, siRNA, ribozyme). The presence of the modules or therapeutic moieties did not interfere with the formation of the trifurcate domain, as demonstrated by AFM imaging (FIG. 15).

Fabrication of Chemically Modified Stable 3WJ-3pRNA Nanoparticles Resistant to Degradation in Serum.

Figure 21:
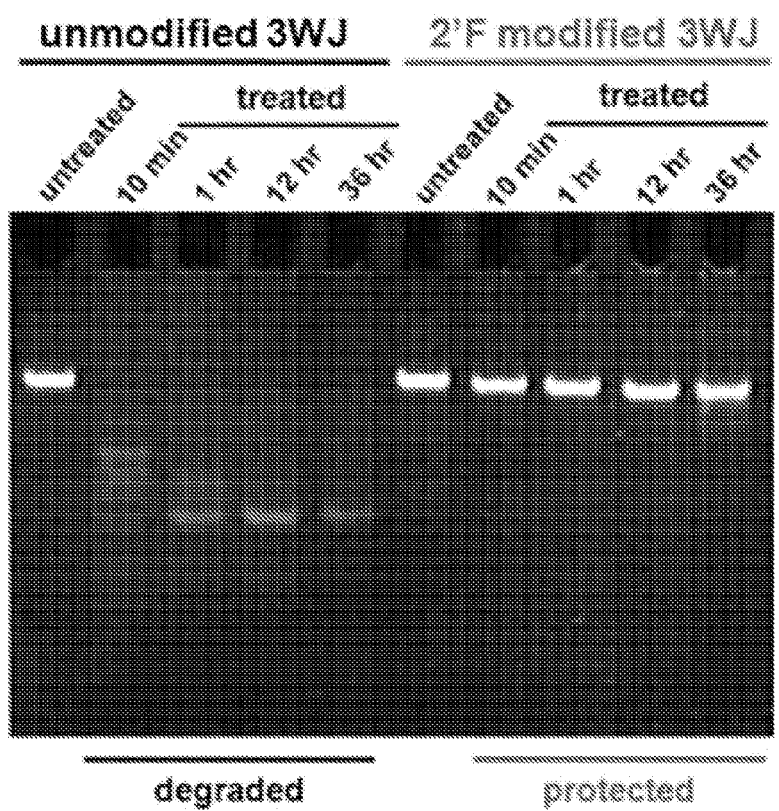
FIG. 21. RNase and serum stability assay of trivalent RNA nanoparticles 3WJ-3pRNA (unmodified and 2'-F modified). RNA nanoparticles were incubated in RPMI-1640 medium containing 10% fetal bovine serum (Sigma). 200 ng of RNA samples were taken at 10 mins, 1 hr, 12 hr, and 36 hr time points after incubation at 37° C., followed by analysis using 8% native PAGE gel.

Nucleotides CTP and UTP with 2'-F modification were mixed with unmodified GTP and ATP during the transcription of the RNA building blocks for the assembly of the 2'F-3WJ-3pRNA (or 3WJ-folate-siRNA-ribozyme) RNA nanoparticles. The resulting 2'F nanoparticles were resistant to degradation in cell culture medium with 10% serum even after 36 hours of incubation, while the unmodified RNA degraded within 10 minutes (FIG. 21).

Retention of Catalytic Activity of the Ribozyme and Fluorescence Emitting Activity of the MG-Binding Aptamer Incorporated in the 3WJ-3pRNA Nanoparticles.

Figure 23:
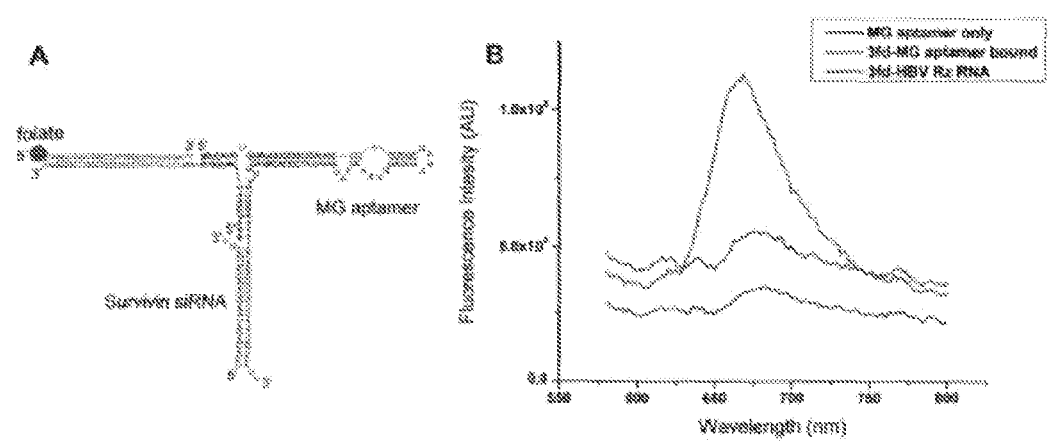
FIG. 23. Functional assay of the MG (malachite green) aptamer incorporated in the tri-star RNA nanoparticles with the trifurcate core. MG is not fluorescent in an unbound configuration. Fluorescent light is only emitted upon binding of the aptamer with the MG FIG. 24. Binding and entry of the 3WJ-RNA into the targeted cells. (A) Flow cytometry data revealed that the folate labeled 3WJ-3pRNA nanoparticles bound and specifically entered the cell with almost 100% binding efficiency. (B) Confocal imaging to examine the binding and entry of the therapeutic tri-star RNA nanoparticles to the targeted KB cancer cells. Entry was shown by the co-localization and overlap of the fluorescent 3WJ-3pRNA RNA nanoparticles (red) and cytoplasma (green).

Testing for the appropriate folding of individual modules within RNA complexes after fusion was performed. To test whether the incorporated RNA moieties retained their original folding and functionality after being fused and incorporated, Hepatitis B virus (HBV) cleaving ribozyme and MG (Malachite Green dye, triphenylmethane) binding aptamer were used as model systems for structure and function verification. The free MG was not fluorescent by itself, but emitted fluorescent light after binding to the aptamer. It was found that the HBV ribozyme was able to cleave its RNA substrate after being incorporated into the nanoparticles (FIG. 22) and that the fused MG-binding aptamer retained its capacity to bind MG, as revealed by its fluorescence emission (FIG. 23). These results confirmed that individual RNA modules fused into the nanoparticles retained their original functional folding after incorporation into the RNA nanoparticles.

Cell Binding and Entry Using the 3WJ-3pRNA Therapeutic Nanoparticles in Cell Culture.

Figure 10:
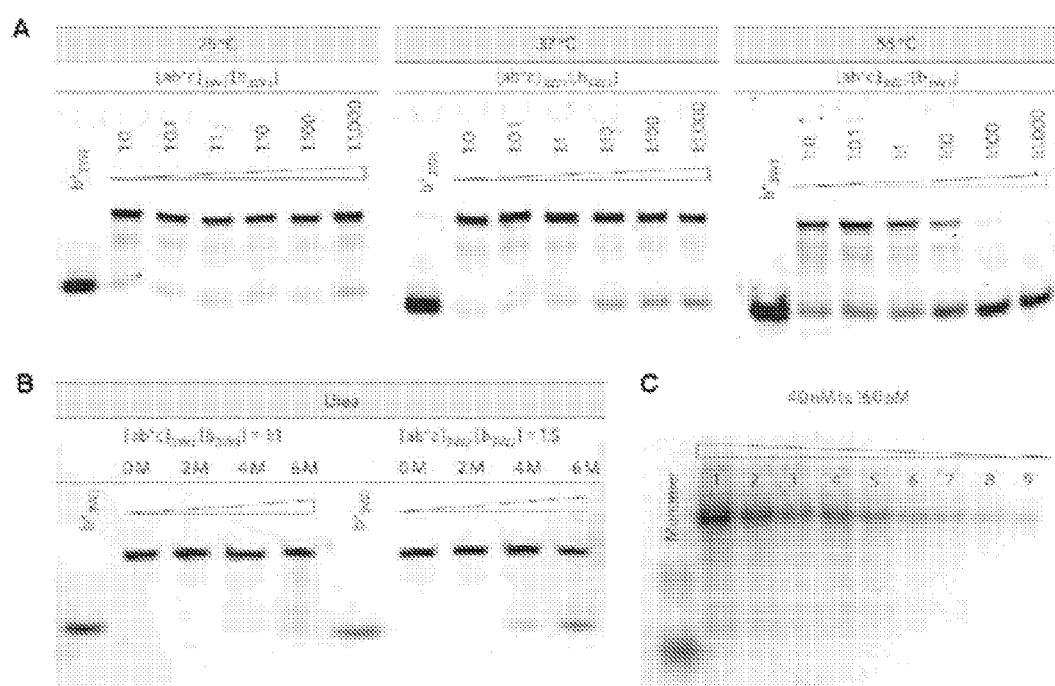
FIG. 10. Competition and dissociation assays of 3WJ-pRNA. (A) Temperature effects on the stability of the 3WJ-pRNA core, denoted as $[ab^*c]_{3WJ}$, evaluated by 16% native gel. A fixed concentration of Cy3-labelled $[ab^*c]_{3WJ}$ was incubated with varying concentrations of unlabelled $b_{3WJ}$ at 25, 37 and 55° C. (B) Urea denaturing effects on the stability of $[ab^*c]_{3WJ}$ evaluated by 16% native gel. A fixed concentration of labelled $[ab^*c]_{3WJ}$ was incubated with unlabelled $b_{3WJ}$ at ratios of 1:1 and 1:5 in the presence of 0-6 M urea at 25° C. (C) Dissociation assay for the [$^{32}$P]-3WJ-pRNA complex harboring three monomeric pRNAs by twofold serial dilution (lanes 1-9). The monomer unit is shown on the left.
Figure 24:
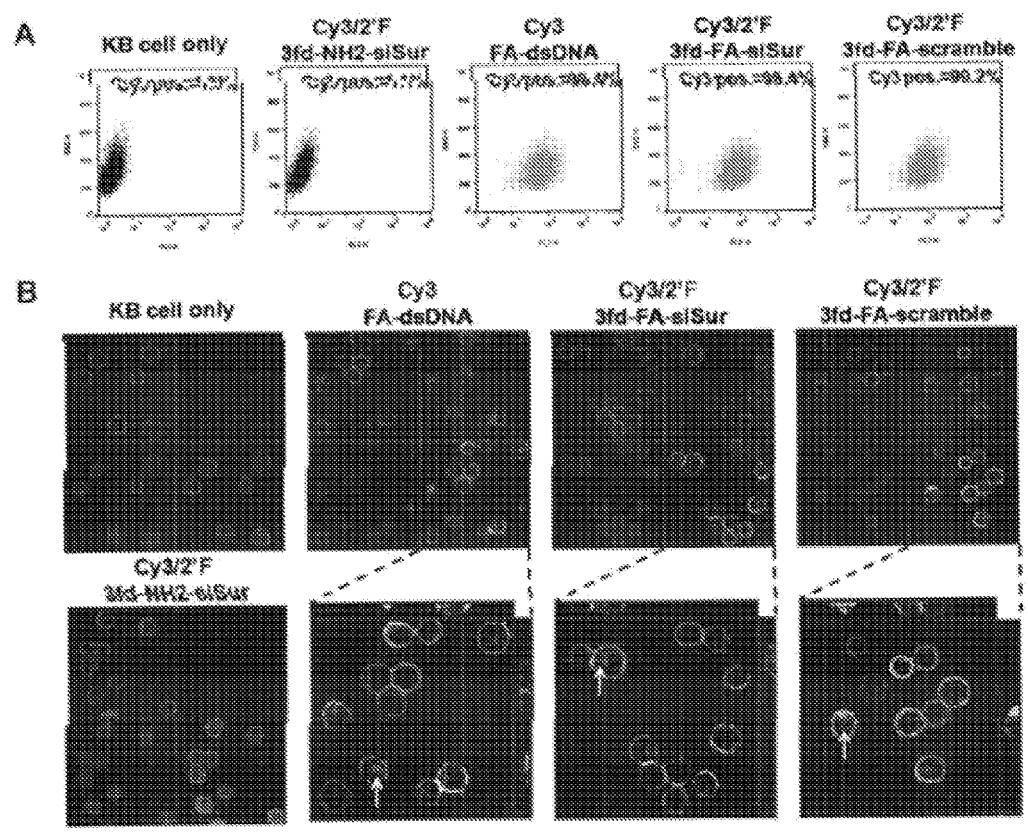

Many kinds of cancer cell lines, especially from the epithelial origin, overexpress the folate receptor on the cell surface; folate receptor expression is typically elevated a thousand-fold. Folate has been used extensively as a cancer cell delivery agent via folate receptor-mediated endocytosis. The fluorescent 3WJ-3pRNA RNA nanoparticles formed using the trifurcate RNA junction domain, with folate conjugated into one of the branches of the RNA complex, were tested for cell binding efficiency. One RNA fragment of 3WJ-3pRNA was labeled with the folic acid for targeted delivery, the second fragment was labeled with Cy3, and the third fragment was fused to the siRNA that can silence the gene of the anti-apoptotic factor. As a negative control, the RNA nanoparticles contained folate and siRNA with a scrambled sequence (no sequence identity with any human gene) to replace the active gene silencing sequence; or a 3WJ-3pRNA nanoparticle was prepared containing the active siRNA, but without folate. Flow cytometry data revealed that the folate labeled 3WJ-3pRNA RNA nanoparticles bound to cells and delivered siRNA to the cells with almost 100% binding efficiency (FIG. 10). Confocal imaging indicated a strong binding of the RNA nanoparticles and efficient entry into the targeted cells, as demonstrated by the excellent co-localization and overlap of the fluorescent 3WJ-3pRNA RNA nanoparticles (red) and cytoplasma (green) (FIG. 24).

Assay for the Targeted Gene Silencing by 3WJ-RNA in Cancer Cell Model.

Figure 25:
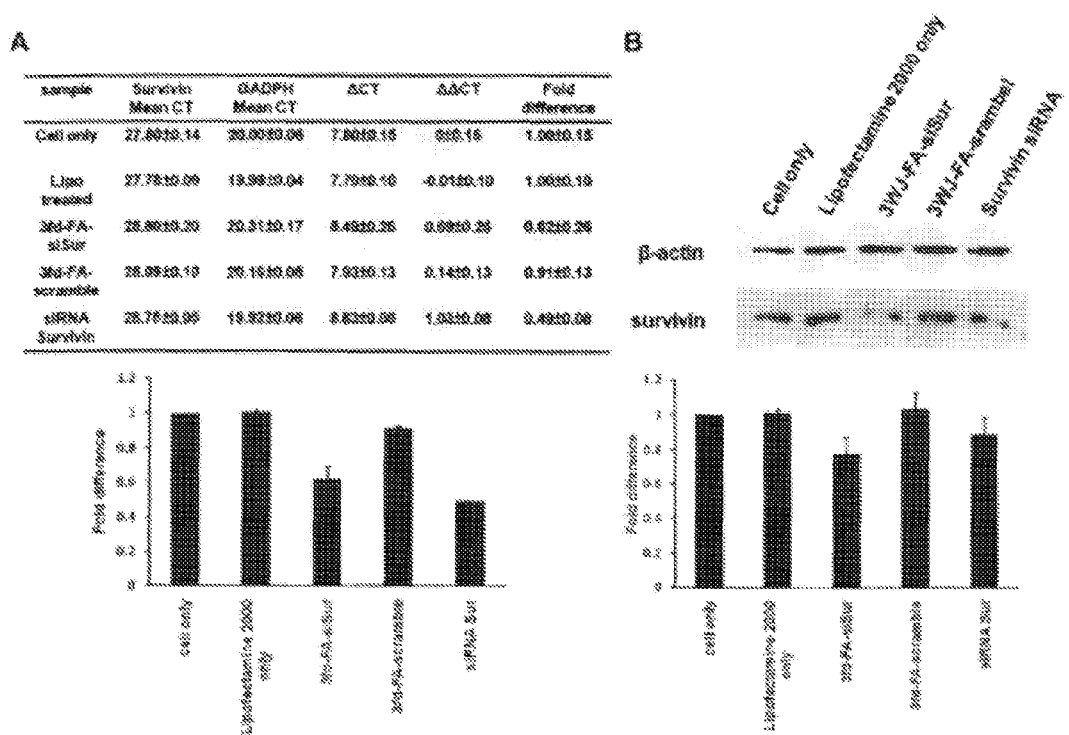
FIG. 25. Gene silencing data. (A) qRT-PCR data showing reduced survivin gene expression on mRNA level. GADPH was chosen to be the endogenous control. (B) Western Blot assay. The β-actin bands were used as the loading control for normalizing the survivin gene expression among different experimental groups.

Two 3WJ-RNAs were constructed using the trifurcate RNA junction domain, for assaying the subsequent gene silencing effects. One of the 3WJ-RNAs harbored folate and survivin siRNA [3WJ-RNA(FA-siSur)], while the other construct harbored folate and a survivin siRNA scrambled-sequence control [3WJ-RNA(FA-scramble)]. After 48 hrs transfection, both qRT-PCR and Western Blot assays confirmed that there was reduced survivin gene expression of 3WJ-FA-siSur compared to the control 3WJ-FA-scramble, on mRNA as well as protein levels. In addition, the silencing potency of the 3WJ-FA-siSur was comparable to the positive survivin siRNA control (FIG. 25).

In Vivo Stability and Systemic Pharmacokinetic Analysis in Animals.

Pharmacokinetic parameters provide information on the stability and behavior of a drug in the in vive environment after administration. Two of the key factors that may affect the pharmacokinetic (PK) profile are metabolic stability and renal filtration. It has been reported that regular siRNA molecules have extremely poor pharmacokinetic properties, since siRNA has a short half-life ($T_{1/2}$) and fast clearance due to both metabolic instability and small size (<10 nm), rendering fast kidney clearance.

The PK profiles of Cy5-2'-F-pRNA nanoparticles that use the trifurcate RNA junction domain as a scaffold were studied in mice by systemic administration of a single intravenous injection via the tail vein, followed by blood collection at time points of 1, 4, 8, 12, 16, and 24 hrs post administration. The concentration of the fluorescent nanoparticle in serum was determined by capillary gel electrophoresis. The half-life ($T_{1/2}$) of the pRNA nanoparticles was determined to be 6.5-12.6 hours, compared to the control 2'-F-modified siRNA, which could not be detected beyond 5 min post-injection, an observation that is close to the 0.25 hour reported in the literature.

Figure 26:
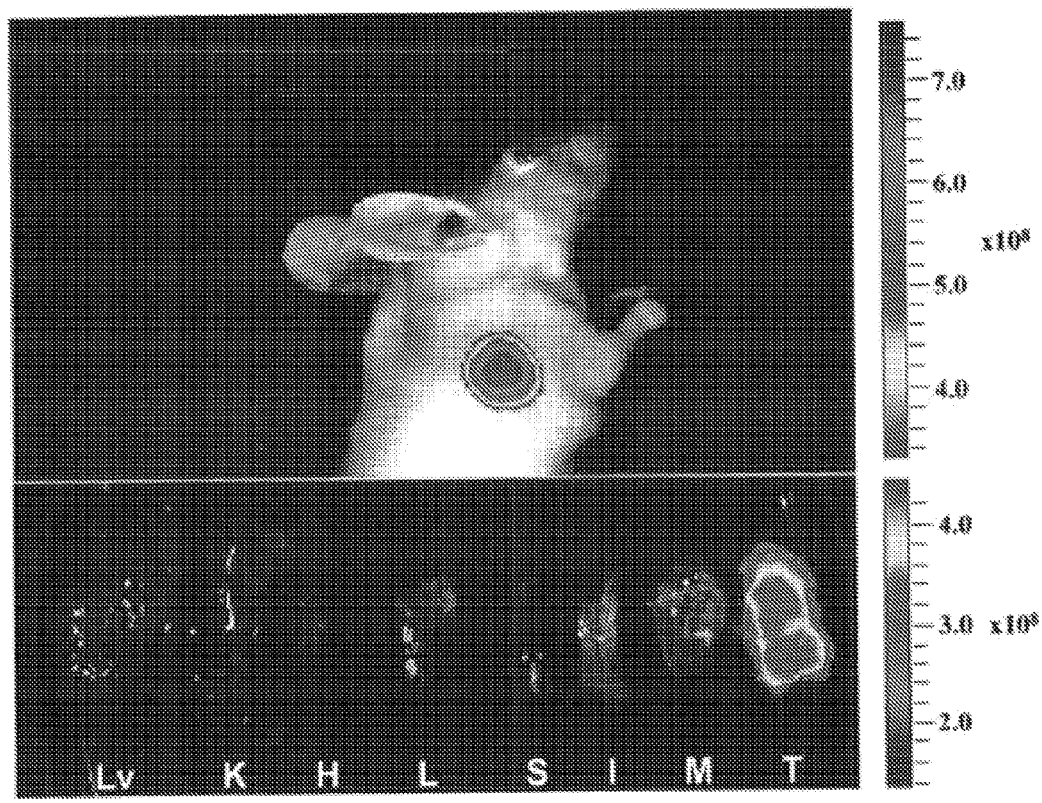
FIG. 26. Fluorescent-Folate (FA)-pRNA nanoparticle targets folate-receptor (FR) positive tumors xenograft upon systemic administration. Nude mice bearing the FR+ xenograft were injected with FA-AlexaFluor647-pRNA nanoparticles, which contained the core of the trifurcate domain, through the tail vein. Whole body imaging (Upper panel) was carried out using IVIA-Lumina system followed by dissection and organ imaging (lower panel, Lv=liver; K=kidney; H=heart; L=lung; S=spleen; I=intestine; M=muscle; T=tumor). Intensity in fluorescence is represented by the scale bar.

To confirm that the RNA nanoparticles composed of multiple subunits were not dissociated into individual subunits in vivo, RNA nanoparticles were constructed with one subunit carrying the folate to serve as a ligand for binding to the cancer cells, and the other subunit carrying the fluorescent dye. The nanoparticles were systemically injected into mice through the tail vein (as described above and the next section). Imaging via whole body detection revealed that fluorescence was located specifically at the xenografted cancer expressing the folate-receptor and was not detected in other organs in the body (FIG. 26), indicating that the particles did not dissociate in vivo after systemic delivery.

Animal Trials: In Vivo Targeting of Tumor Xenograft by Systemic Injection of Fluorescent-Folate (FA)-pRNA Nanoparticle.

Figure 29:
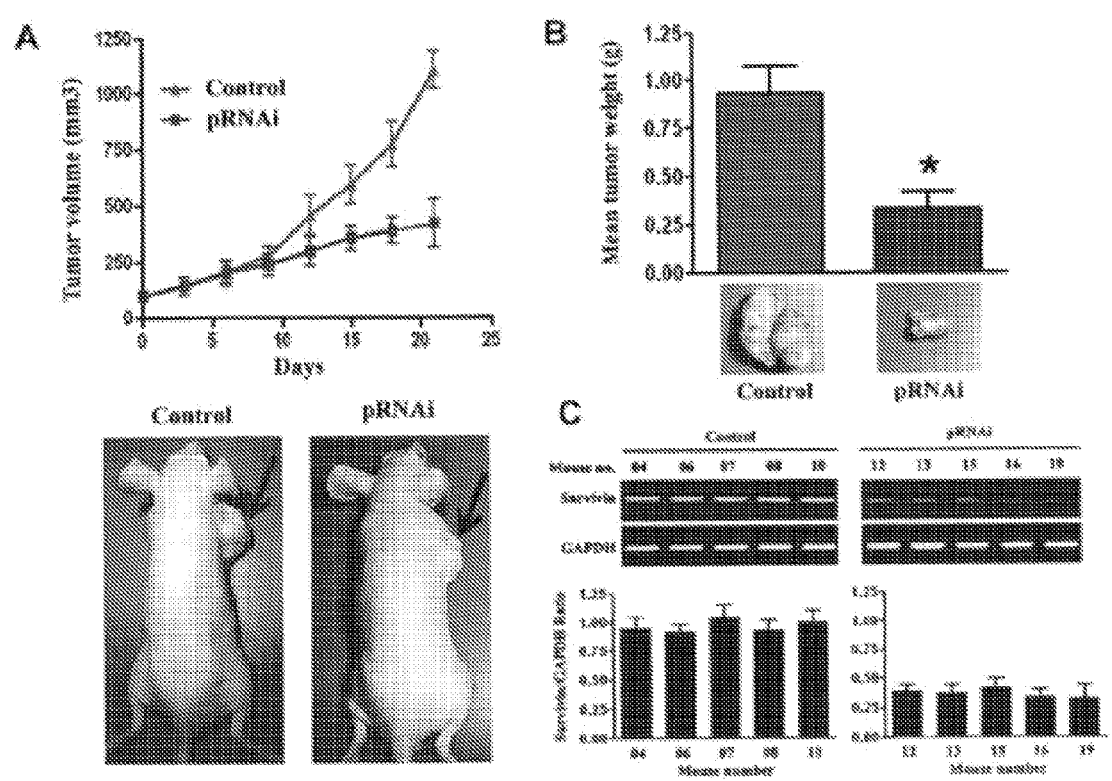
FIG. 29. (A) Tumor growth curves (n=5 mice per group) were plotted using mean tumor volume (top panel). Comparison of antitumor activity is shown in the bottom panel. Arrows indicate tumors. (B) Comparison of dissected tumors from control and pRNA/siRNA treatment groups. Each bar represents the mean tumor weight±S.D. of five animals per group. Significant difference from control group is represented by an asterisk (P<0.05). (C) The RT-PCR result indicated the specific targeting gene knock down effects of pRNAi treated tumor tissue compared to the control group.

Six-week-old male nude mice (nu/nu) were injected with cancer KB cells to produce cancer expressing the folate receptor. When the tumors grew up to about 500 mm³, the mice were injected intravenously through the tail vein with a single dose of folate-AlexaFluor647-labeled pRNA nanoparticle. Whole-body imaging was carried out 24 hours post-injection. It was found that the fluorescence was only located specifically at the xenografted cancer expressing the folate-receptor and was not detected in other organs such as the liver, spleen, heart, lung, intestine, kidney or skeleton muscle (FIG. 26), indicating that the trifurcate RNA junction domain can be used for constructing RNA nanoparticles for in vivo cancer targeted imaging and delivery. Local injection demonstrated that pRNA nanoparticles carrying both the folate ligand and the siRNA targeting the anti-apoptotic factor survivin inhibited the growth of cancer xenograft that is over-expressing the folate receptor (FIG. 29).

Additional Constructs.

Structures and functional characterization of additional RNA complexes assembled using the herein described trifurcate RNA junction domains are shown in FIGS. 31-35.

Example 3

Construction of a Variety of Therapeutic RNA Nanoparticles Using the X-Motif as Scaffold One of the advantages of RNA Nanotechnology is the feasibility to construct therapeutic particles carrying multiple therapeutics with defined structure and stoichiometry. However, controlled assembly of stable RNA nanoparticles with multiple functionalities to retain original role is challenging due to refolding after fusion. Herein, we report the construction of thermodynamically stable X-shaped RNA nanoparticles to carry four siRNA using reengineered RNA fragments derived from the central domain of the pRNA of bacteriophage phi29 DNA packaging motor. The tetravalent X-shaped nanoparticles self-assemble very efficiently in the absence of divalent salts, resistant to denaturation by 8 Molar urea, and remains intact at ultra-low concentrations. We proved that each arm of the four helixes in the X-motif can harbor one siRNA, ribozyme, or aptamer without affecting the folding of the central pRNA-X core, and each daughter RNA molecule within the nanoparticle fold into respective authentic structure and retain their biological and structural function independently. Gene silencing effects were progressively enhanced as the number of the siRNA in each pRNA-X nanoparticles gradually increased from one to two, three, and four. More importantly, systemic injection of ligand-containing nanoparticles into the tail-vein of mice revealed that the RNA nanoparticles remained intact and strongly bound to cancers without entering liver, lung or any other organs or tissues.

In this example we demonstrated that the central domain of bacteriophage phi29 motor pRNA can be engineered into stable X-motif to carry four functional modules in the absence of metal ions. The resulting nanoparticles were thermodynamically stable, resistant to dissociation under strongly denaturing conditions or at ultra-low concentrations. Incubation of four RNA oligos representing therapeutic functional motifs resulted in the self-assembly of tetravalent RNA nanoparticles as potential therapeutic agents. Progressive enhancement of gene silencing effects was observed when the number of siRNA in each pRNA-X nanoparticles increased from one to two, three and four. The results demonstrate that a wide range of therapeutic RNA molecules targeting cancer and viral infected cells can potentially be fused to the multivalent pRNA-X motif to achieve enhanced silencing effects.

Tetravalent RNA nanoparticles were constructed using the pRNA-X motif as a scaffold by incorporating four functional modules, MG (Malachite Green dye, triphenylmethane) aptamer, Luciferase siRNA (siLuci), Survivin siRNA (si-Surv) and Folate (FA) (FIG. 43A), denoted [pRNA-X/MG/FA/siLuci/siSurv] or corresponding scramble siRNA control. The presence of the functional moieties did not interfere with the formation of the pRNA-X core and the tetravalent complex assembles with high affinity (FIG. 43B). The purified constructs (Lane 9, FIG. 43B) were stable in absence of magnesium and remained intact under strongly denaturing conditions, even after the incorporation of functionalities. In the next sections we evaluated whether the incorporated RNA moieties retain their original folding and functionalities.

Assessment of MG fluorescence: MG binding aptamer was used as model system for structure and function verification. Free MG is not fluorescent by itself, but emits fluorescent light after binding to the aptamer. Fused MG-binding aptamer retained its capacity to bind MG, as revealed by its fluorescence emission (FIG. 43C). The fluorescence is comparable to optimized positive controls and therefore confirms that the MG aptamer assembled from two strands of the pRNA-X after incorporation into the RNA nanoparticles.

Targeted gene silencing assay in cancer cell model: Two pRNA-X nanoparticles were constructed for assaying the gene silencing effects harboring: (1) Folate and Survivin siRNA [pRNA-X/MG/FA/siLuci/si/Surv]; (2) FA and Survivin siRNA scramble control [pRNA-X/MG/FA/siLuci/si-Surv Scram]. After 48 hrs transfection, both reverse transcription-PCR (RT-PCR) assayed on mRNA level and western blot assayed on protein expression confirmed reduced survivin gene expression level of [pRNA-X/MG/FA/siLuci/si/Surv] nanoparticles compared to the scramble control (FIG. 43D).

Targeted gene silencing of Luciferase: Dual-Luciferase reporter system was used to quantitatively measure the gene silencing effects of the pRNA-X constructs harboring siRNA functionality targeting firefly luciferase gene (FIG. 43A). The relative luciferase activity was used to reflect the expression level of firefly luciferase gene by normalizing the firefly luciferase activity with the internal control, renilla luciferase activity. The results indicated that [pRNA-X/MG/FA/siLuci/si/Surv]nanoparticles displayed ~70% decrease in firefly luciferase gene expression (FIG. 43E).

Cell binding and entry of 4WJ-pRNA nanoparticles: Folate was incorporated in the pRNA-X nanoparticles to serve as cancer cell delivery agent via folate receptor-mediated endocytosis. Fluorescent pRNA-X nanoparticles with folate conjugated into one of the branches of the pRNA-X complex were tested for its cell binding efficiency. pRNA-X harboring FA and Cy3 labels [Cy3-pRNA-X/MG/FA/siLuci/si/Surv] served as the test sample, while the negative control harbored $NH_2$ and Cy3 label [Cy3-pRNA-X/MG/$NH_2$/siLuci/si/Surv]. Flow cytometry data revealed that the folate labeled pRNA-X nanoparticles bound and loaded its siRNA to the cell with ~85% binding efficiency (FIG. 5A). Confocal imaging indicated a strong binding of the RNA nanoparticles and efficient entry into the targeted cells, as demonstrated by the excellent co-localization and overlap of the fluorescent pRNA-X nanoparticles (red) and cytoplasma (green) (FIG. 44B).

Gene Silencing Effects were Progressively Enhanced as the Number of siRNA in Each pRNA-X Nanoparticles Increased Gradually from One, Two Three to Four.

Tetravalent pRNA-X complexes were constructed harboring multiple luciferase siRNAs to assay for enhanced gene silencing effects. Dual-Luciferase reporter system was used to quantitatively measure the gene silencing effects. For all the constructs, the total concentration of RNA was kept constant at 1.25 nM. The target sites on the luciferase gene for the four siRNAs (FIG. 45A) was located at 153-173, 196-216, 498-518, and 846-869 positions, as published in the literature. The incorporation of four identical siRNA sequences compromised the assembly of the X-motif due to self-folding of the complementary sequences of the respective siRNAs. To facilitate the assembly, the siRNA sequences were reversed (denoted with a prime, such as siLuci-1') at alternate helical branch locations. The reversed sequences have no impact on the functionality of the siRNA.

Silencing effects with increasing number of different Luciferase siRNA: As the number of different luciferase siR- NAs were gradually increased in the pRNA-X motif, progressive increase in silencing effects were observed as follows, ~25% (for 1 siRNA), 57% (for 2 siRNA), 72% (for 3 siRNA), and 81% (for 4 siRNA) (FIG. 45B).

Silencing effects of four identical luciferase siRNAs: Significant silencing effects were observed in presence of four identical siRNAs fused to the pRNA-X motif, compared to a single siRNA as follows, ~74% (for four siLuciferase-1), ~90% (for four siLuciferase-2), ~80% (for four siLuciferase-3), and ~72% (for four siLuciferase-4) (FIG. 45C). For comparison, we constructed the X-motif harboring a single siRNA (either siLuciferase-1 or 2 or 3 or 4) at helical locations H1 or H2 or H3 or H4, respectively (FIG. 37A-D). The silencing effects of the four different siRNAs increased following the trend, siLuciferase-2>siLuciferase-1≈siLuciferase-4>siLuciferase-3. The functionality of the siRNA was comparable at each of the arm of the X-motif. The data demonstrated that greatly enhanced effects were observed in presence of four identical siRNAs compared to a single siRNA (FIG. 46A-D).

Figure 47:
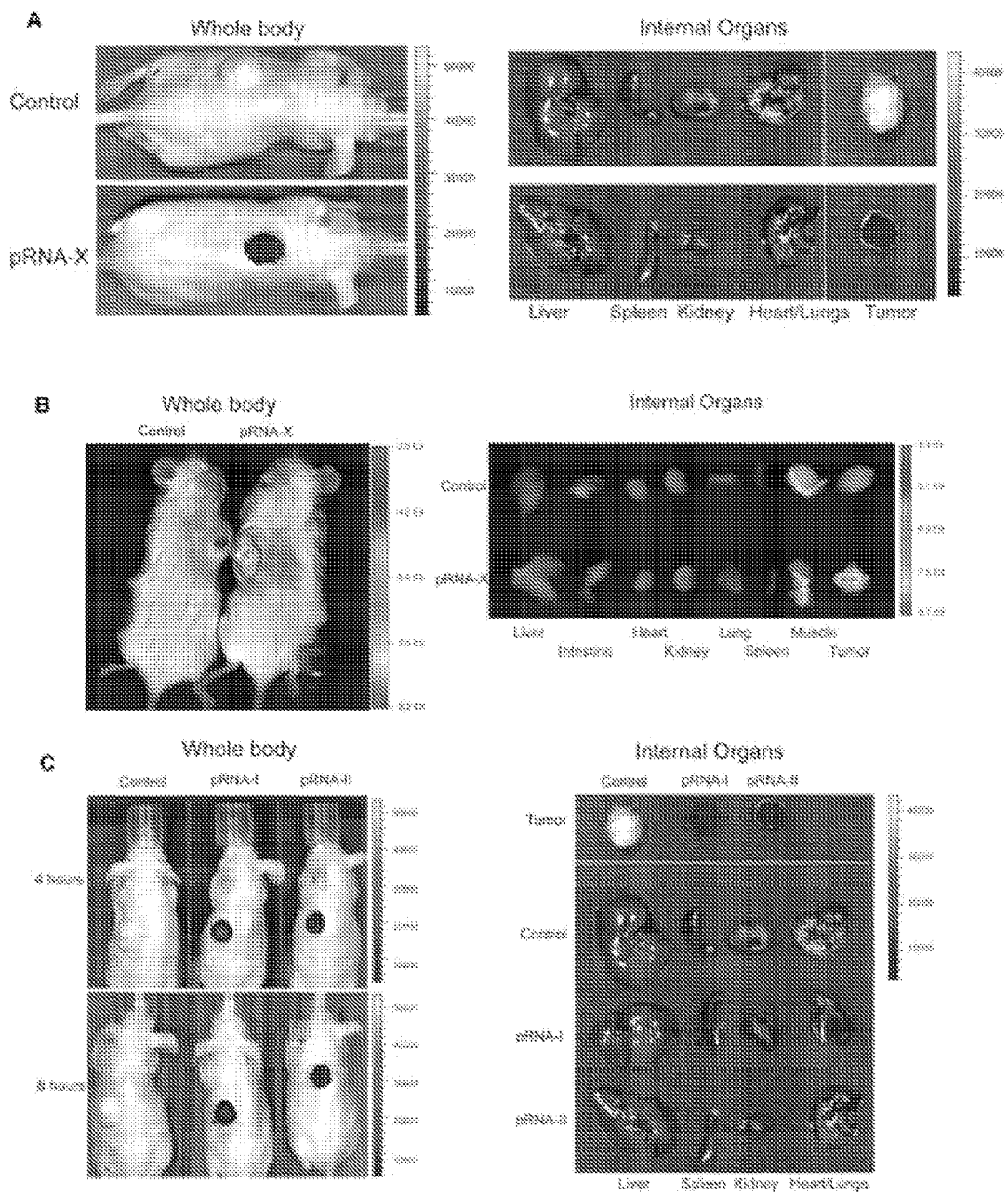
FIG. 47. In vivo binding and targeting of pRNA-X nanoparticles. The pRNA-X (harboring Folate and Alexa-647) nanoparticles target folate-receptor positive tumor xenografts upon systemic administration in nude mice, as revealed by whole body imaging (left), and internal organ imaging (right) of the control and pRNA-X treated mice. Scale bar: Fluorescent Intensity.
Figure 49:
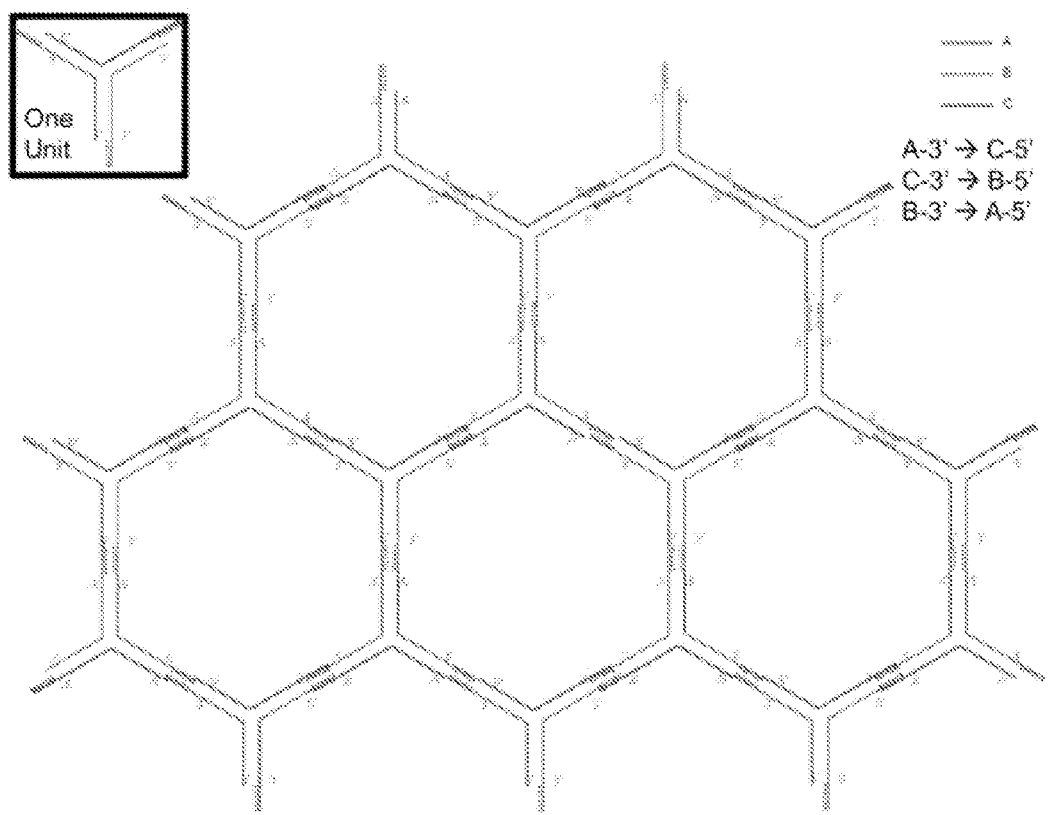
FIG. 49. Promoting the formation of 1D sheet by alternating the direction of the linking arm.

In Vivo Targeting of RNA Nanoparticles to Cancer Xenograft by Systemic Injection To confirm the chemically and thermodynamically stability of the X-shape RNA nanoparticles for specific cancer targeting in vivo, RNA nanoparticles were constructed with one of the four RNA fragments carrying the folate to serve as a ligand for binding to the cancer cells, and another RNA fragment carrying the fluorescent dye Alexa-647. The nanoparticles were systemically injected (ie, tail vein injections) into athymic nude mice bearing KB cells (folate receptor positive) xenografts in the subcutaneous flanks. Whole body imaging revealed that fluorescence was located specifically in the tumor xenografts (FIG. 47). Interestingly, the fluorescent nanoparticles were not detected in other organs in the body, indicating that the particles are not trapped in the liver, lungs, kidneys or other tissues or organs after systemic injection. The results were confirmed reproducibly by three independent labs with five trials. Together, these findings suggest a very selective targeting of the pRNA nanoparticles to tumors and not to normal tissues which would make this delivery system highly efficacious for future clinical applications.

Example 4

Toolkits for Fabrication of Versatile RNA Nanoparticles

In this example we expand the report of the development of an array of toolkit with the capability to fulfill the variable principles to construct architectures with diverse shapes and angles. RNA loops, cores, motifs and palindromes derived from the pRNA of bacteriophage phi29 DNA packaging motor were gathered in a toolkit to demonstrate their talent in utility for fabrication of RNA dimers, trimers tetramers, pentamers, hexamers, heptamers, octamer and branched diversity architectures via hand-in-hand, foot-to-foot and arm-on-arm interactions. These novel RNA nanostructures harbor drugs, ligands, siRNAs, fluorescent markers, ribozymes, RNA aptamers or miRNA for detection, purification, trafficking, delivery, and therapy. Incorporation of all functionality was achieved prior but not subsequent to the assembly of the RNA nanoparticles, thus ensure the production of homogeneous therapeutic nanoparticles. The nanoparticle formed herein with described tool kit demonstrates unexpected stability and carrying various biological functionalities. The versatility demonstrated by one biological RNA molecules implies an unparalleled potential concealed within the RNA nanotechnology field.

Figure 38:
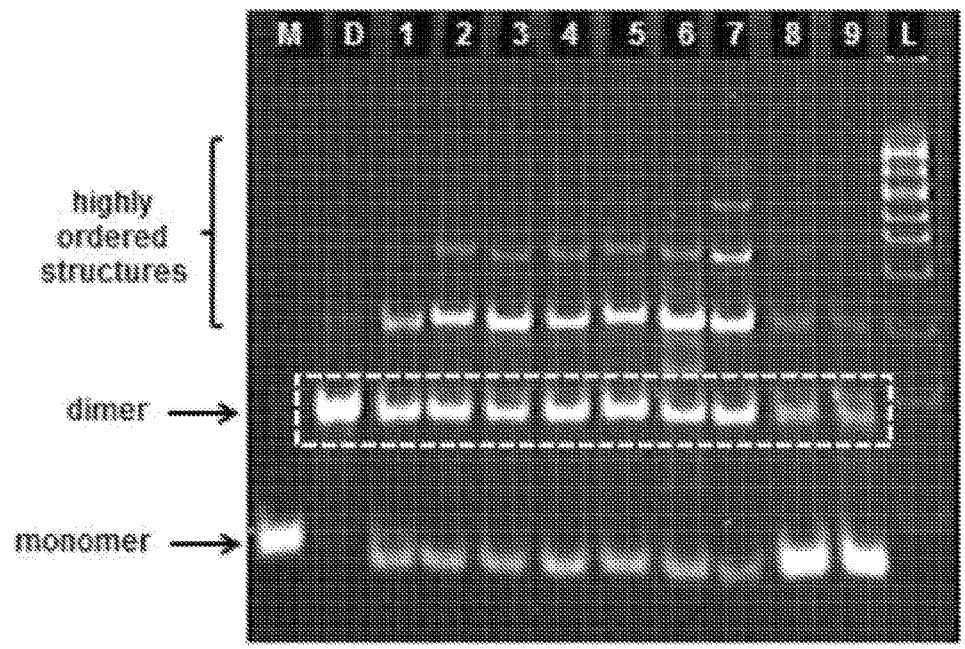
FIG. 38. Assay homo-dimer formations of loop extended pRNAs by native PAGE. (A) The wild type pRNA loop sequences were replaced by 9 pairs of extended loops and the folding of the new pRNAs were tested by Mfold. (B) Dimer formations of 7Aa', 7Bb', 7Cc', 7Dd', 7Ee', 7Ff', and 7Gg' (lane 1-7) by 6% TBM Native PAGE. Highly ordered structure was formed as slower migration bands shown in the gel. M: monomer, D: dimer; L: DNA ladders.

Toolkit I: Design of Loop Extend pRNA for Assembly of Higher Ordered pRNA Nanoparticles Based on Hand-in-Hand Interaction The loop extended pRNAs were constructed by replacing the 4-nt loop complementary region in R- and L-loop with 7-nt sequences which were from designed sequences pool or adapted from reference. Considering that altering nucleic acid sequences might affect the global folding of RNA molecules, the pRNA sequences with re-engineered loop sequences was folded by online RNA folding program Mfold (http://mfold.rna.albany.edu/?q=mfold/RNA-Folding-Form). There are total 9 pairs of loop sequences were selected out from the 7 nt loop sequence pool with predicted correct folding (FIG. 38A). Then these loop extended pRNAs were synthesized by in vitro transcription for future test.

Computation of loop-extended pRNA folding showed that 9 pairs of loop-loop interaction are potentially available for assembly of pRNA nanoparticles. To confirm the correct folding of the re-engineered pRNAs, 9 pRNA homo-dimers were synthesized to assay the loop-loop interactions. pRNA homo-dimer is an excellent system to assay the loop-loop interaction since the paired loop sequences are assigned to the R-loop and L-loop within the same pRNA. The correct folded pRNA will form a self-dimer by its complementary R-/L-loop in the presence of Mg2+, which migrates to higher position compared to monomer in native PAGE. After transcription, the 9 homo-dimers were refold in TMS at 37° C. for 1 hr and load into 6% native PAGE to assay the dimer formation. The results showed that 7 pairs of loop-loop sequences were able to facilitate homo-dimer formation (FIG. 38B) and 2 pairs of loop-loop sequences showed weak dimer formation indicating the misfolding of the pRNA structure after loop sequence changing. The dimer formation confirmed 7 pairs of loop-loop sequences are potential candidates for build up pRNA nano-scale assemblies.

Figure 39:
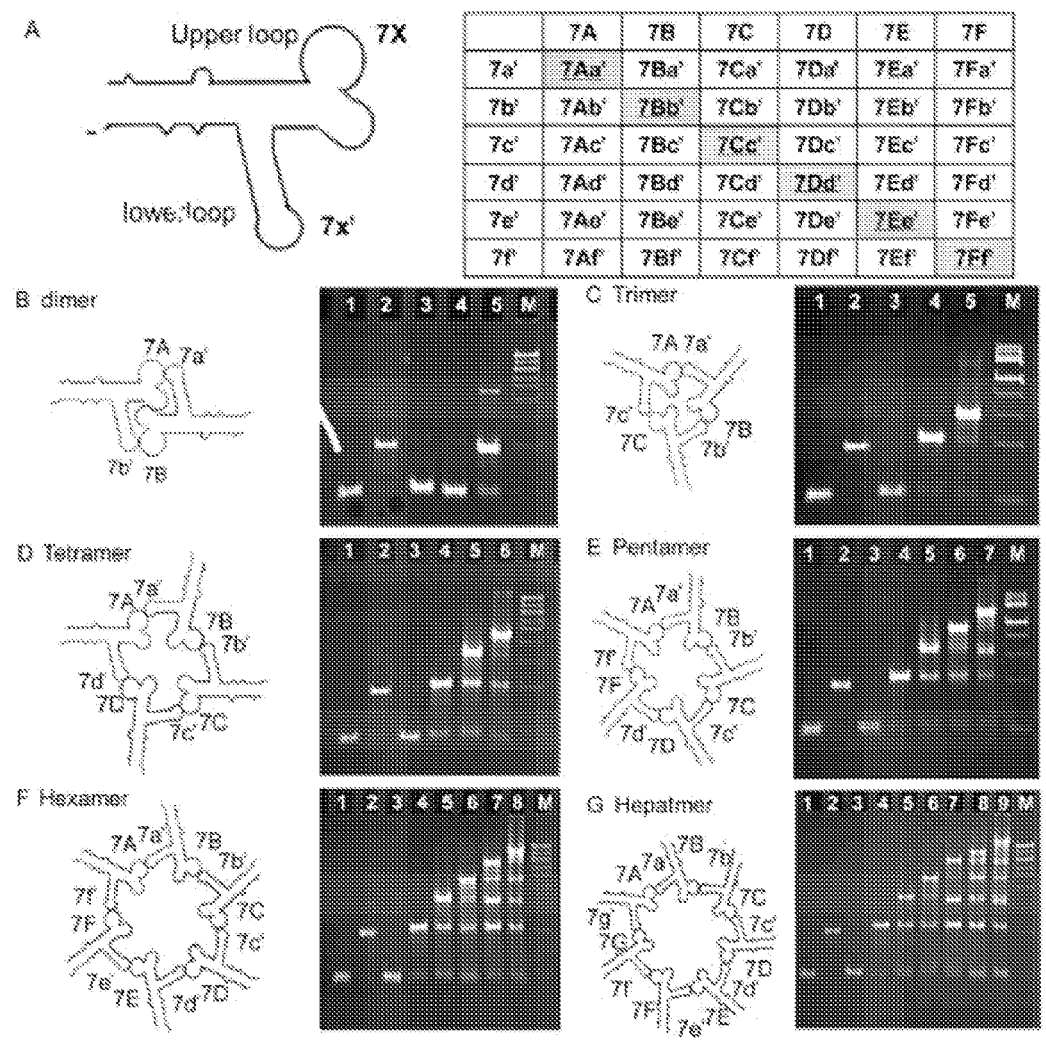
FIG. 39. Stepwise assembly of loop extended pRNA polyvalent nanoparticles. (A) Chart of loop extended pRNA hetero-monomers as the building block for assembly of pRNA polyvalent nanoparticles, 6% native PAGE showed the formation of (B) dimer; (C) trimer; (D) tetramer; (E) pentamer; (F) hexamer; and (G) heptamer.

Via reengineered loop-loop interaction, pRNA dimer (7Ab'-7Ba'), trimer (7Ba'-7Cb'-7Ac'), tetramer (7Ba'-7Cb'-7Dc'-7Ad'), pentamer (7Ba'-7Cb'-7Dc'-7Fd'-7Af'), hexamer (7Ba'-7Cb'-7Dc'-7Ed'-7Fe'-7Af'), and heptamer (7Ba'-7Cb'-7Dc'-7Ed'-7Fe'-7Gf'-7Ag') were assembled in the presence of Mg2+ as shown in the native PAGE (FIG. 41, FIG. 39). The formation of each nanoparticle was confirmed by AFM (FIG. 8 A-E). The sequences of loop extended pRNA homo-dimers and hetero-monomers are illustrated in Table 1.

Toolkit II: Design and Assembly of Higher Ordered pRNA Nanoparticles Based on 3'-End Palindrome Sequences.

Figure 5:
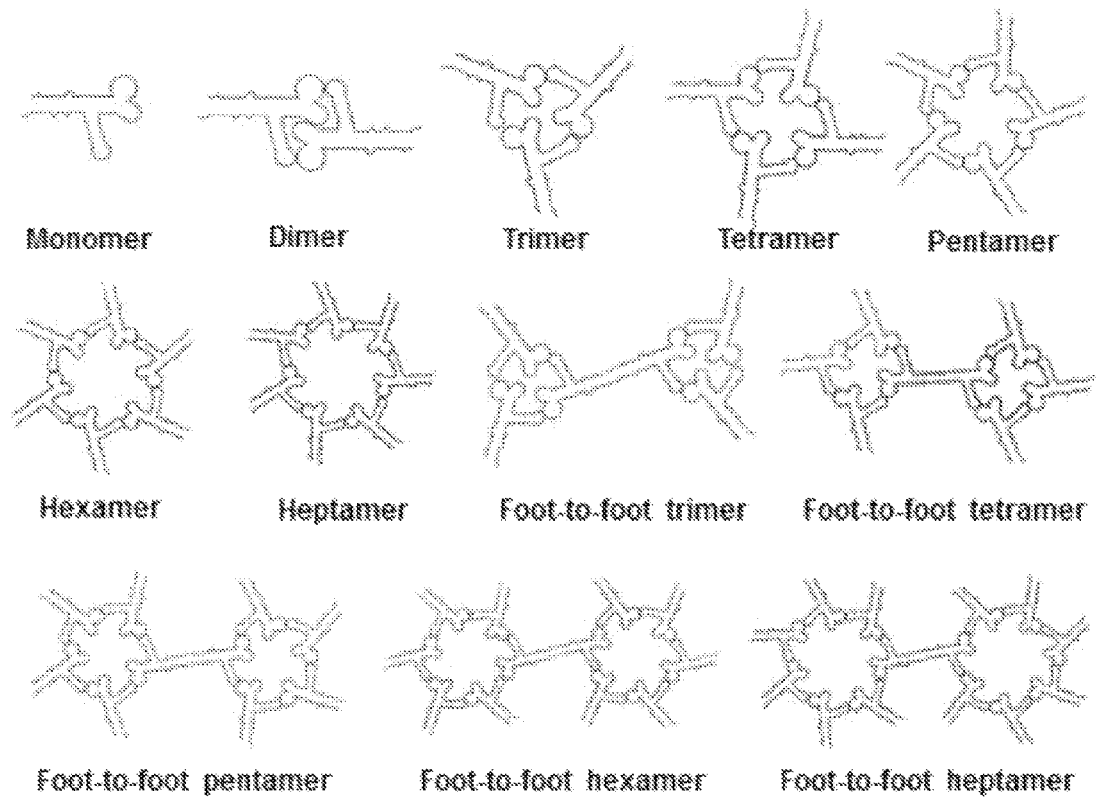
FIG. 5. The assembly of pRNA nanoparticles based on foot-to-foot palindromic annealing. 1: loop extended pRNA monomer; 2: loop extended pRNA dimer; 3: loop extended pRNA trimer; 4: loop extended pRNA tetramer, 5: loop extended pRNA pentamer; 6: loop extended pRNA hexamer; 7: loop extended pRNA heptamer; 8: foot-to-foot trimer; 9: foot-to-foot tetramer; 10: foot-to-foot pentamer: 11: foot-to-foot hexamer; 12: foot-to-foot heptamer.

A palindromic sequence is a nucleic acid sequence which has the same sequence whether read 5' to 3' on one strand or 5' to 3' on the complementary strand. The 6-nt palindrome sequence can be designed following the chart in FIG. 4, By introducing 3'-end extension with palindrome sequences on one subunit during the pRNA polyvalent nanoparticles formation process, the subunit harboring palindrome formed a foot-to-foot self-dimer and pRNA trimer, tetramer, pentamer, hexamer, and heptamer can further assembled into foot-to-foot structures as shown in native PAGE (FIG. 5). The formation of foot-to-foot nanostructures were further confirmed by the AFM imaging (FIG. 8)

Tool Kit III: Design of Branched pRNA Nanoparticles Based on 3WJ Motif

Larger macromolecular assemblies of RNA nanoparticles were constructed via intra-molecular assembly by utilizing junction motifs. The pRNA-3WJ core was assembled with high efficiency from three pieces of RNA oligos mixed in stoichiometric ratio in absence of any metal ions, as shown in native PAGE (FIG. 6). The length of the helices H3-1, H3-2, and H3-3 are 8 bp, 9 bp and 8 bp respectively, which keeps the construct stable under strongly denaturing conditions.

The pRNA-X motif was constructed by opening the right-hand loop of pRNA to insert 9 base pairs, thereby forming a double helical segment (H4-2), and extending the H4-3 helix by 4 base pairs (FIG. 6B). The length of the helices H4-1, H4-3 and H4-4 were 8 base pairs, respectively, while H4-2 was 9 base pairs long. The X-shaped motif can then be assembled from four RNA fragments mixed in stoichiometric ratio with high affinity in absence of metal salts, as shown in native PAGE (FIG. 6).

Self-complementary palindrome sequences can be added to either the 5'- or 3' end of one of the strands of the core motifs to bridge two 3WJ or X-motifs harboring multiple functionalities via intermolecular interactions to generate a tetramer or hexamer, respectively (FIG. 6C).

Branched hexavalent RNA nanoparticles can be constructed by utilizing two 3WJ cores. The main requirement is to match the thermodynamic properties of the cores to minimize misfolding. One such approach is the use of pRNA-3WJ core (forward sequence and reverse sequences) to generate two core scaffolds. Each of the three monomer 3WJ subunit harbors an overhanging reverse 3WJ fragment which serves as sticky end to bring together the three monomer constructs (FIG. 6D). The hexamer can be assembled in one step from five RNA fragments in the following ratios, $(a_{3WJ-FWD}+a_{3WJ-REV}):(a_{3WJ-FWD}+a_{3WJ-REV}):(a_{3WJ-FWD}+a_{3WJ-REV}):b_{3WJ}:c_{3WJ}=1:1:1:3:3$. Sequence of branched pRNA nanostructure is detailed in Table 2.

Each of the four aforementioned constructs can harbor functional modules at each of the branches, without affecting the folding of the core scaffolds. As an illustration, monomeric pRNA subunits were placed at each branch and AFM images strongly indicated the formation of homogenous RNA nanoparticles with desired structure and stoichiometry (FIG. 7).

Extension of the Multiple Way Junction Domains into Larger Structures with Branches.

Figure 16:
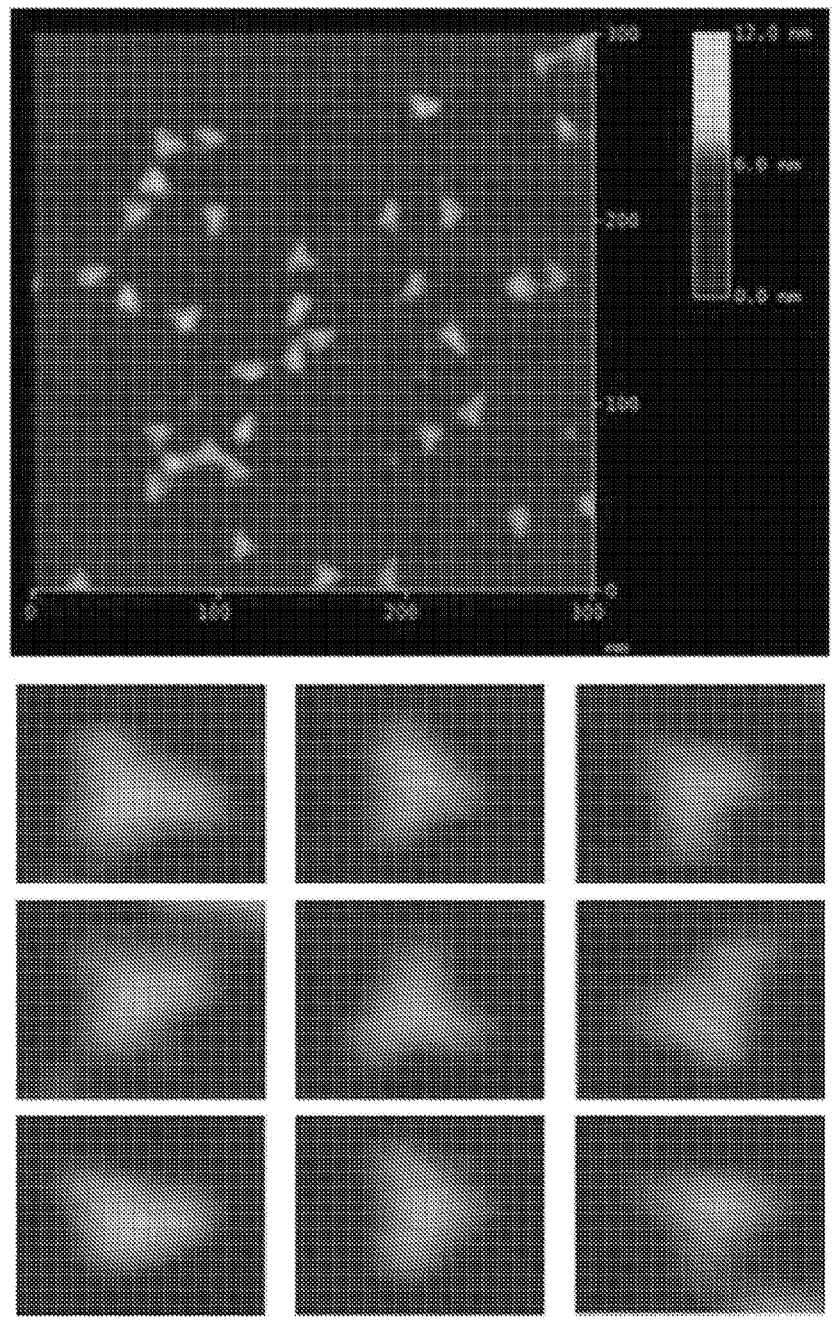
FIG. 16. AFM images of 3WJ-pRNA-siSur-Rz-FA nanoparticles.
Figure 17:
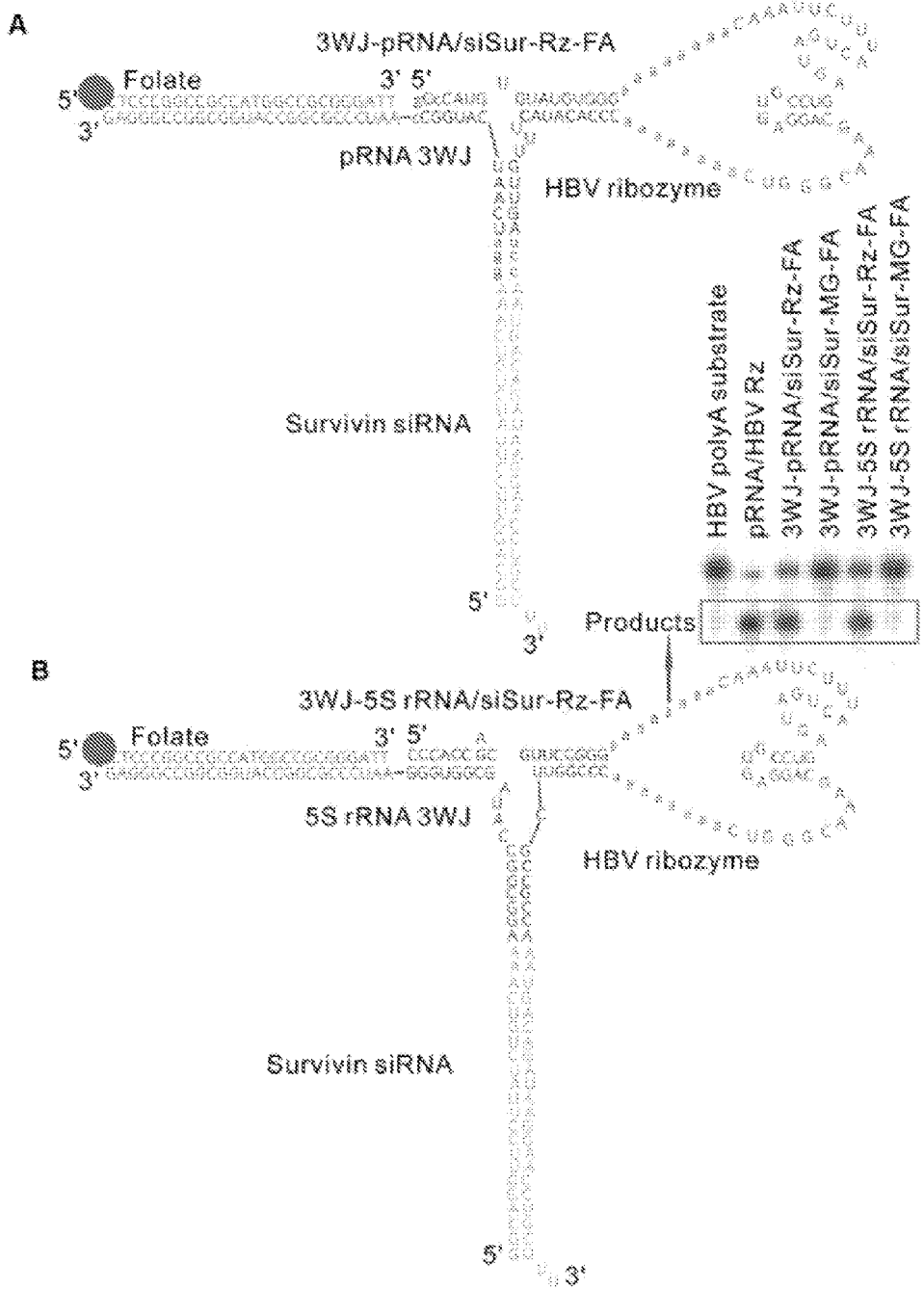
FIG. 17. Catalytic activity of the HBV ribozyme incorporated into the 3WJ-pRNA and 3WJ-5S rRNA cores. 3WJ-pRNA and 3WJ-5S rRNA cores, evaluated in 10% 8M urea PAGE. The cleaved RNA product is boxed. Positive control: pRNA/HBV-Rz; Negative control: 3WJ-RNA/SiSur-MG-FA FIG. 18. Functional assay of the MG aptamer Incorporated in RNA nanoparticles using the 3WJ-pRNA. MG fluorescence was measured using excitation wavelengths of 475 and 615 nm.
Figure 18:
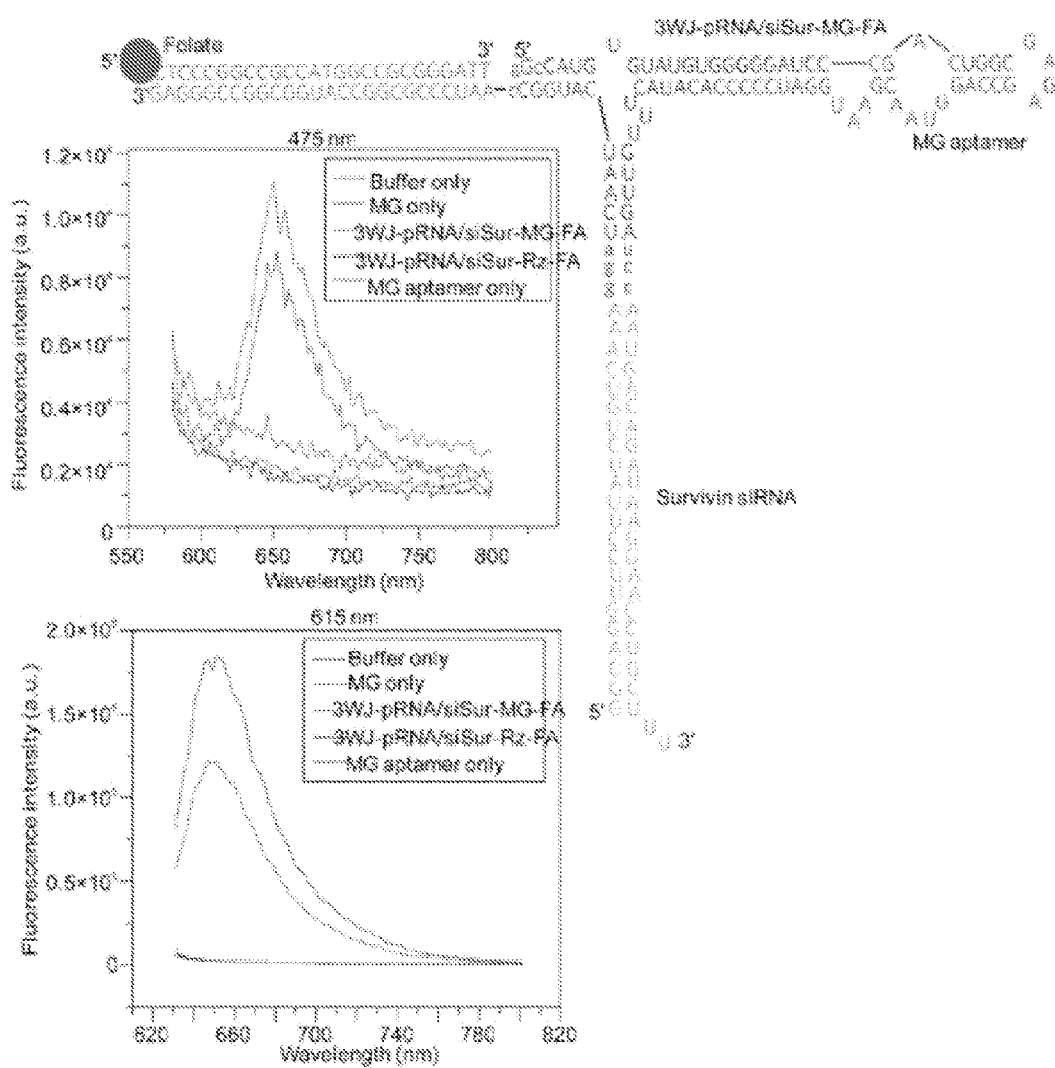
Figure 19:
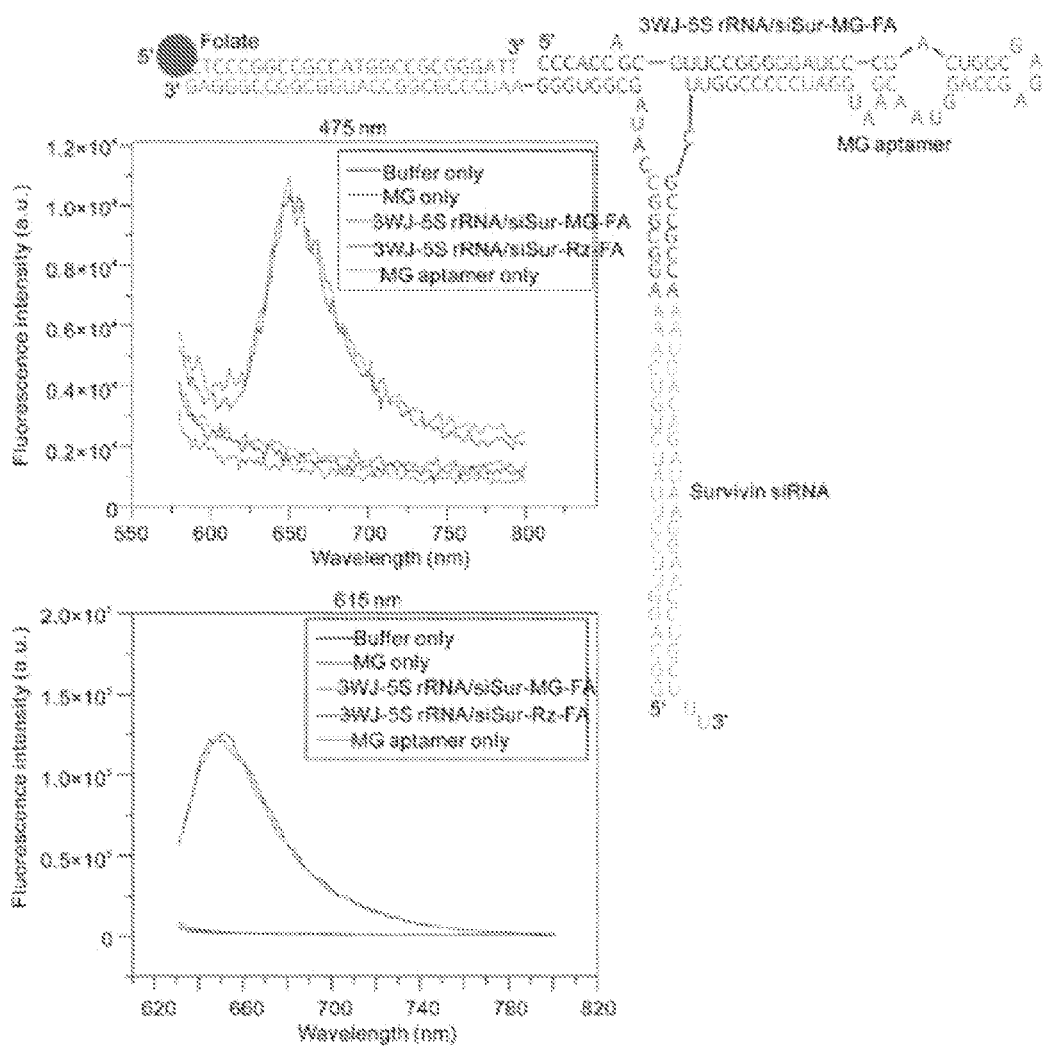
FIG. 19. Functional assay of the MG aptamer incorporated in RNA nanoparticles using the 3WJ-5S rRNA cores. MG fluorescence was measured using excitation wavelengths of 475 and 615 nm.
Figure 20:
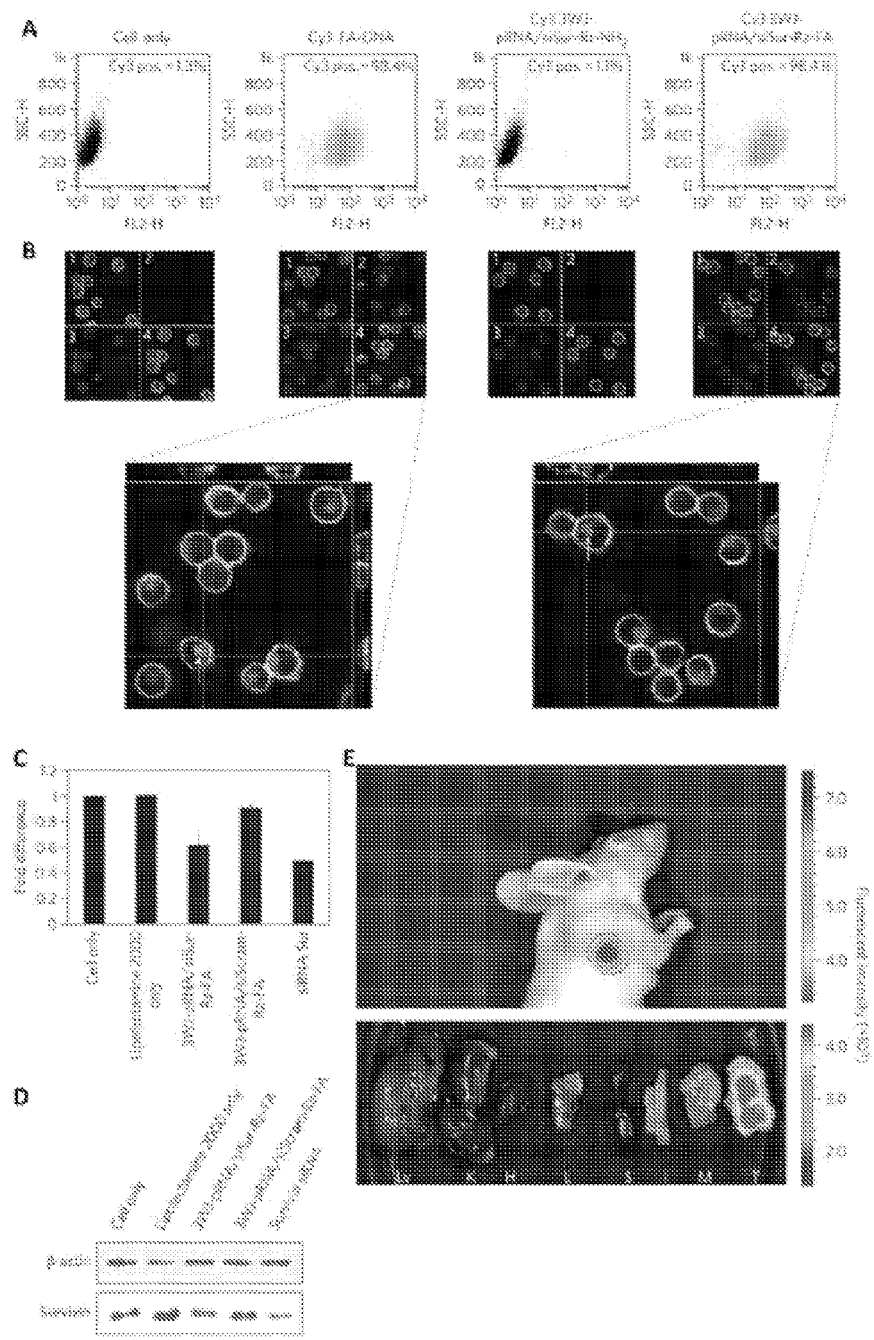
FIG. 20. In vitro and in vivo binding and entry of 3WJ-pRNA nanoparticles into targeted cells. (A) Flow cytometry revealed the binding and specific entry of fluorescent-[3WJ-pRNA-siSur-Rz-FA]nanoparticles into folate-receptor-positive (FA+) cells. Positive and negative controls were Cy3-FA-DNA and Cy3-[3WJ-pRNA-siSur-Rz-NH2](without FA), respectively. (B) Confocal images showed targeting of FA+- KB cells by co-localization (overlap, 4) of cytoplasm (green, 1) and RNA nanoparticles (red, 2) (magnified, bottom panel). Blue-nuclei, 3. (C), (D) Target gene knock-down effects shown by (C) qRT-PCR with GADPH as endogenous control and by (D) western blot assay with β-actin as endogenous control. (E) 3WJ-pRNA nanoparticles target FA+ tumour xenografts on systemic administration in nude mice. Upper panel: whole body; lower panel: organ imaging (Lv, liver; K, kidney; H, heart; L, lung; S, spleen; I, intestine; M, muscle; T, tumour).

The extension of the phi29 pRNA at the 3'-end does not affect the folding of pRNA global structure. The sequences of the three RNA oligos $a_{3WJ}$, $b_{3WJ}$, and $c_{3WJ}$, were placed at the 3'-end of the pRNA monomer, Ab'. Mixing of the three resulting pRNA chimeras containing $a_{3WJ}$, $b_{3WJ}$, and $c_{3WJ}$ sequences respectively, at equimolar concentrations led to the assembly of three-way branched nanoparticles harboring one pRNA at each branch (denoted as, tfd-3pRNA). AFM images strongly confirmed the formation of larger RNA complexes with three-branches (FIG. 16), which were consistent with gel shift assays. The 3WJ-3pRNA nanoparticles could also be co-transcribed and assembled in one step during transcription with high yield (FIG. 27). Similar concept is used for constructing multiple way branched nanoparticles harboring one pRNA at each branch (FIG. 8 AFM images for different kinds of pRNA nanoparticles).

Example 5

Using 3WJ and 4WJ Motifs to Develop Next Generation Bispecific, Trispecific and Tetraspecific RNA Aptamer Platform In this example, three-way junction (3WJ) and four-way junction (4WJ) X-motifs are used for the development of next-generation bispecific, trispecific and tetraspecific RNA aptamer platform. The aptamers are selected via modified nanotechnology-based SELEX approaches. After the selection, the optimized aptamers are fused onto the 3WJ and 4WJ scaffolds. The resulted bispecific and tetraspecific RNA aptamer is used for in-vivo delivery of diagnosis or therapeutic molecules. Because of the advantages the selected RNA aptamer provides over traditional antibody fragments (see below), and the broad origin of the resultant multivalent RNA nanoparticles (can be both naturally occurring biologic RNAs and synthetic RNAs) generated from this approach, the herein described multivalent RNA aptamer platform has unlimited potential in clinical diagnosis, research and therapeutics.

FIG. 50-52 describes the process of using 3wj and 4wj motifs to develop bispecific and tetraspecific RNA aptamer platform. Briefly, FIG. 50 shows the screening for RNA aptamers from different libraries that target cancer cell receptor, e.g. EPCAM. (A) 3WJ RNA with undefined number of random nucleotides at one branch of the loop of 3wj nanoparticle was used as library pool for the screening of RNA nanoparticles to bind cell receptors. (B) Undefined number of random sequence at the two loops of the 3WJ nanoparticle were used as library pool for the screening of RNA nanoparticles to bind cell receptors. (C) CEA aptamer was fused to 3WJ nanoparticle. In figures A-B, "N represents any number of any nucleotides. FIG. 51A shows an assay for binding affinity after 6th round RNA SELEX showing great enhancement comparing with 1st round RNA. FIGS. 51B and 51C shows preparation of FITC-EpCAM RNA aptamer library for cell binding test. FIG. 52A shows EpCAM binding and internalization of RNA nanoparticles containing the RNA aptamers from screening. (a) Cells were fixed and stained with the EpCAM antibody and visualized using the Alexa 488-conjugated secondary antibody as positive control. (b) EpCAM-pRNA nanoparticles (200 nM) labeled with Cy3 were incubated with HT29 cells for 24 h, fixed and imaged using confocal microscopy. Note the appearance of Cy3 signals in the cytoplasm of cells; the insert shows the enlarged image of a single cell. (Nuclei were labeled with DAPI.). FIG. 52B shows EpCAM binding and internalization. (a) EpCAM-pRNA (40 nM) labeled with Cy3 were incubated with HT29 cells for 4 h in serum-free media and imaged using confocal microscopy. Note the appearance of Cy3 signals representing RNA nanoparticles in the cytoplasm and nucleus of cells. (b) Enlarged image (5×) of a cells after EpCAM-pRNA treatment in serum free media. FIG. 52C shows binding and internalization of RNA particles containing 2'-F modified stable EpCAM RNA aptamer. FITC labeled 2'-F EpCAM-pRNA (40 nM) were incubated with HT29 cells for 4 h in serum free media and imaged using confocal microscopy. 2'-F aptamer was screened from SELEX earlier round (a-b), and later round (c-e). FIG. 52D summarizes the schematic of Bispecific (a-b) and trispecific (c) 3WJ based aptamer platform. (a) using a single 3WJ scaffold (see Part IB). (b) Using two 3WJ scaffolds linked by a sequence; (c) Hexamer constructs using three 3WJ scaffolds linked by a 3WJ core. The aptamers will be selected via modified nanotechnology-based SELEX approaches. The polyvalent nature of the RNA scaffolds will bring multiple targets together. Specific examples include, but not limited to, linking a T-cell with a tumor cell, targeting two antigens on a single tumor cell; target cytokines for inflammatory diseases or angiogenic factors for solid tumors.

The RNA 3WJ and 4WJ constructs harboring the aptamers will have the following features and offers significant advantages over the traditional monoclonal antibody fragments:
  i. enhanced targeting capability with high specificity;
  ii. enhanced thermodynamic and chemical stability
  iii. longer plasma half-life using chemically modified RNA;

iv. reproducible manufacturing framework for generating homogenous RNA nanoparticles via self-assembly of modular building blocks;
v. entirely RNA-based constructs, which will avoid immune responses and non-specific side effects;
vi. allows conjugation of chemotherapeutics to one of the branches of 3WJ/4WJ for 'cocktail' therapy;
vii. capable of crossing the blood-brain barrier for the treatment of head and neck cancer as well as brain cancer and central nervous system diseases.
viii. variable shaped RNA nanoparticles for optimized interactions.
ix. nanoscale size, which will enable it to bind to cryptic epitopes, that are not accessible by antibody fragments; escapes rapid kidney filtration.
x. deeper tumor penetrating capability
xi. offers multi-affinity targeting platform due to the polyvalent nature of the RNA scaffolds; will boost the therapeutic effects by engaging two or more targets simultaneously. Specific examples include, but not limited to, linking a T-cell with a tumor cell, targeting two antigens on a single tumor cell; cytokines for inflammatory diseases; angiogenic factors for solid tumors, etc.

The bispecific and trispecific aptamer RNA platform will have the wide ranging impacts in many diseases, including, but not limited to cancer, immunology, respiratory, central nervous system, inflammatory, and infectious diseases.

The three-way junction (3WJ) motifs that will be used for the development of next-generation bispecific and trispecific RNA aptamer platform include:

Family A: rRNA (16S H20-21-22; 16S H22-23-23a; 16S H25-25-26a; 16S H34-35-38; 23S H3-4-23; 23S H5H6H7; 23S H48-X-60; 23S H49-59.1-X; 23S H75-76-79; 23S H99-100-101).

Family B: rRNA (16S H28-29-43; 16S H32-33-34; 16S H33-33a-33b; 23S H33-34-35; 23S H49-50-51; 23S H83-84-85).

Family C: rRNA (16S H4-5-15; 16S H30-31-32; 16S H35-36-37; 16S H38-39-40; 23S H2-3-24; 23S H18-19-20; 23S H32-33-35; 23S H90-91-92); L11 rRNA; 5S rRNA; Alu domain; S domain; HH; G-riboswitch; P4P6; Twort Intron; S-dom RNaseP B-typ Unclassified family: Packaging RNA from: phi29; B103; SF5; and MN/NF phages.

The four-way junction (4WJ) motifs that will be used for the development of next-generation bispecific and trispecific RNA aptamer platform include:

Family H: 1U9S_78 Ribonuclease P_A; 2A2E_70 Ribonuclease P_A; 1NBS_89 Ribonuclease P_B; 2A64_90 Ribonuclease P_B; 1M50_13 Hairpin ribozyme; 1S72_1827 23S rRNA; 2AW4_1771 23S rRNA 2J01_1771 23S rRNA.

Family cH: 1KH6_4 HCV IRES; 2AVY_141 16S rRNA; 2J00_141 16S rRNA; 1NKW_2621 23S rRNA; 1S72_2678 23S rRNA; 2AW4_2642 23S rRNA; 2J01_2642 23S rRNA; 3F2Q7 Riboswitch (FMN); 3F2Q_31 Riboswitch (FMN); 1NKW_1457 23S rRNA; 2AW4_1443 23S rRNA.

Family cL: 2AVY_568 16S rRNA; 2J00_568 16S rRNA; 1NKW_1282 23S rRNA; 1S72_1373 23S rRNA; 2AW4_1269 23S rRNA; 2J01_1269 23S rRNA; 1EFW_6 Transfer RNA; 1EHZ_6 Transfer RNA; 1N78_506 Transfer RNA; 1QRS_6 Transfer RNA; 1U08_6 Transfer RNA; 2GIS_7 Riboswitch (SAM I).

Family cK: 2AVY_114 16S rRNA; 2J00_114 16S rRNA; 1NKW_2263 23S rRNA; 1S72_2318 23S rRNA; 2AW4_2284 23S rRNA; 2J01_2284 23S rRNA; 1NKW_1360 23S rRNA; 1S72_1452 23S rRNA; 2AW4_1346 23S rRNA; 2J01_1347 23S rRNA; 2AVY_18 16S rRNA; 2J00_18 16S rRNA.

Family π: 1U9S_118 Ribonuclease P_A; 2A2E_110 Ribonuclease P_A.

Family cW: 1NKW_1682 23S rRNA; 1S72_1743 23S rRNA, 2AW4_1665 23S rRNA; 2J01_1665 23S rRNA.

Family ψ: 1S72_42 23S rRNA; 1NKW_1824 23S rRNA; 1S72_1888 23S rRNA; 2AW4_1832 23S rRNA; 2J01_1832 23S rRNA; 1NKW_244 23S rRNA; 2AW4_267 23S rRNA.

Family X: 1NKW_608 23S rRNA; 2AW4_600 23S rRNA; 2J01_600 23S rRNA.

Family cX: 2IHX_166 Sarcoma virus; 2AVY_942 16S rRNA; 2J00_940 16S rRNA.

CONCLUSIONS

The presently disclosed pRNA trifurcate RNA junction domain, and its derivatives, including but not limited to x-motif domain and multiple way junction domains, have been characterized structurally and functionally in a manner not yet available for 3-way junction (3WJ) structures of other systems. The trifurcate RNA junction domain and its derivatives described herein, and RNA nanoparticles produced therefrom, over unexpected advantages in stability, subunit-subunit affinity, independence from magnesium, versatility in the employment of a wide variety of "payloads" (e.g., siRNA, ribozyme, aptamer, folate, etc.) that can be attached to each junction domain-forming subunit without compromising the biological activities of such payloads or the ability of the subunits to assemble, ease of production and assembly, and other advantages.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A multivalent RNA junction scaffold, comprising: a multiple RNA oligomer-formed polymer complex, wherein said polymer complex is configured to promote an array of thermodynamically and stoichiometrically stable RNA nanoparticles, wherein said multivalent RNA junction scaffold comprises a branched junction domain, said branched junction domain comprises groups of RNA polynucleotide helical regions, each said helical region has defined number of RNA nucleotide base pairs that form Watson-Crick bonds, wherein said groups of RNA polynucleotide helical regions comprise at least one unpaired RNA nucleotide base that is situated between at least two helical regions, and 3 unpaired RNA nucleotides situated at a 3' end of at least one helical region.

2. The multivalent RNA junction scaffold according to claim 1, wherein said RNA oligomer further comprises sequences for at least one biologically active moiety.

3. The multivalent RNA junction scaffold according to claim 1, wherein said RNA oligomer-formed polymer complex further comprises RNA branches with selective RNA or DNA sticky ends or palindrome sequences therein.

4. The multivalent RNA junction scaffold according to claim 1, wherein said oligomer-formed polymer complex is a trimer, a tetramer, a pentamer, a hexamer, a heptamer, or an octamer.

5. The multivalent RNA nanoparticle according to claim 2, wherein said bioactive moiety is heterogeneous.

6. The multivalent RNA nanoparticle according to claim 2, wherein at least one of said bioactive moiety is selected from the followings:
- SEQ. ID. NO: 1: folate-DNA strand (5' folate-CTC CCG GCC GCC ATG GCC GCG GGA TT 3'),
- SEQ. ID. NO: 2: Survivin siRNA antisense strand (5' UGA CAG AUA AGG AAC CUG CUU 3'),
- SEQ. ID. NO: 3: scramble control of Survivin siRNA antisense strand (5' AUA GUG GGA CCA AUC AAG CUU 3'),
- SEQ. ID. NO: 4: MG binding aptamer –1 (5' GGA UCC CGA CUG GCG AGA GCC AGG UAA CGA AUG GAU CC 3'),
- SEQ. ID. NO: 5: MG binding aptamer –2 strand 1 (5' AUG GUA ACG AAU GA 3'),
- SEQ. ID. NO: 6: MG binding aptamer –2 strand 2 (5' CAA UCC GAC AU 3'),
- SEQ. ID. NO: 7: STV binding aptamer (5' CGA CCA GAA UCA UGC AAG UGC GUA AGA UAG UCG CGG GUC G 3'),
- SEQ. ID. NO: 8: working HBV ribozyme (5' CAA AUU CUU UAC UGA UGA GUC CGU GAG GAC GAA ACG GGU C 3'),
- SEQ. ID. NO: 9: disabled HBV ribozyme (5' CAA AUU CUU UAC UAA UGA GUC CGU GAG GAC GAA ACG GGU C 3'),
- SEQ. ID. NO: 10: firefly Luciferase siRNA 1 antisense strand (5' GUU GGC ACC AGC AGC GCA C 3'),
- SEQ. ID. NO: 11: firefly Luciferase siRNA 2 antisense strand (5' UCG AAG UAC UCA GCG UAA G 3'),
- SEQ. ID. NO: 12: firefly Luciferase siRNA 3 antisense strand (5' GCC CAU AUC GUU UCA UAG C 3'),
- SEQ. ID. NO: 13: firefly Luciferase siRNA 4 antisense strand (5' GUA GAU GAG AUG UGA CGA A 3'),
- SEQ. ID. NO: 14: scramble control of firefly Luciferase siRNA antisense strand (5'GUC GGU UUC GUG AAG GAG A 3').

7. The multivalent RNA junction scaffold according to claim 2, wherein said bioactive moiety is drugs, markers, fluorescent dyes, chemicals, siRNAs, ribozymes, riboswitches, aptamer or other functionalities.

8. The multivalent RNA junction scaffold according to claim 2, wherein said multifunctional bioactive moiety is therapeutics for treatment of cancers, viral infections, genetic diseases and other ailing.

9. The multivalent RNA junction scaffold according to claim 2, wherein said multifunctional bioactive moiety is for detection or diagnosis of cancers, viral infections, genetic diseases and other ailing.

10. The multivalent RNA junction scaffold according to claim 2, wherein at least one of said multifunctional bioactive moiety is used as an RNA antibody for detection or diagnosis of cancers, viral infections, genetic diseases and other ailing.

11. The multivalent RNA junction scaffold according to claim 1, wherein said multiple RNA junction scaffold is a trifurcate junction domain comprising:
a. an $a_{3WJ}$ RNA polynucleotide;
b. a $b_{3WJ}$ RNA polynucleotide; and
c. a $c_{3WJ}$ RNA polynucleotide.

12. The multivalent RNA junction scaffold according to claim 1, wherein said multiple RNA junction scaffold is a X-motif comprising:
d. an $a_{X-RNA}$ polynucleotide;
e. a $b_{X-RNA}$ polynucleotide;
f. a $c_{X-RNA}$ polynucleotide; and
g. a $d_{X-RNA}$ polynucleotide.

13. The multivalent RNA junction scaffold according to claim 11, wherein said trifurcate junction domain comprising at least:
an $a_{3WJ}$ RNA polynucleotide comprises the SEQ. ID. NO: 15 (5'-UUG CCA UGU GUA UGU GGG-3');
a $b_{3WJ}$ RNA polynucleotide comprises the SEQ. ID. NO: 16 (5'-CCC ACA UAC UUU GUU GAU CC-3');
a $c_{3WJ}$ RNA polynucleotide comprises the SEQ. ID. NO: 17 (5'-GGA UCA AUC AUG GCA A-3').

14. The multivalent RNA junction scaffold according to claim 12, wherein said X-motif comprising:
a. an $a_{X-RNA}$ polynucleotide comprises the SEQ. ID. NO:18 (5'-UUG CCA UGU GUA UGU GGG UUC CAG CAC-3')
b. a $b_{X-RNA}$ polynucleotide comprising the SEQ. ID. NO: 19 (5'-GUG CUG GAA CUG ACU GC-3')
c. a $c_{X-RNA}$ polynucleotide comprising the SEQ. ID. NO: 20 (5'-GCA GUC AGC CCA CAU ACU UUG UUG AUC C-3'); and
d. a $d_{X-RNA}$ polynucleotide comprising SEQ. ID. NO: 21 (5'-GGA UCA AUC AUG GCA A-3').

15. The multivalent RNA junction scaffold according to claim 13, wherein said trifurcate RNA junction domain comprising:
a. a first helical region RNA polynucleotide comprising 8 RNA nucleotide base pairs, said RNA polynucleotide forms canonical Watson-Crick bonds;
b. a second helical region RNA polynucleotide comprising (i) 9 RNA nucleotide base pairs, (ii) at least one unpaired RNA nucleotide base that is situated between the first helical region and the second helical region, and (iii) 3 unpaired RNA nucleotides situated at a 3' end of said second helical region RNA polynucleotide; and
c. a third helical region RNA polynucleotide comprising 8 RNA nucleotide base pairs which form canonical Watson-Crick bonds.

16. The multivalent RNA junction scaffold according to claim 13, wherein said trifurcate RNA junction domain comprising:
a. a first helical region RNA polynucleotide comprising 6 RNA nucleotide base pairs, said RNA polynucleotide forms canonical Watson-Crick bonds;
b. a second helical region RNA polynucleotide comprising (i) 9 RNA nucleotide base pairs, (ii) at least one unpaired RNA nucleotide base that is situated between the first helical region and the second helical region, and (iii) 3 unpaired RNA nucleotides situated at a 3' end of said second helical region RNA polynucleotide; and
c. a third helical region RNA polynucleotide comprising 6 RNA nucleotide base pairs which form canonical Watson-Crick bonds.

17. A multipartite RNA nanoparticle, comprising an array of thermodynamically and stoichiometrically stable, multifunctional bioactive moiety crystalline, wherein said crystalline is self-assembled by a multivalent RNA junction scaffold, wherein said multivalent RNA junction scaffold is a multiple RNA oligomer formed polymer complex, and comprises a branched junction domain, said branched junction domain comprises groups of RNA polynucleotide helical regions, each said helical region has defined number of RNA nucleotide base pairs that form Watson-Crick bonds, wherein said groups of RNA polynucleotide helical regions comprise at least one unpaired RNA nucleotide base that is situated between at least two helical regions, and 3 unpaired RNA nucleotides situated at a 3' end of at least one helical region.

18. The multipartite RNA nanoparticle according to claim 17, wherein said RNA crystalline structure is formed by bottom-up self-assembly.

19. The multipartite RNA nanoparticle according to claim 17, wherein said RNA junction scaffold core is a polygon formed by said multiple RNA oligomer.

20. The multipartite RNA nanoparticle according to claim 17, wherein said RNA crystalline structure is further arranged by alternating the orientation of at least one said RNA polynucleotide's neighboring molecule.

21. The multipartite RNA nanoparticle according to claim 17, wherein said RNA crystalline structure is further arranged to form 1D and 2D sheets by controlling said RNA polynucleotides' numbers in a given unit of said scaffold.

22. The multipartite RNA nanoparticle according to claim 17, wherein said RNA oligomer-formed polymer complex further comprises RNA branches with selective RNA or DNA sticky ends or palindrome sequences therein.

23. The multipartite RNA nanoparticle according to claim 17, wherein said RNA oligomers-formed polymer complex is a trimer, a tetramer, a pentamer, a hexamer, a heptamer or an octamer.

24. A method of making a multipartite RNA nanoparticle, comprising admixing in substantially equimolar amounts of RNA polynucleotides, wherein said RNA polynucleotides contain a collection of RNA junction domains to form a multivalent RNA junction scaffold comprising a branched junction domain, said branched junction domain comprises groups of RNA polynucleotide helical regions, each said helical region has defined number of RNA nucleotide base pairs that form Watson-Crick bonds, wherein said groups of RNA polynucleotide helical regions comprise at least one unpaired RNA nucleotide base that is situated between at least two taro helical regions, and 3 unpaired RNA nucleotides situated at a 3' end of at least one helical region, wherein said multipartite RNA nanoparticle promotes the assembly of an array of bioactive moiety into crystalline structure.

25. A method of delivering a biological active moiety to a cell, comprising contacting the cell with a multipartite RNA nanoparticle, wherein said multipartite RNA nanoparticle is assembled by an RNA junction scaffold comprising a branched junction domain, said branched junction domain comprises groups of RNA polynucleotide helical regions, each said helical region has defined number of RNA nucleotide base pairs that form Watson-Crick bonds, whey said groups of RNA polynucleotide helical regions comprise at least one unpaired RNA nucleotide base that is situated between at least two helical regions, and 3 unpaired RNA nucleotides situated at a 3' end of at least one helical region.

26. A method of delivering a therapeutic agent or a detectable labeling agent, or both, comprising administering to the subject a multipartite RNA nanoparticle, wherein said multipartite RNA nanoparticle is assembled by an RNA junction scaffold comprising a branched junction domain, said branched junction domain comprises groups of RNA polynucleotide helical regions, each said helical region has defined number of RNA nucleotide base pairs that form Watson-Crick bonds, wherein said groups of RNA polynucleotide helical regions comprise at least one unpaired RNA nucleotide base that is situated between at least two helical regions, and 3 unpaired RNA nucleotides situated at a 3' end of at least one helical region.

27. A method of using branched trifurcate or four way X-motif junction domain as a scaffold to produce stable multivalent RNA aptamers, wherein said stable multivalent RNA aptamers recognize at least one given substrate, comprising:
   a. attaching a collection of random sequences to pRNA trifurcate or four way X-motif junction domain;
   b. selecting said random sequences to identify those that having high binding affinity to said substrate; and
   c. conjugating said identified aptamer or an otherwise available aptamer to pRNA trifurcate or four way X-motif junction domain, wherein said available aptamer mimics at least one antibody to said at least one substrate.

28. The method according to claim 27, wherein said stable aptamer carries multivalent variants that recognize both cytotoxic T lymphocytes and different tumor cells.

29. The method according to claim 27, wherein said given substrate is an antigen, a protein, or a cell surface marker.

30. The method according to claim 27, wherein said identified aptamer provides advantages over traditional antibody fragments.

31. The trifurcate junction domain according to claim 11, wherein said domain is used for therapeutic delivery, diagnosis of diseases, promotion of RNA crystallization, or creation of stable RNA aptamer.

32. The trifurcate junction domain according to claim 11 is a trifurcate junction domain of DNA packaging RNA selected from the followings: phages PZA, phi15, BS32, B103, Nf, M2Y and GA-1, wherein said trifurcate junction domain is used for therapeutic delivery, diagnosis of diseases, promotion of RNA crystallization, or creation of stable RNA aptamer.

33. The trifurcate junction domain in claim 11 is selected from the followings: pRNA, 5s rRNA, HCV, Alu SRP, Hammerhead ribozyme, 16s H34-H35-H38, 23s H75-H76-H79, 23s H83-H84-H85, G-Riboswitch (Type I), TPP Riboswitch (Type II), and M-box Riboswitch (Type II), wherein said trifurcate junction domain is used for therapeutic delivery, diagnosis of diseases, promotion of RNA crystallization, or creation of stable RNA aptamer.

34. The trifurcate junction domain in claim 11 is selected from the followings:
   Family A: rRNA (16S H20-21-22; 16S H22-23-23a; 16S H25-25-26a; 16S H34-35-38; 23S H3-4-23; 23S H5H6H7; 23S H48-X-60; 23S H49-59.1-X; 23S H75-76-79; 23S H99-100-101),
   Family B: rRNA (16S H28-29-43; 16S H32-33-34; 16S H33-33a-33b; 23S H33-34-35; 23S H49-50-51; 23S H83-84-85),
   Family C: rRNA (16S H4-5-15; 16S H30-31-32; 16S H35-36-37; 16S H38-39-40; 23S H2-3-24; 23S H18-19-20; 23S H32-33-35; 23S H90-91-92); L11 rRNA; 5S rRNA; Alu domain; S domain; HH; G-riboswitch; P4P6; Twort Intron; S-dom RNaseP B-typ, or
   Unclassified family: Packaging RNA from: phi29; B103; SF5; and MN/NF phages.

35. The four way junction motif in claim 12 is selected from the followings:

Family H: 1U9S_78 Ribonuclease P_A; 2A2E_70 Ribonuclease P_A; 1NBS_89 Ribonuclease P_B; 2A64_90 Ribonuclease P_B; 1M50_13 Hairpin ribozyme; 1S72_1827 23S rRNA; 2AW4_1771 23S rRNA; 2J01_1771 23S rRNA, Family cH: 1KH6_4 HCV IRES; 2AVY_16S rRNA; 2J00_141 16S rRNA; 1NKW_2621 23S rRNA; 1S72_2678 23S rRNA; 2AW4_2642 23S rRNA; 2J01_2642 23S rRNA; 3F2Q_7 Riboswitch (FMN); 3F2Q_31 Riboswitch (FMN); 1NKW_1457 23S rRNA; 2AW4_1443 23S rRNA, Family cL: 2AVY_568 16S rRNA; 2J00_568 16S rRNA; 1NKW_1282 23S rRNA; 1S72_1373 23S rRNA; 2AW4_1269 23S rRNA; 2J01_1269 23S rRNA; 1EFW_6 Transfer RNA; 1EHZ_6 Transfer RNA; 1N78_506 Transfer RNA; 1QRS_6 Transfer RNA; 1U08_6 Transfer RNA; 2GIS_7 Riboswitch (SAM I), Family cK: 2AVY_114 16S rRNA; 2J00_114 16S rRNA; 1NKW_2263 23S rRNA; 1S72_2318 23S rRNA: 2AW4_2284 23S rRNA; 2J01_2284 23S rRNA; 1NKW_1360 23S rRNA; 1S72_1452 23S rRNA; 2AW4_1346 23S rRNA; 2J01_1347 23S rRNA; 2AVY_18 16S rRNA; 2J00_18 16S rRNA, Family π: 1U9S_118 Ribonuclease P_A; 2A2E_110 Ribonuclease P_A, Family cW: 1NKW_1682 23S rRNA; 1S72_1743 23S rRNA; 2AW4_1665 23S rRNA; 2J01_1665 23S rRNA, Family ψ: 1S72_42 23S rRNA; 1NKW_1824 23S rRNA; 1S72_1888 23S rRNA; 2AW4_1832 23S rRNA: 2J01_1832 23S rRNA: 1NKW_244 23S rRNA; 2AW4_267 23S rRNA, Family X: 1NKW_608 23S rRNA; 2AW4_600 23S rRNA; 2J01_600 23S rRNA, or Family cX: 2IHX_166 Sarcoma virus; 2AVY_942 16S rRNA; 2J00_940 16S rRNA.

* * * * *

SEQUENCE LISTING

<160> NUMBER OF SEQ ID NOS: 186

<210> SEQ ID NO 1

```
<211> LENGTH: 25
<212> TYPE: DNA
<213> ORGANISM: unknown
<220> FEATURE:
<223> OTHER INFORMATION: folate

<400> SEQUENCE: 1
ctcccggccg ccatggccgc gggat                                          25

<210> SEQ ID NO 2
<211> LENGTH: 21
<212> TYPE: RNA
<213> ORGANISM: artificial
<220> FEATURE:
<223> OTHER INFORMATION: siRNA antisense strand

<400> SEQUENCE: 2
ugacagauaa ggaaccugcu u                                              21

<210> SEQ ID NO 3
<211> LENGTH: 21
<212> TYPE: RNA
<213> ORGANISM: artificial
<220> FEATURE:
<223> OTHER INFORMATION: scramble siRNA antisense strand

<400> SEQUENCE: 3
auagugggac caaucaagcu u                                              21

<210> SEQ ID NO 4
<211> LENGTH: 38
<212> TYPE: RNA
<213> ORGANISM: artificial
<220> FEATURE:
<223> OTHER INFORMATION: MG binding aptamer -1

<400> SEQUENCE: 4
ggaucccgac uggcgagagc cagguaacga auggaucc                            38

<210> SEQ ID NO 5
<211> LENGTH: 14
<212> TYPE: RNA
<213> ORGANISM: artificial
<220> FEATURE:
<223> OTHER INFORMATION: MG binding aptamer -2 strand 1

<400> SEQUENCE: 5
augguaacga auga                                                      14

<210> SEQ ID NO 6
<211> LENGTH: 11
<212> TYPE: RNA
<213> ORGANISM: artificial
<220> FEATURE:
<223> OTHER INFORMATION: MG binding aptamer -2 strand 2

<400> SEQUENCE: 6
caauccgaca u                                                         11

<210> SEQ ID NO 7
<211> LENGTH: 40
<212> TYPE: RNA
<213> ORGANISM: artificial
<220> FEATURE:
<223> OTHER INFORMATION: STV binding aptamer

<400> SEQUENCE: 7
```
cgaccagaau caugcaagug cguaagauag ucgcggucg                    40

<210> SEQ ID NO 8
<211> LENGTH: 40
<212> TYPE: RNA
<213> ORGANISM: artificial
<220> FEATURE:
<223> OTHER INFORMATION: working HBV ribozyme

<400> SEQUENCE: 8
caaauucuuu acugaugagu ccgugaggac gaaacggguc                    40

<210> SEQ ID NO 9
<211> LENGTH: 40
<212> TYPE: RNA
<213> ORGANISM: artificial
<220> FEATURE:
<223> OTHER INFORMATION: disabled HBV ribozyme

<400> SEQUENCE: 9
caaauucuuu acuaaugagu ccgugaggac gaaacggguc                    40

<210> SEQ ID NO 10
<211> LENGTH: 19
<212> TYPE: RNA
<213> ORGANISM: artificial
<220> FEATURE:
<223> OTHER INFORMATION: firefly Luciferase siRNA 1 antisense strand

<400> SEQUENCE: 10
guuggcacca gcagcgcac                                            19

<210> SEQ ID NO 11
<211> LENGTH: 19
<212> TYPE: RNA
<213> ORGANISM: artificial
<220> FEATURE:
<223> OTHER INFORMATION: firefly Luciferase siRNA 2 antisense strand

<400> SEQUENCE: 11
ucgaaguacu cagcguaag                                            19

<210> SEQ ID NO 12
<211> LENGTH: 19
<212> TYPE: RNA
<213> ORGANISM: artificial
<220> FEATURE:
<223> OTHER INFORMATION: firefly Luciferase siRNA 3 antisense strand

<400> SEQUENCE: 12
gcccauaucg uuucauagc                                            19

<210> SEQ ID NO 13
<211> LENGTH: 19
<212> TYPE: RNA
<213> ORGANISM: artificial
<220> FEATURE:
<223> OTHER INFORMATION: firefly Luciferase siRNA 4 antisense strand

<400> SEQUENCE: 13
guagaugaga ugugacgaa                                            19

<210> SEQ ID NO 14
<211> LENGTH: 19
<212> TYPE: RNA

```
<213> ORGANISM: artificial
<220> FEATURE:
<223> OTHER INFORMATION: scramble control of firefly Luciferase siRNA
      antisense strand

<400> SEQUENCE: 14
gucgguuucg ugaaggaga                                                 19

<210> SEQ ID NO 15
<211> LENGTH: 18
<212> TYPE: RNA
<213> ORGANISM: artificial
<220> FEATURE:
<223> OTHER INFORMATION: an a3WJ RNA polynucleotide

<400> SEQUENCE: 15
uugccaugug uauguggg                                                  18

<210> SEQ ID NO 16
<211> LENGTH: 20
<212> TYPE: RNA
<213> ORGANISM: artificial
<220> FEATURE:
<223> OTHER INFORMATION: a b3WJ RNA polynucleotide

<400> SEQUENCE: 16
cccacauacu uuguugaucc                                                20

<210> SEQ ID NO 17
<211> LENGTH: 16
<212> TYPE: RNA
<213> ORGANISM: artificial
<220> FEATURE:
<223> OTHER INFORMATION: c3WJ RNA polynucleotide

<400> SEQUENCE: 17
ggaucaauca uggcaa                                                    16

<210> SEQ ID NO 18
<211> LENGTH: 27
<212> TYPE: RNA
<213> ORGANISM: artificial
<220> FEATURE:
<223> OTHER INFORMATION: an aX-RNA polynucleotide

<400> SEQUENCE: 18
uugccaugug uauguggguu ccagcac                                        27

<210> SEQ ID NO 19
<211> LENGTH: 17
<212> TYPE: RNA
<213> ORGANISM: artificial
<220> FEATURE:
<223> OTHER INFORMATION: a bX-RNA polynucleotide

<400> SEQUENCE: 19
gugcuggaac ugacugc                                                   17

<210> SEQ ID NO 20
<211> LENGTH: 28
<212> TYPE: RNA
<213> ORGANISM: artificial
<220> FEATURE:
<223> OTHER INFORMATION: a cX-RNA polynucleotide

<400> SEQUENCE: 20
```

```
gcagucagcc cacauacuuu guugaucc                                      28
```

```
<210> SEQ ID NO 21
<211> LENGTH: 16
<212> TYPE: RNA
<213> ORGANISM: artificial
<220> FEATURE:
<223> OTHER INFORMATION: a dX-RNA polynucleotide

<400> SEQUENCE: 21
ggaucaauca uggcaa                                                   16

<210> SEQ ID NO 22
<211> LENGTH: 19
<212> TYPE: DNA
<213> ORGANISM: artificial
<220> FEATURE:
<223> OTHER INFORMATION: GAPDH left

<400> SEQUENCE: 22
agccacatcg ctcagacac                                                19

<210> SEQ ID NO 23
<211> LENGTH: 19
<212> TYPE: DNA
<213> ORGANISM: artificial
<220> FEATURE:
<223> OTHER INFORMATION: GAPDH right

<400> SEQUENCE: 23
gcccaatacg accaaatcc                                                19

<210> SEQ ID NO 24
<211> LENGTH: 22
<212> TYPE: DNA
<213> ORGANISM: artificial
<220> FEATURE:
<223> OTHER INFORMATION: survivin left

<400> SEQUENCE: 24
caccgcatct ctacattcaa ga                                            22

<210> SEQ ID NO 25
<211> LENGTH: 21
<212> TYPE: DNA
<213> ORGANISM: artificial
<220> FEATURE:
<223> OTHER INFORMATION: survivin right

<400> SEQUENCE: 25
caagtctggc tcgttctcag t                                             21

<210> SEQ ID NO 26
<211> LENGTH: 129
<212> TYPE: RNA
<213> ORGANISM: artificial
<220> FEATURE:
<223> OTHER INFORMATION: 7Ba' pRNA with 3'-end palindrome sequences

<400> SEQUENCE: 26
ggaaugguac gguacuucca uugucaugug uauguugggg auuaacaggc acugauugag   60
uucagcccac auacuuuguu gauuguccac ugucaaucau ggcaaaagug cacgcuacuu  120
ucccgaucg                                                          129
```

```
<210> SEQ ID NO 27
<211> LENGTH: 25
<212> TYPE: DNA
<213> ORGANISM: artificial
<220> FEATURE:
<223> OTHER INFORMATION: folate-DNA strand

<400> SEQUENCE: 27
ctcccggccg ccatggccgc gggat                                              25

<210> SEQ ID NO 28
<211> LENGTH: 12
<212> TYPE: RNA
<213> ORGANISM: artificial
<220> FEATURE:
<223> OTHER INFORMATION: 7Aa' right hand loop

<400> SEQUENCE: 28
gauuaagugg ac                                                            12

<210> SEQ ID NO 29
<211> LENGTH: 12
<212> TYPE: RNA
<213> ORGANISM: artificial
<220> FEATURE:
<223> OTHER INFORMATION: 7Bb' right hand loop

<400> SEQUENCE: 29
gauuaacagg ca                                                            12

<210> SEQ ID NO 30
<211> LENGTH: 12
<212> TYPE: RNA
<213> ORGANISM: artificial
<220> FEATURE:
<223> OTHER INFORMATION: 7Cc' right hand loop

<400> SEQUENCE: 30
gauuagcguu cu                                                            12

<210> SEQ ID NO 31
<211> LENGTH: 12
<212> TYPE: RNA
<213> ORGANISM: artificial
<220> FEATURE:
<223> OTHER INFORMATION: 7Dd' rigtht hand loop

<400> SEQUENCE: 31
gauuaaggcu ag                                                            12

<210> SEQ ID NO 32
<211> LENGTH: 12
<212> TYPE: RNA
<213> ORGANISM: artificial
<220> FEATURE:
<223> OTHER INFORMATION: 7Ee' right hand loop

<400> SEQUENCE: 32
gauuaagcac ca                                                            12

<210> SEQ ID NO 33
<211> LENGTH: 12
<212> TYPE: RNA
<213> ORGANISM: artificial
<220> FEATURE:
<223> OTHER INFORMATION: 7Ff' right hand loop
```

```
<400> SEQUENCE: 33
gauuaagacg ug                                                    12

<210> SEQ ID NO 34
<211> LENGTH: 12
<212> TYPE: RNA
<213> ORGANISM: artificial
<220> FEATURE:
<223> OTHER INFORMATION: 7Gg' right hand loop

<400> SEQUENCE: 34
gauuacacua uc                                                    12

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42
<211> LENGTH: 17
<212> TYPE: RNA
<213> ORGANISM: artificial
<220> FEATURE:
<223> OTHER INFORMATION: a3wj (del U)

<400> SEQUENCE: 42
uugccauggu auguggg                                               17

<210> SEQ ID NO 43
```

```
<211> LENGTH: 17
<212> TYPE: RNA
<213> ORGANISM: artificial
<220> FEATURE:
<223> OTHER INFORMATION: Sequence for b3wj (del UUU)

<400> SEQUENCE: 43
ccaacauacg uugaucc                                                    17

<210> SEQ ID NO 44
<211> LENGTH: 16
<212> TYPE: RNA
<213> ORGANISM: artificial
<220> FEATURE:
<223> OTHER INFORMATION: Sequence for b3wj (del 4-nt)

<400> SEQUENCE: 44
aacauacuuu guugau                                                     16

<210> SEQ ID NO 45
<211> LENGTH: 12
<212> TYPE: RNA
<213> ORGANISM: artificial
<220> FEATURE:
<223> OTHER INFORMATION: Sequence for c3wj (del 4-nt)

<400> SEQUENCE: 45
aucaaucagu gc                                                         12

<210> SEQ ID NO 46
<211> LENGTH: 12
<212> TYPE: RNA
<213> ORGANISM: artificial
<220> FEATURE:
<223> OTHER INFORMATION: 16s RNA H34-H35-H38  a3wj core

<400> SEQUENCE: 46
ggggacgacg uc                                                         12

<210> SEQ ID NO 47
<211> LENGTH: 14
<212> TYPE: RNA
<213> ORGANISM: artificial
<220> FEATURE:
<223> OTHER INFORMATION: 16s RNA H34-H35-H38 b3wj core

<400> SEQUENCE: 47
cgagcgcaac cccc                                                       14

<210> SEQ ID NO 48
<211> LENGTH: 12
<212> TYPE: RNA
<213> ORGANISM: artificial
<220> FEATURE:
<223> OTHER INFORMATION: 16s RNA H34-H35-H38 c3wj core

<400> SEQUENCE: 48
gucgucagcu cg                                                         12

<210> SEQ ID NO 49
<211> LENGTH: 11
<212> TYPE: RNA
<213> ORGANISM: artificial
<220> FEATURE:
<223> OTHER INFORMATION: 23S RNA H75-H76-H79 a3wj core

<400> SEQUENCE: 49
```
gaggacaccg a    11

<210> SEQ ID NO 50
<211> LENGTH: 11
<212> TYPE: RNA
<213> ORGANISM: artificial
<220> FEATURE:
<223> OTHER INFORMATION: 23S RNA H75-H76-H79 b3wj core

<400> SEQUENCE: 50
ggcucucacu c    11

<210> SEQ ID NO 51
<211> LENGTH: 10
<212> TYPE: RNA
<213> ORGANISM: artificial
<220> FEATURE:
<223> OTHER INFORMATION: 23S RNA H75-H76-H79 c3wj core

<400> SEQUENCE: 51
ucgcugagcc    10

<210> SEQ ID NO 52
<211> LENGTH: 10
<212> TYPE: RNA
<213> ORGANISM: artificial
<220> FEATURE:
<223> OTHER INFORMATION: 23S RNA H83-H84-H85 a3WJ CORE

<400> SEQUENCE: 52
agcaaaagau    10

<210> SEQ ID NO 53
<211> LENGTH: 14
<212> TYPE: RNA
<213> ORGANISM: artificial
<220> FEATURE:
<223> OTHER INFORMATION: 23S RNA H83-H84-H85 b3WJ CORE

<400> SEQUENCE: 53
cccggcgaag agug    14

<210> SEQ ID NO 54
<211> LENGTH: 12
<212> TYPE: RNA
<213> ORGANISM: artificial
<220> FEATURE:
<223> OTHER INFORMATION: 23S RNA H83-H84-H85 c3WJ CORE

<400> SEQUENCE: 54
aucucagccg gg    12

<210> SEQ ID NO 55
<211> LENGTH: 15
<212> TYPE: RNA
<213> ORGANISM: artificial
<220> FEATURE:
<223> OTHER INFORMATION: 5s rRNA a3wj core

<400> SEQUENCE: 55
cccgguucgc cgcca    15

<210> SEQ ID NO 56
<211> LENGTH: 17
<212> TYPE: RNA

```
<213> ORGANISM: artificial
<220> FEATURE:
<223> OTHER INFORMATION: 5s rRNA b3wj core

<400> SEQUENCE: 56
cccaccagcg uuccggg                                                          17

<210> SEQ ID NO 57
<211> LENGTH: 19
<212> TYPE: RNA
<213> ORGANISM: artificial
<220> FEATURE:
<223> OTHER INFORMATION: 5s rRNA c3wj core

<400> SEQUENCE: 57
aggcggccau agcgguggg                                                        19

<210> SEQ ID NO 58
<211> LENGTH: 17
<212> TYPE: RNA
<213> ORGANISM: artificial
<220> FEATURE:
<223> OTHER INFORMATION: G-Riboswitch (type I) a3wj core

<400> SEQUENCE: 58
ggacauauaa ucgcgug                                                          17

<210> SEQ ID NO 59
<211> LENGTH: 16
<212> TYPE: RNA
<213> ORGANISM: artificial
<220> FEATURE:
<223> OTHER INFORMATION: G-Riboswitch (type I) b3wj core

<400> SEQUENCE: 59
auguccgacu augcc                                                            16

<210> SEQ ID NO 60
<211> LENGTH: 21
<212> TYPE: RNA
<213> ORGANISM: artificial
<220> FEATURE:
<223> OTHER INFORMATION: G-Riboswitch (type I) c3wj core

<400> SEQUENCE: 60
cacgcaaguu ucuaccgggc a                                                     21

<210> SEQ ID NO 61
<211> LENGTH: 19
<212> TYPE: RNA
<213> ORGANISM: artificial
<220> FEATURE:
<223> OTHER INFORMATION: TPP riboswitch (type II) a3wj core

<400> SEQUENCE: 61
gcgacucggg gugcccuuc                                                        19

<210> SEQ ID NO 62
<211> LENGTH: 34
<212> TYPE: RNA
<213> ORGANISM: artificial
<220> FEATURE:
<223> OTHER INFORMATION: TPP riboswitch (type II) b3wj core

<400> SEQUENCE: 62
gaaggcugag aaauacccgu aucaccugau cugg                                       34
```

```
<210> SEQ ID NO 63
<211> LENGTH: 18
<212> TYPE: RNA
<213> ORGANISM: artificial
<220> FEATURE:
<223> OTHER INFORMATION: TPP riboswitch (type II) c3wj core

<400> SEQUENCE: 63
ccagcguagg gaagucgc                                                    18

<210> SEQ ID NO 64
<211> LENGTH: 21
<212> TYPE: RNA
<213> ORGANISM: artificial
<220> FEATURE:
<223> OTHER INFORMATION: M-box Riboswitch (type II) a3wj core

<400> SEQUENCE: 64
gacgccaaug ggucaacaga a                                                21

<210> SEQ ID NO 65
<211> LENGTH: 20
<212> TYPE: RNA
<213> ORGANISM: artificial
<220> FEATURE:
<223> OTHER INFORMATION: M-box Riboswitch (type II) b3wj core

<400> SEQUENCE: 65
aggugauuuu uaaugcagcu                                                  20

<210> SEQ ID NO 66
<211> LENGTH: 21
<212> TYPE: RNA
<213> ORGANISM: artificial
<220> FEATURE:
<223> OTHER INFORMATION: M-box Riboswitch (type II) c3wj core

<400> SEQUENCE: 66
acgcugcugc ccaaaaaugu c                                                21

<210> SEQ ID NO 67
<211> LENGTH: 12
<212> TYPE: RNA
<213> ORGANISM: artificial
<220> FEATURE:
<223> OTHER INFORMATION: Hammerhead ribozyme a3wj core

<400> SEQUENCE: 67
cugucaccgg au                                                          12

<210> SEQ ID NO 68
<211> LENGTH: 11
<212> TYPE: RNA
<213> ORGANISM: artificial
<220> FEATURE:
<223> OTHER INFORMATION: Hammerhead ribozyme b3wj core

<400> SEQUENCE: 68
ggacgaaaca g                                                           11

<210> SEQ ID NO 69
<211> LENGTH: 18
<212> TYPE: RNA
<213> ORGANISM: artificial
<220> FEATURE:
```

```
<223> OTHER INFORMATION: Hammerhead ribozyme c3wj core

<400> SEQUENCE: 69
uuccggucug augagucc                                                        18

<210> SEQ ID NO 70
<211> LENGTH: 14
<212> TYPE: RNA
<213> ORGANISM: artificial
<220> FEATURE:
<223> OTHER INFORMATION: Alu SRP

<400> SEQUENCE: 70
gggccgggcg cggu                                                            14

<210> SEQ ID NO 71
<211> LENGTH: 11
<212> TYPE: RNA
<213> ORGANISM: artificial
<220> FEATURE:
<223> OTHER INFORMATION: Alu SRP

<400> SEQUENCE: 71
ucgggaggcu c                                                               11

<210> SEQ ID NO 72
<211> LENGTH: 22
<212> TYPE: RNA
<213> ORGANISM: artificial
<220> FEATURE:
<223> OTHER INFORMATION: AluSRP

<400> SEQUENCE: 72
ggcgcgcgcc uguaguccca gc                                                   22

<210> SEQ ID NO 73
<211> LENGTH: 21
<212> TYPE: RNA
<213> ORGANISM: artificial
<220> FEATURE:
<223> OTHER INFORMATION: HCV a3wj core

<400> SEQUENCE: 73
ucauggucuu ccggaaagcg c                                                    21

<210> SEQ ID NO 74
<211> LENGTH: 20
<212> TYPE: RNA
<213> ORGANISM: artificial
<220> FEATURE:
<223> OTHER INFORMATION: HCV b3wj core

<400> SEQUENCE: 74
gugaugagcc gaucgucaga                                                      20

<210> SEQ ID NO 75
<211> LENGTH: 16
<212> TYPE: RNA
<213> ORGANISM: artificial
<220> FEATURE:
<223> OTHER INFORMATION: HCV  c3wj core

<400> SEQUENCE: 75
ucuggugaua ccgaga                                                          16
```

```
<210> SEQ ID NO 76
<211> LENGTH: 18
<212> TYPE: RNA
<213> ORGANISM: artificial
<220> FEATURE:
<223> OTHER INFORMATION: pRNA a3WJ core

<400> SEQUENCE: 76
uugccaugug uauguggg                                                 18

<210> SEQ ID NO 77
<211> LENGTH: 20
<212> TYPE: RNA
<213> ORGANISM: artificial
<220> FEATURE:
<223> OTHER INFORMATION: pRNA c3wj core

<400> SEQUENCE: 77
cccacauacu uuguugaucc                                               20

<210> SEQ ID NO 78
<211> LENGTH: 16
<212> TYPE: RNA
<213> ORGANISM: artificial
<220> FEATURE:
<223> OTHER INFORMATION: pRNA c3wj core

<400> SEQUENCE: 78
ggaucaauca uggcaa                                                   16

<210> SEQ ID NO 79
<211> LENGTH: 15
<212> TYPE: RNA
<213> ORGANISM: artificial
<220> FEATURE:
<223> OTHER INFORMATION: 16s H22-H23-H23a a3wJ core

<400> SEQUENCE: 79
ggaacgccga uggcg                                                    15

<210> SEQ ID NO 80
<211> LENGTH: 16
<212> TYPE: RNA
<213> ORGANISM: artificial
<220> FEATURE:
<223> OTHER INFORMATION: 16s H22-H23-H23a b3wJ core

<400> SEQUENCE: 80
gagagggugg uggaau                                                   16

<210> SEQ ID NO 81
<211> LENGTH: 14
<212> TYPE: RNA
<213> ORGANISM: artificial
<220> FEATURE:
<223> OTHER INFORMATION: 16s H22-H23-H23a c3wJ core

<400> SEQUENCE: 81
ggcagccacc uggu                                                     14

<210> SEQ ID NO 82
<211> LENGTH: 12
<212> TYPE: RNA
<213> ORGANISM: artificial
<220> FEATURE:
<223> OTHER INFORMATION: 16s H25-H25-H26a a3wj Core
```

```
<400> SEQUENCE: 82
cgcguuaagc gc                                                          12

<210> SEQ ID NO 83
<211> LENGTH: 11
<212> TYPE: RNA
<213> ORGANISM: artificial
<220> FEATURE:
<223> OTHER INFORMATION: 16s H25-H25-H26a b3wj core

<400> SEQUENCE: 83
gggccgaagc u                                                           11

<210> SEQ ID NO 84
<211> LENGTH: 11
<212> TYPE: RNA
<213> ORGANISM: artificial
<220> FEATURE:
<223> OTHER INFORMATION: 16s H25-H25-H26a c3wj core

<400> SEQUENCE: 84
gcgcuagguc u                                                           11

<210> SEQ ID NO 85
<211> LENGTH: 11
<212> TYPE: RNA
<213> ORGANISM: artificial
<220> FEATURE:
<223> OTHER INFORMATION: 23s H48-Hx-H60 a3wj core

<400> SEQUENCE: 85
gccuaaugga u                                                           11

<210> SEQ ID NO 86
<211> LENGTH: 10
<212> TYPE: RNA
<213> ORGANISM: artificial
<220> FEATURE:
<223> OTHER INFORMATION: 23s H48-Hx-H60 b3wj core

<400> SEQUENCE: 86
aagccaaggc                                                             10

<210> SEQ ID NO 87
<211> LENGTH: 11
<212> TYPE: RNA
<213> ORGANISM: artificial
<220> FEATURE:
<223> OTHER INFORMATION: 23s H48-Hx-H60 c3wj core

<400> SEQUENCE: 87
guccauggcg g                                                           11

<210> SEQ ID NO 88
<211> LENGTH: 17
<212> TYPE: RNA
<213> ORGANISM: artificial
<220> FEATURE:
<223> OTHER INFORMATION: 23s H99-H100-H101 a3wj Core

<400> SEQUENCE: 88
gacgcggucg auagacu                                                     17

<210> SEQ ID NO 89
<211> LENGTH: 10
```

```
<212> TYPE: RNA
<213> ORGANISM: artificial
<220> FEATURE:
<223> OTHER INFORMATION: 23s H99-H100-H101 b3wj core

<400> SEQUENCE: 89
ucccgcguac                                                            10

<210> SEQ ID NO 90
<211> LENGTH: 12
<212> TYPE: RNA
<213> ORGANISM: artificial
<220> FEATURE:
<223> OTHER INFORMATION: 23s H99-H100-H101 c3wj core

<400> SEQUENCE: 90
agcacuaaca ga                                                         12

<210> SEQ ID NO 91
<211> LENGTH: 13
<212> TYPE: RNA
<213> ORGANISM: artificial
<220> FEATURE:
<223> OTHER INFORMATION: 16s H-33-H33a-H33b a3wj core

<400> SEQUENCE: 91
agggaacccg ggu                                                        13

<210> SEQ ID NO 92

<400> SEQUENCE: 92

000

<210> SEQ ID NO 93
<211> LENGTH: 13
<212> TYPE: RNA
<213> ORGANISM: artificial
<220> FEATURE:
<223> OTHER INFORMATION: 16s H-33-H33a-H33b c3wj core

<400> SEQUENCE: 93
gccuggggug ccc                                                        13

<210> SEQ ID NO 94
<211> LENGTH: 12
<212> TYPE: RNA
<213> ORGANISM: artificial
<220> FEATURE:
<223> OTHER INFORMATION: 23s H33-H34-H35 a3wj core

<400> SEQUENCE: 94
uguguagggg ug                                                         12

<210> SEQ ID NO 95
<211> LENGTH: 13
<212> TYPE: RNA
<213> ORGANISM: artificial
<220> FEATURE:
<223> OTHER INFORMATION: 23s H33-H34-H35 b3wj core

<400> SEQUENCE: 95
gacgaucuac gca                                                        13

<210> SEQ ID NO 96
<211> LENGTH: 13
```

```
<212> TYPE: RNA
<213> ORGANISM: artificial
<220> FEATURE:
<223> OTHER INFORMATION: 23s H33-H34-H35 c3wj core

<400> SEQUENCE: 96
ggcccaucga guc                                                    13

<210> SEQ ID NO 97
<211> LENGTH: 12
<212> TYPE: RNA
<213> ORGANISM: artificial
<220> FEATURE:
<223> OTHER INFORMATION: 16s H28-H29-H43 a3wj core

<400> SEQUENCE: 97
aucgcuagua au                                                     12

<210> SEQ ID NO 98
<211> LENGTH: 17
<212> TYPE: RNA
<213> ORGANISM: artificial
<220> FEATURE:
<223> OTHER INFORMATION: 16s H28-H29-H43 b3wj core

<400> SEQUENCE: 98
gugaauacgu ucccggg                                                17

<210> SEQ ID NO 99
<211> LENGTH: 14
<212> TYPE: RNA
<213> ORGANISM: artificial
<220> FEATURE:
<223> OTHER INFORMATION: 16s H28-H29-H43 c3wj core

<400> SEQUENCE: 99
cccgcacaag gggu                                                   14

<210> SEQ ID NO 100
<211> LENGTH: 25
<212> TYPE: RNA
<213> ORGANISM: artificial
<220> FEATURE:
<223> OTHER INFORMATION: 16s H32-H33-H34 a 3wj core

<400> SEQUENCE: 100
ucagcauggc ccuuacggcc ugggc                                       25

<210> SEQ ID NO 101
<211> LENGTH: 16
<212> TYPE: RNA
<213> ORGANISM: artificial
<220> FEATURE:
<223> OTHER INFORMATION: 16s H32-H33-H34 b3wj Core

<400> SEQUENCE: 101
cacaggugcu gcaugg                                                 16

<210> SEQ ID NO 102
<211> LENGTH: 18
<212> TYPE: RNA
<213> ORGANISM: artificial
<220> FEATURE:
<223> OTHER INFORMATION: 16s H32-H33-H34 c3wj Core

<400> SEQUENCE: 102
```

```
uuaccaggcc uugacaug                                                  18

<210> SEQ ID NO 103

<400> SEQUENCE: 103

000

<210> SEQ ID NO 104
<211> LENGTH: 11
<212> TYPE: RNA
<213> ORGANISM: artificial
<220> FEATURE:
<223> OTHER INFORMATION: RNase P B type b3wj core

<400> SEQUENCE: 104
gguaaacccc u                                                         11

<210> SEQ ID NO 105
<211> LENGTH: 14
<212> TYPE: RNA
<213> ORGANISM: artificial
<220> FEATURE:
<223> OTHER INFORMATION: RNase P B type c3wj core

<400> SEQUENCE: 105
uccuugaaag ugcc                                                      14

<210> SEQ ID NO 106
<211> LENGTH: 15
<212> TYPE: RNA
<213> ORGANISM: artificial
<220> FEATURE:
<223> OTHER INFORMATION: L11-rRNA a3wj core

<400> SEQUENCE: 106
gccaggaugu aggcu                                                     15

<210> SEQ ID NO 107
<211> LENGTH: 11
<212> TYPE: RNA
<213> ORGANISM: artificial
<220> FEATURE:
<223> OTHER INFORMATION: L11-rRNA b3wj core

<400> SEQUENCE: 107
agcucacugg u                                                         11

<210> SEQ ID NO 108
<211> LENGTH: 23
<212> TYPE: RNA
<213> ORGANISM: artificial
<220> FEATURE:
<223> OTHER INFORMATION: L11-rRNA c3wj core

<400> SEQUENCE: 108
gcagccauca uuuaaagaaa gcg                                            23

<210> SEQ ID NO 109
<211> LENGTH: 20
<212> TYPE: RNA
<213> ORGANISM: artificial
<220> FEATURE:
<223> OTHER INFORMATION: M2/NF a3wj core

<400> SEQUENCE: 109
```

-continued

```
uaguauggca caugauuggg                                           20

<210> SEQ ID NO 110
<211> LENGTH: 16
<212> TYPE: RNA
<213> ORGANISM: artificial
<220> FEATURE:
<223> OTHER INFORMATION: M2/NF b3wj core

<400> SEQUENCE: 110
cccacauguc acgggg                                               16

<210> SEQ ID NO 111
<211> LENGTH: 11
<212> TYPE: RNA
<213> ORGANISM: artificial
<220> FEATURE:
<223> OTHER INFORMATION: M2/NF c3wj core

<400> SEQUENCE: 111
cccucuuacu a                                                    11

<210> SEQ ID NO 112
<211> LENGTH: 17
<212> TYPE: RNA
<213> ORGANISM: artificial
<220> FEATURE:
<223> OTHER INFORMATION: SF5 a3wj core

<400> SEQUENCE: 112
uaauguaugu gugucgg                                              17

<210> SEQ ID NO 113
<211> LENGTH: 15
<212> TYPE: RNA
<213> ORGANISM: artificial
<220> FEATURE:
<223> OTHER INFORMATION: SF5 b3wj core

<400> SEQUENCE: 113
ccgacagcag gggag                                                15

<210> SEQ ID NO 114
<211> LENGTH: 11
<212> TYPE: RNA
<213> ORGANISM: artificial
<220> FEATURE:
<223> OTHER INFORMATION: SF5 c3wj core

<400> SEQUENCE: 114
cucuugcauu a                                                    11

<210> SEQ ID NO 115
<211> LENGTH: 20
<212> TYPE: RNA
<213> ORGANISM: artificial
<220> FEATURE:
<223> OTHER INFORMATION: B103 a3wj core

<400> SEQUENCE: 115
uaguauggug cgugauuggg                                           20

<210> SEQ ID NO 116
<211> LENGTH: 16
<212> TYPE: RNA
<213> ORGANISM: artificial
```

```
<220> FEATURE:
<223> OTHER INFORMATION: B103 b3wj core

<400> SEQUENCE: 116
cccacacgcc acgggg                                                      16

<210> SEQ ID NO 117
<211> LENGTH: 11
<212> TYPE: RNA
<213> ORGANISM: artificial
<220> FEATURE:
<223> OTHER INFORMATION: B103 c3wj core

<400> SEQUENCE: 117
cccucuuacu a                                                           11

<210> SEQ ID NO 118
<211> LENGTH: 19
<212> TYPE: RNA
<213> ORGANISM: artificial
<220> FEATURE:
<223> OTHER INFORMATION: GA1 a3wj core

<400> SEQUENCE: 118
auauauggcu gugcaacgg                                                   19

<210> SEQ ID NO 119
<211> LENGTH: 18
<212> TYPE: RNA
<213> ORGANISM: artificial
<220> FEATURE:
<223> OTHER INFORMATION: GA1 b3wj core

<400> SEQUENCE: 119
ccguugacag guuguugc                                                    18

<210> SEQ ID NO 120
<211> LENGTH: 14
<212> TYPE: RNA
<213> ORGANISM: artificial
<220> FEATURE:
<223> OTHER INFORMATION: GA1 c3wj core

<400> SEQUENCE: 120
gcaauacuau auau                                                        14

<210> SEQ ID NO 121
<211> LENGTH: 41
<212> TYPE: RNA
<213> ORGANISM: artificial
<220> FEATURE:
<223> OTHER INFORMATION: 41nt RNA

<400> SEQUENCE: 121
ggaucaauca uggccaaucc cgcggccaug gcggccggga g                          41

<210> SEQ ID NO 122
<211> LENGTH: 59
<212> TYPE: DNA
<213> ORGANISM: artificial
<220> FEATURE:
<223> OTHER INFORMATION: 41nt Rna 5' Primer

<400> SEQUENCE: 122
taataggact cactatagga tcaatcatgg ccaatcccgc ggccatggcg gccgggaag       59
```

<210> SEQ ID NO 123
<211> LENGTH: 58
<212> TYPE: DNA
<213> ORGANISM: artificial
<220> FEATURE:
<223> OTHER INFORMATION: 41nt RNA 3' primer

<400> SEQUENCE: 123
ctcccggccg ccatggccgc gggattggcc atgattgatc ctatagtgag tcgtatta        58

<210> SEQ ID NO 124
<211> LENGTH: 106
<212> TYPE: RNA
<213> ORGANISM: artificial
<220> FEATURE:
<223> OTHER INFORMATION: 106nt RNA harboring HBV ribozyme

<400> SEQUENCE: 124
ggccaugugu augggaaa acaaauucuu uacugaugag uccgugagga cgaaacgggu         60
caaaacccac auacuuuguu gauccgcagg uuccuuaucu gucauu                    106

<210> SEQ ID NO 125
<211> LENGTH: 68
<212> TYPE: DNA
<213> ORGANISM: artificial
<220> FEATURE:
<223> OTHER INFORMATION: 106nt RNA harboring HBV ribozyme  DNA template

<400> SEQUENCE: 125
gtgtatgtgg gaaacaaat tctttactga tgagtccgtg aggacgaaac gggtcaaaac        60
ccacatac                                                               68

<210> SEQ ID NO 126
<211> LENGTH: 39
<212> TYPE: DNA
<213> ORGANISM: artificial
<220> FEATURE:
<223> OTHER INFORMATION: 106nt RNA harboring HBV ribozyme 5' primer

<400> SEQUENCE: 126
taatacgact cactataggc catgtgtatg tgggaaaac                              39

<210> SEQ ID NO 127
<211> LENGTH: 50
<212> TYPE: DNA
<213> ORGANISM: artificial
<220> FEATURE:
<223> OTHER INFORMATION: 106nt RNA harboring HBV ribozyme 3' primer
      (siRNA)

<400> SEQUENCE: 127
aatgacagat aaggaacctg cggatcaaca agtatgtggg ttttgacccg                  50

<210> SEQ ID NO 128
<211> LENGTH: 51
<212> TYPE: DNA
<213> ORGANISM: artificial
<220> FEATURE:
<223> OTHER INFORMATION: 106nt RNA harboring HBV ribozyme 3' primer
      (siRNA)

<400> SEQUENCE: 128
aaatagtggg accaatcaag cggatcaaca agtatgtgg gttttgaccc g                 51

<210> SEQ ID NO 129
<211> LENGTH: 106
<212> TYPE: RNA
<213> ORGANISM: artificial
<220> FEATURE:
<223> OTHER INFORMATION: 106nt RNA harboring disabaled HBV ribozyme

<400> SEQUENCE: 129
ggccaugugu augugggaaa acaaauucuu uacuaaugag uccgugagga cgaaacgggu    60
caaaacccac auacuuuguu gauccgcagg uuccuuaucu gucauu                   106

<210> SEQ ID NO 130
<211> LENGTH: 68
<212> TYPE: DNA
<213> ORGANISM: artificial
<220> FEATURE:
<223> OTHER INFORMATION: 106nt RNA harboring diisabaled HBV ribozyme DNA
      template

<400> SEQUENCE: 130
gtgtatgtgg gaaacaaat tctttactaa tgagtccgtg aggacgaaac gggtcaaaac     60
ccacatac                                                             68

<210> SEQ ID NO 131
<211> LENGTH: 39
<212> TYPE: DNA
<213> ORGANISM: artificial
<220> FEATURE:
<223> OTHER INFORMATION: 106nt RNA harboring disabled HBV ribozyme 5'
      primer

<400> SEQUENCE: 131
taatacgact cactataggc catgtgtatg tgggaaaac                            39

<210> SEQ ID NO 132
<211> LENGTH: 52
<212> TYPE: DNA
<213> ORGANISM: artificial
<220> FEATURE:
<223> OTHER INFORMATION: 106nt RNA harboring disabled HBV ribozyme 3'
      primer (siRNA)

<400> SEQUENCE: 132
aatgacagat aaggaacctg cgggatcaac aaagtatgtg gttttgacc cg             52

<210> SEQ ID NO 133
<211> LENGTH: 51
<212> TYPE: DNA
<213> ORGANISM: artificial
<220> FEATURE:
<223> OTHER INFORMATION: 106nt RNA harboring disabled HBV ribozyme 3'
      primer (siRNA)

<400> SEQUENCE: 133
aaatagtggg accaatcaag cggatcaaca aagtatgtgg gttttgaccc g             51

<210> SEQ ID NO 134
<211> LENGTH: 96
<212> TYPE: RNA
<213> ORGANISM: artificial
<220> FEATURE:
<223> OTHER INFORMATION: 96 nt RNA harboring MG binding apatamer

<400> SEQUENCE: 134
ggccaugugu auguggggga ucccgacugg cgagagccag guaacgaaug gauccccac    60

-continued auacuuuguu gauccgcagg uuccuuaucu gucauu        96

<210> SEQ ID NO 135
<211> LENGTH: 69
<212> TYPE: DNA
<213> ORGANISM: artificial
<220> FEATURE:
<223> OTHER INFORMATION: 96nt RNA harboring MGbinding aptamer DNA
      template

<400> SEQUENCE: 135
gtgtatgtgg gggatcccga ctggcgagag ccaggtaacg aatggatccc ccacatactt        60
tgttgatcc        69

<210> SEQ ID NO 136
<211> LENGTH: 42
<212> TYPE: DNA
<213> ORGANISM: artificial
<220> FEATURE:
<223> OTHER INFORMATION: 96nt RNA harboring MGbinding aptamer 5' primer

<400> SEQUENCE: 136
taatacgact cactataggc catgtgtatg tgggggatcc cg        42

<210> SEQ ID NO 137
<211> LENGTH: 33
<212> TYPE: DNA
<213> ORGANISM: artificial
<220> FEATURE:
<223> OTHER INFORMATION: 96nt RNA harboring MGbinding aptamer 3' primer
      (siRNA)

<400> SEQUENCE: 137
aatgacagat aaggaacctg cggatcaaca aag        33

<210> SEQ ID NO 138
<211> LENGTH: 33
<212> TYPE: DNA
<213> ORGANISM: artificial
<220> FEATURE:
<223> OTHER INFORMATION: 96nt RNA harboring MGbinding aptamer 3' primer
      (scramble)

<400> SEQUENCE: 138
aaatagtggg accaatcaag cggatcaaca aag        33

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

```
<400> SEQUENCE: 142
000

<210> SEQ ID NO 143
<400> SEQUENCE: 143
000

<210> SEQ ID NO 144
<400> SEQUENCE: 144
000

<210> SEQ ID NO 145
<400> SEQUENCE: 145
000

<210> SEQ ID NO 146
<400> SEQUENCE: 146
000

<210> SEQ ID NO 147
<400> SEQUENCE: 147
000

<210> SEQ ID NO 148
<400> SEQUENCE: 148
000

<210> SEQ ID NO 149
<400> SEQUENCE: 149
000

<210> SEQ ID NO 150
<400> SEQUENCE: 150
000

<210> SEQ ID NO 151
<400> SEQUENCE: 151
000

<210> SEQ ID NO 152
<400> SEQUENCE: 152
000

<210> SEQ ID NO 153
<400> SEQUENCE: 153
```

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

<210> SEQ ID NO 157
<211> LENGTH: 19
<212> TYPE: RNA
<213> ORGANISM: artificial
<220> FEATURE:
<223> OTHER INFORMATION: Luciferase-1 siRNA

<400> SEQUENCE: 157
gugcgcugcu ggugccaac                                              19

<210> SEQ ID NO 158
<211> LENGTH: 19
<212> TYPE: RNA
<213> ORGANISM: artificial
<220> FEATURE:
<223> OTHER INFORMATION: Luciferase-2 siRNA

<400> SEQUENCE: 158
cuuacgcuga guacuucga                                              19

<210> SEQ ID NO 159
<211> LENGTH: 19
<212> TYPE: RNA
<213> ORGANISM: artificial
<220> FEATURE:
<223> OTHER INFORMATION: Luciferase-3 siRNA

<400> SEQUENCE: 159
gcuaugaaac gauaugggc                                              19

<210> SEQ ID NO 160
<211> LENGTH: 19
<212> TYPE: RNA
<213> ORGANISM: artificial
<220> FEATURE:
<223> OTHER INFORMATION: Luciferase-4 siRNA

<400> SEQUENCE: 160
uucgucacau cucaucuac                                              19

<210> SEQ ID NO 161
<211> LENGTH: 19
<212> TYPE: RNA
<213> ORGANISM: artificial
<220> FEATURE:
<223> OTHER INFORMATION: scramble siRNA

```
<400> SEQUENCE: 161
ucuccuucac gaaaccgac                                                  19

<210> SEQ ID NO 162
<211> LENGTH: 123
<212> TYPE: RNA
<213> ORGANISM: artificial
<220> FEATURE:
<223> OTHER INFORMATION: loop extended pRNA homo-dimers 7Aa'

<400> SEQUENCE: 162 ggaauggua c gguacuucca uugucaugug uauguugggg auuaagugga ccugauugag     60
uucagcccac auacuuuguu gauguccac ugucaaucau ggcaaaagug cacgcuacuu     120
ucc                                                                  123

<210> SEQ ID NO 163
<211> LENGTH: 123
<212> TYPE: RNA
<213> ORGANISM: artificial
<220> FEATURE:
<223> OTHER INFORMATION: loop extended pRNA homo-dimers 7Bb'

<400> SEQUENCE: 163 ggaauggua c gguacuucca uugucaugug uauguugggg auuaacaggc acugauugag     60
uucagcccac auacuuuguu gauugccug ugucaaucau ggcaaaagug cacgcuacuu     120
ucc                                                                  123

<210> SEQ ID NO 164
<211> LENGTH: 123
<212> TYPE: RNA
<213> ORGANISM: artificial
<220> FEATURE:
<223> OTHER INFORMATION: loop extended pRNA homo-dimers 7Cc'

<400> SEQUENCE: 164 ggaauggua c gguacuucca uugucaugug uauguugggg auuagcguuc ucugauugag     60
uucagcccac auacuuuguu gauuagaacg cgucaaucau ggcaaaagug cacgcuacuu     120
ucc                                                                  123

<210> SEQ ID NO 165
<211> LENGTH: 123
<212> TYPE: RNA
<213> ORGANISM: artificial
<220> FEATURE:
<223> OTHER INFORMATION: Sequence of loop extended pRNA homo-dimers 7Dd'

<400> SEQUENCE: 165 ggaauggua c gguacuucca uugucaugug uauguugggg auuaaggcua gcugauugag     60
uucagcccac auacuuuguu gauucuagcc ugucaaucau ggcaaaagug cacgcuacuu     120
ucc                                                                  123

<210> SEQ ID NO 166
<211> LENGTH: 123
<212> TYPE: RNA
<213> ORGANISM: artificial
<220> FEATURE:
<223> OTHER INFORMATION: loop extended pRNA homo-dimers 7Ee'

<400> SEQUENCE: 166 ggaauggua c gguacuucca uugucaugug uauguugggg auuaagcacc acugauugag     60
```

```
uucagcccac auacuuuguu gauuuggugc ugucaaucau ggcaaaagug cacgcuacuu    120
ucc                                                                 123

<210> SEQ ID NO 167
<211> LENGTH: 123
<212> TYPE: RNA
<213> ORGANISM: artificial
<220> FEATURE:
<223> OTHER INFORMATION: loop extended pRNA homo-dimers 7Ff'

<400> SEQUENCE: 167 ggaauggua cgguacuucca uugucaugug uauguugggg auuaagacgu gcugauugag     60
uucagcccac auacuuuguu gauucacguc ugucaaucau ggcaaaagug cacgcuacuu    120
ucc                                                                 123

<210> SEQ ID NO 168
<211> LENGTH: 123
<212> TYPE: RNA
<213> ORGANISM: artificial
<220> FEATURE:
<223> OTHER INFORMATION: loop extended pRNA homo-dimers 7Gg'

<400> SEQUENCE: 168 ggaauggua cgguacuucca uugucaugug uauguugggg auuacacuau ccugauugag     60
uucagcccac auacuuuguu gaugauagu ggucaaucau ggcaaaagug cacgcuacuu    120
ucc                                                                 123

<210> SEQ ID NO 169
<211> LENGTH: 123
<212> TYPE: RNA
<213> ORGANISM: artificial
<220> FEATURE:
<223> OTHER INFORMATION: loop extended pRNA homo-dimers 7Hh'

<400> SEQUENCE: 169 ggaauggua cgguacuucca uugucaugug uauguugggg auuaaggcag ccugauugag     60
uucagcccac auacuuuguu gaugcugcc ugucaaucau ggcaaaagug cacgcuacuu    120
ucc                                                                 123

<210> SEQ ID NO 170
<211> LENGTH: 123
<212> TYPE: RNA
<213> ORGANISM: artificial
<220> FEATURE:
<223> OTHER INFORMATION: loop extended pRNA homo-dimers 7Ii'

<400> SEQUENCE: 170 ggaauggua cgguacuucca uugucaugug uauguugggg auuaagccug ccugauugag     60
uucagcccac auacuuuguu gaugcaggc ugucaaucau ggcaaaagug cacgcuacuu    120
ucc                                                                 123

<210> SEQ ID NO 171
<211> LENGTH: 123
<212> TYPE: RNA
<213> ORGANISM: artificial
<220> FEATURE:
<223> OTHER INFORMATION: loop extended pRNA hetero-monomers 7Ba'

<400> SEQUENCE: 171
``` ggaauggua cgguacuucca uugucaugug uauguugggg auuaacaggc acugauugag    60
uucagcccac auacuuuguu gauuguccac ugucaaucau ggcaaaagug cacgcuacuu   120
ucc                                                                 123

<210> SEQ ID NO 172
<211> LENGTH: 123
<212> TYPE: RNA
<213> ORGANISM: artificial
<220> FEATURE:
<223> OTHER INFORMATION: loop extended pRNA hetero-monomers 7Cb'

<400> SEQUENCE: 172 ggaauggua cgguacuucca uugucaugug uauguugggg auuagcguuc ucugauugag    60
uucagcccac auacuuuguu gauuugccug ugucaaucau ggcaaaagug cacgcuacuu   120
ucc                                                                 123

<210> SEQ ID NO 173
<211> LENGTH: 123
<212> TYPE: RNA
<213> ORGANISM: artificial
<220> FEATURE:
<223> OTHER INFORMATION: loop extended pRNA hetero-monomers 7Dc'

<400> SEQUENCE: 173 ggaauggua cgguacuucca uugucaugug uauguugggg auuaaggcua gcugauugag    60
uucagcccac auacuuuguu gauuagaacg cgucaaucau ggcaaaagug cacgcuacuu   120
ucc                                                                 123

<210> SEQ ID NO 174
<211> LENGTH: 123
<212> TYPE: RNA
<213> ORGANISM: artificial
<220> FEATURE:
<223> OTHER INFORMATION: loop extended pRNA hetero-monomers 7Ed'

<400> SEQUENCE: 174 ggaauggua cgguacuucca uugucaugug uauguugggg auuaagcacc acugauugag    60
uucagcccac auacuuuguu gauucuagcc ugucaaucau ggcaaaagug cacgcuacuu   120
ucc                                                                 123

<210> SEQ ID NO 175
<211> LENGTH: 123
<212> TYPE: RNA
<213> ORGANISM: artificial
<220> FEATURE:
<223> OTHER INFORMATION: loop extended pRNA hetero-monomers 7Fe'

<400> SEQUENCE: 175 ggaauggua cgguacuucca uugucaugug uauguugggg auuaagacgu gcugauugag    60
uucagcccac auacuuuguu gauuuggugc ugucaaucau ggcaaaagug cacgcuacuu   120
ucc                                                                 123

<210> SEQ ID NO 176
<211> LENGTH: 123
<212> TYPE: RNA
<213> ORGANISM: artificial
<220> FEATURE:
<223> OTHER INFORMATION: loop extended pRNA hetero-monomers 7Af'

<400> SEQUENCE: 176

```
ggaaugguac gguacuucca uugucaugug uauguugggg auuaagugga ccugauugag    60
uucagcccac auacuuuguu gauucacguc ugucaaucau ggcaaaagug cacgcuacuu   120
ucc                                                                 123

<210> SEQ ID NO 177
<211> LENGTH: 123
<212> TYPE: RNA
<213> ORGANISM: artificial
<220> FEATURE:
<223> OTHER INFORMATION: loop extended pRNA hetero-monomers7Ab'

<400> SEQUENCE: 177
ggaaugguac gguacuucca uugucaugug uauguugggg auuaagugga ccugauugag    60
uucagcccac auacuuuguu gauuugccug ugucaaucau ggcaaaagug cacgcuacuu   120
ucc                                                                 123

<210> SEQ ID NO 178
<211> LENGTH: 123
<212> TYPE: RNA
<213> ORGANISM: artificial
<220> FEATURE:
<223> OTHER INFORMATION: loop extended pRNA hetero-monomers7Ac'

<400> SEQUENCE: 178
ggaaugguac gguacuucca uugucaugug uauguugggg auuaagugga ccugauugag    60
uucagcccac auacuuuguu gauuagaacg cgucaaucau ggcaaaagug cacgcuacuu   120
ucc                                                                 123

<210> SEQ ID NO 179
<211> LENGTH: 123
<212> TYPE: RNA
<213> ORGANISM: artificial
<220> FEATURE:
<223> OTHER INFORMATION: loop extended pRNA hetero-monomers7Ad'

<400> SEQUENCE: 179
ggaaugguac gguacuucca uugucaugug uauguugggg auuaagugga ccugauugag    60
uucagcccac auacuuuguu gauucuagcc ugucaaucau ggcaaaagug cacgcuacuu   120
ucc                                                                 123

<210> SEQ ID NO 180
<211> LENGTH: 123
<212> TYPE: RNA
<213> ORGANISM: artificial
<220> FEATURE:
<223> OTHER INFORMATION: loop extended pRNA hetero-monomers 7Fd'

<400> SEQUENCE: 180
ggaaugguac gguacuucca uugucaugug uauguugggg auuaagacgu gcugauugag    60
uucagcccac auacuuuguu gauucuagcc ugucaaucau ggcaaaagug cacgcuacuu   120
ucc                                                                 123

<210> SEQ ID NO 181
<211> LENGTH: 123
<212> TYPE: RNA
<213> ORGANISM: artificial
<220> FEATURE:
<223> OTHER INFORMATION: loop extended pRNA hetero-monomers 7Gf'
```

```
<400> SEQUENCE: 181 ggaauggguac gguacuucca uugucaugug uauguugggg auuacacuau ccugauugag      60
uucagcccac auacuuuguu gauucacguc ugucaaucau ggcaaaagug cacgcuacuu     120
ucc                                                                   123

<210> SEQ ID NO 182
<211> LENGTH: 123
<212> TYPE: RNA
<213> ORGANISM: artificial
<220> FEATURE:
<223> OTHER INFORMATION: loop extended pRNA hetero-monomers 7Ag'

<400> SEQUENCE: 182 ggaauggguac gguacuucca uugucaugug uauguugggg auuaagugga ccugauugag     60
uucagcccac auacuuuguu gauugauagu ggucaaucau ggcaaaagug cacgcuacuu    120
ucc                                                                  123

<210> SEQ ID NO 183
<211> LENGTH: 22
<212> TYPE: RNA
<213> ORGANISM: artificial
<220> FEATURE:
<223> OTHER INFORMATION: Foot to Foot hexamer dx-RNA+PS6

<400> SEQUENCE: 183
ggaucaauca uggcaagcau gc                                              22

<210> SEQ ID NO 184
<211> LENGTH: 37
<212> TYPE: RNA
<213> ORGANISM: artificial
<220> FEATURE:
<223> OTHER INFORMATION: 3wj-based branched hexamer a3WJFWD+a3WJREV

<400> SEQUENCE: 184
uugccaugug uaugugggug gguguaugug uaccguu                              37

<210> SEQ ID NO 185
<211> LENGTH: 38
<212> TYPE: RNA
<213> ORGANISM: artificial
<220> FEATURE:
<223> OTHER INFORMATION: 3wj-based branched hexamer a3WJFWD+b3WJREV

<400> SEQUENCE: 185
uugccaugug uaugugggcc uaguuguuuc auacaccc                             38

<210> SEQ ID NO 186
<211> LENGTH: 34
<212> TYPE: RNA
<213> ORGANISM: artificial
<220> FEATURE:
<223> OTHER INFORMATION: 3wj-based branched hexamer a3WJFWD+c3WJREV

<400> SEQUENCE: 186
uugccaugug uauguggggaa cgguacuaac uagg                                34
```